(12) United States Patent
Dorow et al.

(10) Patent No.: US 6,307,044 B1
(45) Date of Patent: Oct. 23, 2001

(54) PROCESS FOR THE PREPARATION OF MACROCYCLIC METALLOPROTEASE INHIBITORS

(75) Inventors: Roberta L. Dorow, Portage, MI (US); Silvio Campagna, New Castle, DE (US); Pasquale N. Confalone, Greenville, DE (US); Fuqiang Jin, Wilmington, DE (US); Zhe Wang, Hockessin, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/329,674

(22) Filed: Jun. 10, 1999

Related U.S. Application Data

(60) Provisional application No. 60/088,988, filed on Jun. 11, 1998.

(51) Int. Cl.⁷ .................. C07D 273/02; C07D 295/023; C07D 413/12; C07C 233/31; A61P 19/02
(52) U.S. Cl. .................. 540/454; 556/436; 556/442; 560/125; 560/183; 560/262; 564/152; 564/155; 568/675
(58) Field of Search .................. 540/454; 568/675; 560/262, 183, 125; 556/442, 436; 562/507; 564/152, 155

(56) References Cited

FOREIGN PATENT DOCUMENTS 9718207 5/1997 (WO) .

OTHER PUBLICATIONS

J. Am. Chem. Soc., 1976, 98, p. 2868.

*Primary Examiner*—Richard L. Raymond
*Assistant Examiner*—Thomas McKenzie

(57) ABSTRACT

The present invention is directed to a process for the preparation of a compound of formula (X-a):

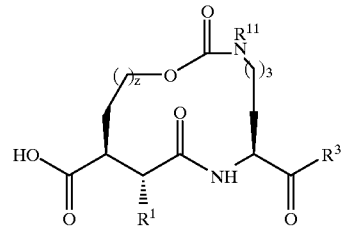

(X-a)

or a pharmaceutically acceptable salt form thereof, wherein:

$R^1$ is selected from the group consisting of:
$C_{1-5}$ alkyl substituted with 0–5 $R^{1a}$, —$(CH_2)_r$—$C_{3-10}$ cycloalkyl substituted with 0–5 $R^{1a}$, and —$(CH_2)_r$-aryl substituted with 0–5 $R^{1a}$.

Compounds of Formula (X-a) are macrocyclic molecules containing anti-succinate residues which inhibit metalloproteinases such as aggrecanase, and the production of tumor necrosis factor (TNF). The anti-succinates are formed by an Ireland Claisen rearrangement of a silyl ketene acetal which proceeds with high stereoselectivity.

22 Claims, No Drawings

PROCESS FOR THE PREPARATION OF MACROCYCLIC METALLOPROTEASE INHIBITORS

This application claims the benefit of U.S. Provisional Application No. 60/088,988, filed Jun. 11, 1998.

FIELD OF THE INVENTION

The present invention relates to processes for the preparation of macrocyclic molecules containing anti-succinate residues which inhibit metalloproteinases such as aggrecanase, and the production of tumor necrosis factor (TNF). The anti-succinates are formed by an Ireland Claisen rearrangement of a silyl ketene acetal which proceeds with high stereoselectivity. The resultant compounds are then coupled with α-amino acids to give intermediates which can readily be converted to the desired macrocyclic inhibitors.

BACKGROUND

Metalloproteinases (MP) have been implicated as the key enzymes in the destruction of mammalian cartilage and bone. There is evidence that the pathogenesis of such diseases can be modified in a beneficial manner by the administration of MP inhibitors. (Wahl et al. Ann. Rep. Med. Chem. 25, 175–184, AP, San Diego, 1990). Tumor necrosis factor (TNF) is a cell associated cytokine which has been shown to be a primary mediator in humans and in animals, of inflammation, fever, and acute phase responses, similar to those observed during acute infection and shock. There is considerable evidence that blocking the effects of TNF with specific antibodies can be beneficial in a variety of circumstances including autoimmune diseases such as rheumatoid arthritis (Feldman et al, Lancet, 1994, 344, 1105) non-insulin dependent diabetes melitus, (Lohmander L .S. et al. Arthritis Rheum. 36, 1993, 1214–22) and Crohn's disease (Macdonald T. et al. Clin. Exp. Immunol. 81, 1990, 301). PCT International Publication No. WO97/18207 discloses novel macrocycles of formula (I) which act as inhibitors of MMPs, in particular aggrecanase and TNF-C, thereby preventing cartilage loss by inflammatory disorders involving TNF.

(I)

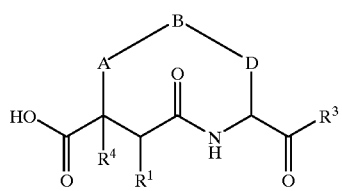

Among the most synthetically challenging are the macrocyclic analogs containing a succinate residue in which the 5(R), 6(S) stereochemistry is desired:

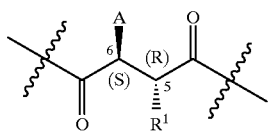

The previous synthesis of the 2,3-disubstituted succinate is described in Scheme 1. An acid halide is converted to its oxazolidinone derivative and the auxiliary directs the subsequent alkylation with t-butyl bromoacetate to afford the 5(R) stereocenter. The oxazolidinone group is removed using $H_2O_2$/LiOH. Treatment of the enolate of this acid intermediate with a triflate derivative of a di-alcohol protected at one terminus as the benzyl ether produces a succinate derivate. This intermediate, however, requires epimerization because the alkylation consistently favors the undesired syn product. In order to separate the epimerization products, the acid is esterified and subject to chromatography. Following separation, the acid is hydrolyzed and coupled with a variety of amino acids such as tyrosine or lysine which contain α-side chains amenable to cyclization. The benzyl group is removed by hydrogenation and the resulting alcohol converted to a bromide using carbon tetrabromide and triphenyl phosphine. Macrocyclization of the tyrosine or lysine derivative is accomplished using potassium carbonate in N,N-dimethylformamide. Cyclization of the lysine derivative may also be accomplished with phosgene, leading to a carbamate bridge in the macrocycle. The t-butyl group is deprotected using TFA to give the carboxylic acid, and if desired, the acid is converted to a hydroxamic acid by coupling with hydroxylamine.

Scheme 1

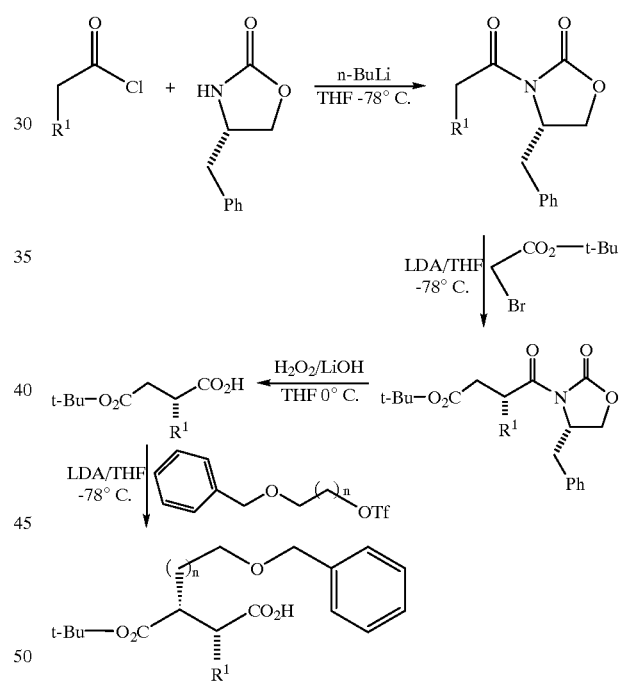

The present invention describes a new and useful process for the preparation of these macrocycles, which employs a highly stereoselective Ireland-Claisen rearrangement to form the anti-succinate residue:

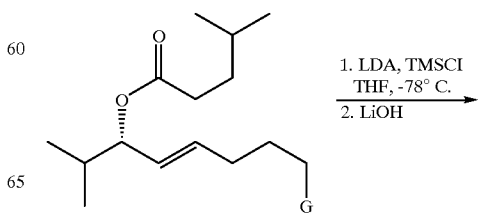

-continued

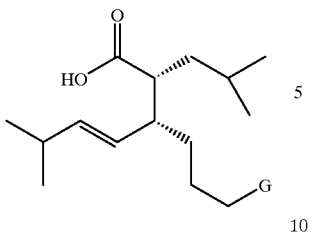

Generally, the production of anti-adducts requires either an E olefin and a Z enolate-E silyl ketene acetal or a Z olefin and an E enolate-Z silyl ketene acetal (J. Am. Chem. Soc. 1976, 98, 2868). The Claisen precursor of the present invention can be obtained by reacting an O-protected lithium 4-pentyn-1-ol (or a 4-halopentyne derivative) with an acyl chloride to give a propargylic ketone. Asymmetric reduction of the carbonyl with S-Alpine Borane® followed by hydride reduction of the alkyne yields the desired E-allylic alcohol. Acylation of the alcohol gives the scalemic ester used in the rearrangement.

The Claisen rearrangement proceeds with exceptional diastereoselectivity under the preferred conditions, eliminating the need for chromatography. The silyl ester product of the rearrangement can be isolated or immediately hydrolyzed with hydroxide to give the free acid which is then available for coupling with various α-amino acids. The compound which results from the subsequent manipulation of the chain terminus serves as the macrocyclization precursor.

If a derivative of tyrosine is used as the amino acid, the ring may be cyclized under basic conditions. This cyclization proceeds under the preferred conditions through the use of cesium carbonate in dimethyl sulfoxide and N,N-dimethylformamide. In similiar fashion, if the amino acid is a ω-protected lysine derivative, macrocyclization can be accomplished by reacting an acyclic alcohol and the deprotected amine with phosgene or an equivalent thereof in the presence of an acid scaventger to give a carbamate linkage.

Compounds of formula (IX) or (IX-a) result when amino acids derivatives such as tyrosine or lysine are coupled with the anti-succinate residues formed by a Claien rearrangement, and subsequently cyclized.

(IX)

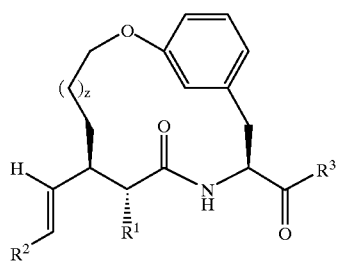

(IX-a)

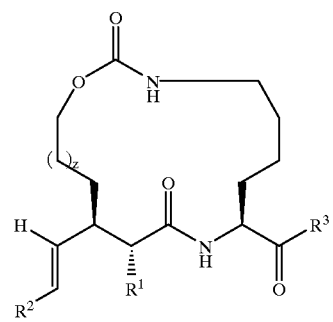

These macrocycles are converted to the corresponding carboxylic acids with $KMnO_4$ in the presence of $NaIO_4$, or with ozone. If desired, the resultant acids can be converted to alternative chelators such as hydroxamic acids by activation of the carbonyl and subsequent treatment with hydroxylamine.

Production of the anti-succinate residue (Ib) poses significant synthetic challenges to large scale drug preparation. In order to prepare large quantities of the desired therapeutic agents, an economically viable preparation of the anti-succinate, which is practical for scale-up, is necessary. The present invention obviates the need for epimerization and tedious purification protocols. As a result, the production of these important compounds is more efficient and cost effective.

SUMMARY OF THE INVENTION

The present invention relates generally to processes for the preparation of compounds of the formula:

(III)

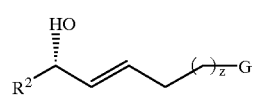

(IV)

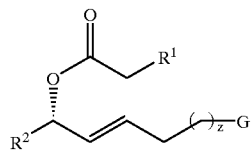

(IV-a)

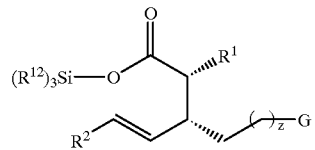

(V)

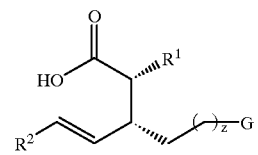

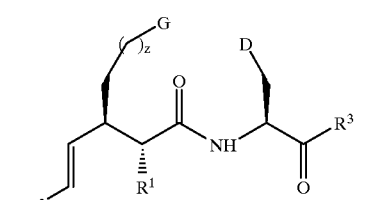
(VII)

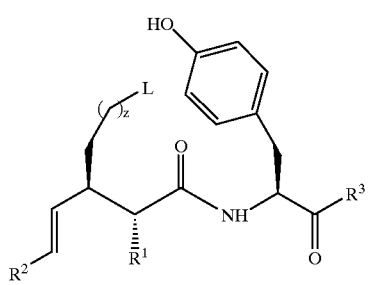
(VIII)

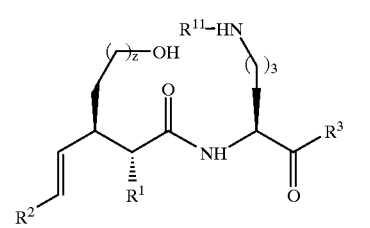
(VIII-a)

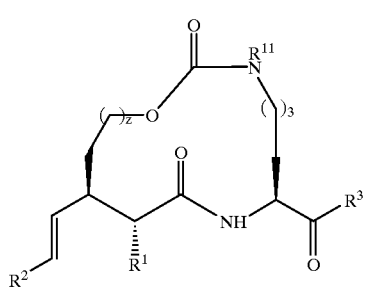
(IX-a)

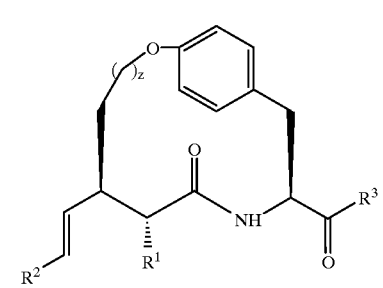
(IX)

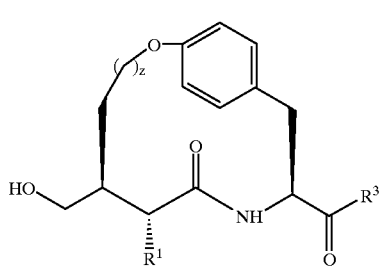
(X)

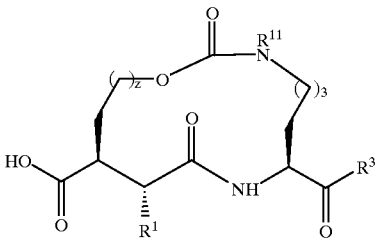
(X-a)

or salt forms thereof;
wherein:
D is para HO—$C_6H_4$— or $P^1$—$NR^{11}$—$CH_2CH_2CH_2$—;
G is a halogen or —OP;
P is a suitable oxygen protecting group;
$p^1$ is a suitable nitrogen protecting group;
L is a leaving group selected from the group consisting of: chlorine, bromine, iodine, mesylate and tosylate;
$R^1$ is selected from the group consisting of:
$C_{1-5}$ alkyl substituted with 0–5 $R^{1a}$, —$(CH_2)_r$—$C_{3-10}$ cycloalkyl substituted with 0–5 $R^{1a}$, and —$(CH_2)_r$-aryl substituted with 0–5 $R^{1a}$;
$R^{1a}$ is selected independently at each occurrence from the group consisting of:
hydrogen, —$CF_3$, —$CF_2CF_3$, —$NR^{1b}R^{1c}$, —$Si(R^{1d})_3$, $C_{1-5}$ alkyl, $C_{3-10}$ cycloalkyl, and aryl substituted with 0–5 $R^{1e}$;
$R^{1b}$ and $R^{1c}$ are selected independently at each occurrence from the group consisting of:
$C_{1-5}$ alkyl, $C_{3-5}$ cycloalkyl and phenyl;
$R^{1d}$ is selected independently at each occurrence from the group consisting of:
$C_{1-5}$ alkyl, $C_{1-5}$ haloalkyl, and aryl substituted with 0–5 $R^{1e}$;
$R^{1e}$ is selected independently at each occurrence from the group consisting of:
$C_{1-5}$ alkyl, —$(CH_2)_r$—$OR^{1f}$, —OH, halo, —$NH_2$, and —$(CF_2)_rCF_3$;
$R^{1f}$ is selected independently at each occurrence from the group consisting of:
$C_{1-5}$ alkyl, $C_{3-5}$ cycloalkyl and phenyl;
$R^2$ is selected from the group consisting of:
$C_{1-10}$ alkyl, $C_{3-10}$ cycloalkyl, and —$(CH_2)_r$-phenyl substituted with 0–3 $R^{2a}$;
$R^{2a}$ is selected independently at each occurrence from the group consisting of:
$C_{1-5}$ alkyl, —$(CH_2)_r$—$OR^{2b}$, —OH, halo, —$NH_2$, and —$(CF_2)_rCF_3$;
$R^{2b}$ is selected independently at each occurrence from the group consisting of:
$C_{1-5}$ alkyl, $C_{3-5}$ cycloalkyl and phenyl;
$R^3$ is selected from the group consisting of:
—$OR^4$, —$NR^5R^6$, —$NR^6(OR^5)$, $C_{1-5}$ alkyl substituted with 0–3 $R^{3a}$, —$(CH_2)_r$-aryl substituted with 0–5 $R^{3a}$, and —$(CH_2)_r$-heterocyclic substituted with 0–3 $R^{3a}$;
$R^{3a}$ is selected independently at each occurrence from the group consisting of:
hydrogen, $C_{1-5}$ alkyl, halo, hydroxy, —O—$(CH_2)_r$—$R^{3b}$, —$(CH_2)_r$—$C(O)R^{3b}$, —$(CH_2)_r$—$SO_2NHR^{3b}$, —$(CH_2)_r$—$C(O)NHR^{3b}$, —$(CH_2)_r$—$OC(O)R^{3b}$, —(CH$_2$)$_r$—NHSO$_2$R$^{3b}$, aryl, —(CH$_2$)$_r$—NHC(O) R$^{3b}$, and —(CH$_2$)$_r$—C(O)OR$^{3b}$;

R$^{3b}$ is selected independently at each occurrence from the group consisting of:
C$_{1-5}$ alkyl, C$_{3-5}$ cycloalkyl and phenyl;

R$^4$ is selected from the group consisting of:
hydrogen, C$_{1-10}$ alkyl, —(CH$_2$)$_r$—C$_{3-10}$ cycloalkyl, —(CH$_2$)$_r$-heterocyclic, and —(CH$_2$)$_r$-aryl substituted with 0–5 R$^{4a}$;

R$^{4a}$ is selected independently at each occurrence from the group consisting of:
C$_{1-5}$ alkyl, —(CH$_2$)$_r$—OR$^{4b}$, —OH, halo, —NH$_2$, and —(CF$_2$)$_r$CF$_3$;

R$^{4b}$ is selected independently at each occurrence from the group consisting of:
C$_{1-5}$ alkyl, C$_{3-5}$ cycloalkyl and phenyl;

R$^5$ is selected from the group consisting of:
C$_1$–C$_5$ alkyl, —(CH$_2$)$_r$—C$_3$–C$_{10}$ cycloalkyl, —(CHR$^{5a}$Y)$_n$—R$^9$, —(CR$^7$R$^8$)$_n$—O—C(R$^7$R$^8$)$_r$—R$^9$, —(CR$^7$R$^8$)$_r$—R$^9$, and —(CR$^7$R$^8$)$_r$CONR$^7$R$^8$;

R$^{5a}$ is selected independently at each occurrence from the group consisting of:
hydrogen, C$_{1-10}$ alkyl substituted with 0–3 R$^{5b}$, —(CH$_2$)$_r$-aryl substituted with 0–3 R$^{5b}$, and —(CH$_2$)$_r$—O—(CH$_2$)$_r$-aryl substituted with 0–3 R$^{5b}$;

R$^{5b}$ is selected independently at each occurrence from the group consisting of:
hydrogen, halo, hydroxy, —OR$^{5c}$, —NHC(O)CH$_3$, -aryl-(CH$_2$)$_r$—NH$_2$, -aryl-(CH$_2$)$_r$-aryl, C$_{1-10}$ alkyl substituted with 0–3 R$^{5d}$, and —(CH$_2$)$_r$-aryl substituted with 0–3 R$^{5d}$;

R$^{5c}$ is selected independently at each occurrence from the group consisting of:
C$_{1-5}$ alkyl, C$_{3-5}$ cycloalkyl and phenyl;

R$^{5d}$ is selected independently at each occurrence from the group consisting of;
hydrogen, C$_{1-5}$ alkyl, —O—(CH$_2$)$_r$—R$^{5e}$, —OH, halo, —NHC(O)CH$_3$, and —C(O)NH$_2$;

R$^{5e}$ is selected independently at each occurrence from the group consisting of:
C$_{1-5}$ alkyl, C$_{3-5}$ cycloalkyl and phenyl;

R$^6$ is selected from the group consisting of:
hydrogen, C$_1$–C$_{10}$ alkyl, —(CH$_2$)$_r$-aryl, —(CH$_2$)$_r$—C(O)R$^{6a}$, —(CH$_2$)$_r$-heterocyclic, and phenyl substituted with 0–5 R$^{6c}$;

R$^{6a}$ is selected independently at each occurrence from the group consisting of;
hydrogen, C$_{1-5}$ alkyl, —O—(CH$_2$)$_r$—R$^{6b}$, —OH, halo, —NHC(O)CH$_3$, and —C(O)NH$_2$;

R$^{6b}$ is selected independently at each occurrence from the group consisting of:
C$_{1-5}$ alkyl, C$_{3-5}$ cycloalkyl and phenyl;

R$^{6c}$ is selected independently at each occurrence from the group consisting of:
halogen, NO$_2$, —R$^{6d}$, and —O—(CH$_2$)$_r$—R$^{6d}$;

R$^{6d}$ is selected independently at each occurrence from the group consisting of:
C$_{1-5}$ alkyl, C$_{3-5}$ cycloalkyl and phenyl;

Alternatively, R$^5$ and R$^6$ combine to form a 3 to 8 membered heterocyclic ring containing 1 to 3 additional heteroatoms selected from —O—, —NR$^6$—, —S(O)p—, and —C(O)—, optionally fused to a phenyl ring;

R$^7$ and R$^8$ may be H or R$^{5a}$;

Alternatively, R$^7$ and R$^8$ combine to form 3 to 7 membered heterocyclic ring substituted with 1–3 R$^{7a}$, containing 1–3 additional heteroatoms selected from —O—, —S(O)p-, and —NR$^6$—, optionally fused to an aryl ring substituted with 0–3 R$^{7c}$;

R$^{7a}$ is selected independently at each occurrence from the group consisting of:
hydrogen, C$_{1-5}$ alkyl, C$_{3-5}$ cycloalkyl, hydroxy, halo, —OR$^{7b}$, —NHC(O)CH$_3$, —C(O)NH$_2$, and aryl;

R$^{7b}$ is selected independently at each occurrence from the group consisting of:
C$_{1-5}$ alkyl, C$_{1-5}$ cycloalkyl and phenyl;

R$^{7c}$ is selected independently at each occurrence from the group consisting of;
hydrogen, C$_{1-5}$ alkyl, C$_{3-5}$ cycloalkyl, hydroxy, halo, —O(CH$_2$)$_r$—R$^{7d}$, —NHC(O)CH$_3$, —C(O)NH$_2$, and aryl;

R$^{7d}$ is selected independently at each occurrence from the group consisting of:
C$_{1-5}$ alkyl, C$_{1-5}$ cycloalkyl and phenyl;

R$^9$ is selected from the group consisting of:
hydrogen, C$_{1-5}$ alkyl, —C(O)OC$_{1-5}$ alkyl, —(CH$_2$)$_r$-aryl substituted with 0–3 R$^{9a}$, and a 5 or 6 membered heterocyclic ring containing from 0 to 2 N, O or S(O)p, and substituted with 0–3 R$^{9a}$;

R$^{9a}$ is selected from the group consisting of:
—OH, —O—(CH$_2$)$_r$—R$^{9b}$, —C(O)OR$^{9b}$, —NHR$^{10}$ and aryl;

R$^{9b}$ is selected from the group consisting of:
C$_{1-5}$ alkyl, C$_{1-5}$ cycloalkyl and phenyl;

R$^{10}$ is independently at each occurrence H or C$_{1-10}$ alkyl substituted with 0–3 R$^{10a}$;

R$^{10a}$ is selected independently at each occurrence from the group consisting of:
hydrogen, C$_{1-10}$ alkyl substituted with 0–3 R$^{10b}$, and —(CH$_2$)$_r$-aryl substituted with 0–3 R$^{10b}$;

R$^{10b}$ is selected independently at each occurrence from the group consisting of:
hydrogen, halo, hydroxy, —OR$^{10c}$, —NHC(O)CH$_3$, —(CH$_2$)$_r$—C(O)NH$_2$, -aryl-NH$_2$, and —SO$_2$NH$_2$;

R$^{10c}$ is selected independently at each occurrence from the group consisting of:
C$_{1-5}$ alkyl, C$_{1-5}$ cycloalkyl and phenyl;

R$^{11}$ is selected independently at each occurrence from the group consisting of:
hydrogen, C$_1$–C$_{10}$ alkyl substituted with 0–3 R$^{11a}$; and —(CH$_2$)$_r$-aryl substituted with 0–3 R$^{11a}$;

R$^{11a}$ is selected independently at each occurrence from the group consisting of:
hydrogen, halo, hydroxy, —OR$^{11b}$, —NHC(O)CH$_3$, —(CH$_2$)$_r$—C(O)NH$_2$, -aryl-NH$_2$, and —SO$_2$NH$_2$;

R$^{11b}$ is selected independently at each occurrence from the group consisting of:
C$_{1-5}$ alkyl, C$_{1-5}$ cycloalkyl and phenyl;

n is selected from 1, 2 and 3;

p is selected independently at each occurrence from 0, 1 and 2;

r is selected independently at each occurrence from 0, 1, 2, and 3;

Y is selected from the group consisting of:
—CONR$^{10}$—, —NR$^{10}$CO—, —SO$_2$NR$^{10}$—, —NR$^{10}$SO$_2$—, and a 5 membered heterocyclic ring; and z is selected from 1, 2, 3, 4 and 5;
the process comprising:
(1) reducing of a compound of formula (II):

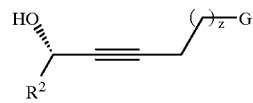

(II)

to form a compound of formula (III);
(2) acylating the compound of formula (III) to form a compound of formula (IV);
(3) contacting the compound of formula (IV) with a silylating agent in the presence of a suitable base, to form a compound of formula (IV-a), followed by treatment with hydroxide to form a compound of formula (V);
(4) coupling the compound of formula (V) with a compound of formula (VI):

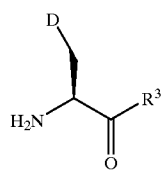

(VI)

to form a compound of formula (VII);
(5) deprotecting or activating, if necessary, the compound of formula (VII) to form a compound of formula (VIII) or (VIII-a);
(6) cyclizing a compound of formula (VIII) or (VIII-a) to form a compound of formula (IX) or (IX-a); and
(7) contacting the compound of formula (IX) or (IX-a) with a suitable oxidizing agent to form a compound of the formula (X) or (X-a).

DETAILED DESCRIPTION OF THE INVENTION

In a first embodiment, the present invention describes a process for the preparation of compounds of formula (VII):

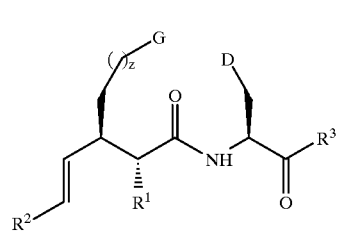

(VII)

or a form thereof;
wherein:
D is para HO—$C_6H_4$— or $P^1$—$NR^{11}$—$CH_2CH_2CH_2$—;
G is a halogen or —OP;
—P is a suitable oxygen protecting group;
$P^1$ is a suitable nitrogen protecting group;
$R^1$ is selected from the group consisting of:
  $C_{1-5}$ alkyl substituted with 0–5 $R^{1a}$,
  —$(CH_2)_r$—$C_{3-10}$ cycloalkyl substituted with 0–5 $R^{1a}$, and —$(CH_2)_r$-aryl substituted with 0–5 $R^{1a}$;

$R^{1a}$ is selected independently at each occurrence from the group consisting of:
  hydrogen, —$CF_3$, —$CF_2CF_3$, —$NR^{1b}R^{1c}$, —$Si(R^{1d})_3$, $C_{1-5}$ alkyl, $C_{3-10}$ cycloalkyl, and aryl substituted with 0–5 $R^{1e}$;
$R^{1b}$ and $R^{1c}$ are selected independently at each occurrence from the group consisting of:
  $C_{1-5}$ alkyl, $C_{3-5}$ cycloalkyl and phenyl;
$R^{1d}$ is selected independently at each occurrence from the group consisting of:
  $C_{1-5}$ alkyl, $C_{1-5}$ haloalkyl, and aryl substituted with 0–5 $R^{1e}$;
$R^{1e}$ is selected independently at each occurrence from the group consisting of:
  $C_{1-5}$ alkyl, —$(CH_2)_r$—$OR^{1f}$, —OH, halo, —$NH_2$, and —$(CF_2)_rCF_3$;
$R^{1f}$ is selected independently at each occurrence from the group consisting of:
  $C_{1-5}$ alkyl, $C_{3-5}$ cycloalkyl and phenyl;
$R^2$ is selected from the group consisting of:
  $C_{1-10}$ alkyl, $C_{3-10}$ cycloalkyl, and —$(CH_2)_r$-phenyl substituted with 0–3 $R^{2a}$;
$R^{2a}$ is selected independently at each occurrence from the group consisting of:
  $C_{1-5}$ alkyl, —$(CH_2)_r$—$OR^{2b}$, —OH, halo, —$NH_2$, and —$(CF_2)_rCF_3$;
$R^{2b}$ is selected independently at each occurrence from the group consisting of:
  $C_{1-5}$ alkyl, $C_{3-5}$ cycloalkyl and phenyl;
$R^3$ is selected from the group consisting of:
  —$OR^4$, —$NR^5R^6$, —$NR^6(OR^5)$, $C_{1-5}$ alkyl substituted with 0–3 $R^{3a}$, —$(CH_2)_r$-aryl substituted with 0–5 $R^{3a}$, and —$(CH_2)_r$-heterocyclic substituted with 0–3 $R^{3a}$;
$R^{3a}$ is selected independently at each occurrence from the group consisting of:
  hydrogen, $C_{1-5}$ alkyl, halo, hydroxy, —O—$(CH_2)_r$—$R^{3b}$, —$(CH_2)_r$—$C(O)R^{3b}$, —$(CH_2)_r$—$SO_2NHR^{3b}$, —$(CH_2)_r$—$C(O)NHR^{3b}$, —$(CH_2)_r$—$OC(O)R^{3b}$, —$(CH_2)_r$—$NHSO_2R^{3b}$, aryl, —$(CH_2)_r$—$NHC(O)R^{3b}$, and —$(CH_2)_r$—$C(O)OR^{3b}$;
$R^{3b}$ is selected independently at each occurrence from the group consisting of:
  $C_{1-5}$ alkyl, $C_{3-5}$ cycloalkyl and phenyl;
$R^4$ is selected from the group consisting of:
  hydrogen, $C_{1-10}$ alkyl, —$(CH_2)_r$—$C_{3-10}$ cycloalkyl, —$(CH_2)_r$-heterocyclic, and —$(CH_2)_r$-aryl substituted with 0–5 $R^{4a}$;
$R^{4a}$ is selected independently at each occurrence from the group consisting of:
  $C_{1-5}$ alkyl, —$(CH_2)_r$—$OR^{4b}$, —OH, halo, —$NH_2$, and —$(CF_2)_rCF_3$;
$R^{4b}$ is selected independently at each occurrence from the group consisting of:
  $C_{1-5}$ alkyl, $C_{3-5}$ cycloalkyl and phenyl;
$R^5$ is selected from the group consisting of:
  $C_1$-$C_5$ alkyl, —$(CH_2)_r$—$C_3$-$C_{10}$ cycloalkyl, —$(CHR^{5a}Y)_n$—$R^9$, —$(CR^7R^8)_n$—O—$C(R^7R^8)_r$—$R^9$, —$(CR^7R^8)_r$—$R^9$, and —$(CR^7R^8)_r$$CONR^7R^8$;
$R^{5a}$ is selected independently at each occurrence from the group consisting of:
  hydrogen, $C_{1-10}$ alkyl substituted with 0–3 $R^{5b}$, —$(CH_2)_r$-aryl substituted with 0–3 $R^{5b}$, and —$(CH_2)_r$—O—$(CH_2)_r$-aryl substituted with 0–3 $R^{5b}$;

$R^{5b}$ is selected independently at each occurrence from the group consisting of:
hydrogen, halo, hydroxy, —$OR^{5c}$, —$NHC(O)CH_3$, -aryl-$(CH_2)_r$—$NH_2$, -aryl-$(CH_2)_r$-aryl, $C_{1-10}$ alkyl substituted with 0–3 $R^{5d}$, and —$(CH_2)_r$-aryl substituted with 0–3 $R^{5d}$;

$R^{5c}$ is selected independently at each occurrence from the group consisting of:
$C_{1-5}$ alkyl, $C_{3-5}$ cycloalkyl and phenyl;

$R^{5d}$ is selected independently at each occurrence from the group consisting of;
hydrogen, $C_{1-5}$ alkyl, —O—$(CH_2)_r$—$R^{5e}$, —OH, halo, —$NHC(O)CH_3$, and —$C(O)NH_2$;

$R^{5e}$ is selected independently at each occurrence from the group consisting of:
$C_{1-5}$ alkyl, $C_{3-5}$ cycloalkyl and phenyl;

$R^6$ is selected from the group consisting of:
hydrogen, $C_{1-10}$ alkyl, —$(CH_2)_r$-aryl, —$(CH_2)_r$—$C(O)R^{6a}$, —$(CH_2)_r$-heterocyclic and phenyl substituted with 0–5 $R^{6c}$;

$R^{6a}$ is selected independently at each occurrence from the group consisting of;
hydrogen, $C_{1-5}$ alkyl, —O—$(CH_2)_r$—$R^{6b}$, —OH, halo, —$NHC(O)CH_3$, and —$C(O)NH_2$;

$R^{6b}$ is selected independently at each occurrence from the group consisting of:
$C_{1-5}$ alkyl, $C_{3-5}$ cycloalkyl and phenyl;

$R^{6c}$ is selected independently at each occurrence from the group consisting of:
halogen, $NO_2$, —$R^{6d}$, and —O—$(CH_2)_r$—$R^{6d}$;

$R^{6d}$ is selected independently at each occurrence from the group consisting of:
$C_{1-5}$ alkyl, $C_{3-5}$ cycloalkyl and phenyl;

Alternatively, $R^5$ and $R^6$ combine to form a 3 to 8 membered heterocyclic ring containing 1 to 3 additional heteroatoms selected from —O—, —$NR^6$—, —S(O)p-, and —C(O)—, optionally fused to a phenyl ring;

$R^7$ and $R^8$ may be H or $R^{5a}$;

Alternatively, $R^7$ and $R^8$ combine to form 3 to 7 membered heterocyclic ring substituted with 1–3 $R^{7a}$, containing 1–3 additional heteroatoms selected from —O—, —S(O)p-, and —$NR^6$—, optionally fused to an aryl ring substituted with 0–3 $R^{7c}$;

$R^{7a}$ is selected independently at each occurrence from the group consisting of:
hydrogen, $C_{1-5}$ alkyl, $C_{3-5}$ cycloalkyl, hydroxy, halo, —$OR^{7b}$, —$NHC(O)CH_3$, —$C(O)NH_2$, and aryl;

$R^{7b}$ is selected independently at each occurrence from the group consisting of:
$C_{1-5}$ alkyl, $C_{1-5}$ cycloalkyl and phenyl;

$R^{7c}$ is selected independently at each occurrence from the group consisting of;
hydrogen, $C_{1-5}$ alkyl, $C_{3-5}$ cycloalkyl, hydroxy, halo, —$O(CH_2)_r$—$R^{7d}$, —$NHC(O)CH_3$, —$C(O)NH_2$, and aryl;

$R^{7d}$ is selected independently at each occurrence from the group consisting of:
$C_{1-5}$ alkyl, $C_{1-5}$ cycloalkyl and phenyl;

$R^9$ is selected from the group consisting of: hydrogen, $C_{1-5}$ alkyl, —$C(O)OC_{1-5}$ alkyl, —$(CH_2)_r$-aryl substituted with 0–3 $R^{9a}$, and a 5 or 6 membered heterocyclic ring containing from 0 to 2 N, O or S(O)p, and substituted with 0–3 $R^{9a}$;

$R^{9a}$ is selected from the group consisting of:
—OH, —O—$(CH_2)_r$—$R^{9b}$, —$C(O)OR^{9b}$, $NHR^{10}$ and aryl;

$R^{9b}$ is selected from the group consisting of:
$C_{1-5}$ alkyl, $C_{1-5}$ cycloalkyl and phenyl;

$R^{10}$ is independently at each occurrence H or $C_{1-10}$ alkyl substituted with 0–3 $R^{10a}$;

$R^{10a}$ is selected independently at each occurrence from the group consisting of:
hydrogen, $C_{1-10}$ alkyl substituted with 0–3 $R^{10b}$, and —$(CH_2)_r$-aryl substituted with 0–3 $R^{10b}$;

$R^{10b}$ is selected independently at each occurrence from the group consisting of:
hydrogen, halo, hydroxy, —$OR^{10c}$, —$NHC(O)CH_3$, —$(CH_2)_r$—$C(O)NH_2$, -aryl-$NH_2$, and —$SO_2NH_2$;

$R^{10c}$ is selected independently at each occurrence from the group consisting of:
$C_{1-5}$ alkyl, $C_{1-5}$ cycloalkyl and phenyl;

$R^{11}$ is selected independently at each occurrence from the group consisting of:
hydrogen, $C_1$–$C_{10}$ alkyl substituted with 0–3 $R^{11a}$, and —$(CH_2)_r$-aryl substituted with 0–3 $R^{11a}$;

$R^{11a}$ is selected independently at each occurrence from the group consisting of:
hydrogen, halo, hydroxy, —$OR^{11b}$, —$NHC(O)CH_3$, —$(CH_2)_r$—$C(O)NH_2$, -aryl-$NH_2$, and —$SO_2NH_2$;

$R^{11b}$ is selected independently at each occurrence from the group consisting of:
$C_{1-5}$ alkyl, $C_{1-5}$ cycloalkyl and phenyl;

n is selected from 1, 2 and 3;

p is selected independently at each occurrence from 0, 1 and 2;

r is selected independently at each occurrence from 0, 1, 2, and 3;

Y is selected from the group consisting of: —$CONR^{10}$—, —$NR^{10}CO$—, —$SO_2NR^{10}$—, —$NR^{10}SO_2$—, and a 5 membered heterocyclic ring; and z is selected from 1, 2, 3, 4 and 5;

the process comprising:
contacting a compound of the formula (IV):

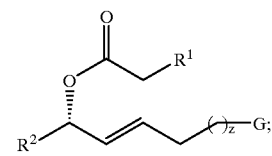

(IV)

wherein the double bond is in the E configuration; with a silylating agent in the presence of a strong base to give a compound of formula (IV-a):

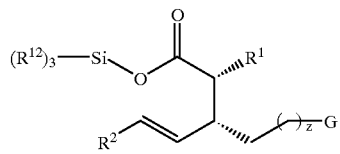

(IV-a)

wherein $R^{12}$ is selected independently at each occurrence from $C_{1-6}$ alkyl and phenyl;

contacting the compound of formula (IV-a) with hydroxide to form a compound of formula (V):

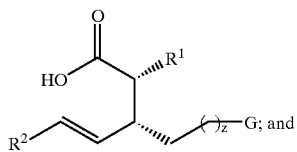

(V)

coupling the compound of formula (V) with a compound of formula (VI):

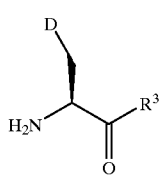

(VI)

to form a compound of formula (VII), or a salt form thereof.

In a preferred embodiment, the compound of formula (IV) is prepared by the process comprising:
reducing a compound of formula (II):

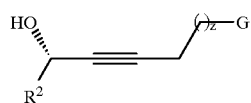

(II)

to form a compound of formula (III):

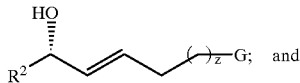

(III)

acylating the compound of formula (III) to form a compound of formula (IV).

In another preferred embodiment, P is tert-butyldimethylsilyl or methoxymethyl;
$P^1$ is tert-butyloxycarbonyl;
$R^1$ is $C_{1-5}$ alkyl;
$R^2$ is selected from the group consisting of:
    $C_{1-10}$ alkyl, $C_{3-10}$ cycloalkyl, and —$(CH_2)_r$-phenyl;
$R^3$ is —$OR^4$ or —$NR^5R^6$
$R^4$ is selected from the group consisting of:
    hydrogen, $C_{1-10}$ alkyl, —$(CH_2)_r$—$C_{3-10}$ cycloalkyl, and —$(CH_2)_r$-phenyl;
$R^5$ is selected from the group consisting of:
    $C_{1-5}$ alkyl, —$(CH_2)_r$—$C_{3-10}$ cycloalkyl, —$CH_2$—$CONHR^{10}$, —$CH_2$—$C(O)OC_{1-5}$ alkyl, —$CH_2$—$CONR^7R^8$, and —$(CH_2)_r$-phenyl;
$R^6$ is selected from hydrogen or $C_1$–$C_{10}$ alkyl;
$R^7$ and $R^8$ form a 6 membered saturated ring containing —O— or —$NR^6$—;
$R^{10}$ is H or $C_{1-5}$ alkyl;
$R^{11}$ is selected from the group consisting of:
    hydrogen, $C_1$–$C_{10}$ alkyl, and phenyl;
r is selected from 0, 1, or 2; and
z is 2.

In a more preferred embodiment, the silylating agent is trimethylsilylchloride or t-butyldimethylsilylchloride;
the strong base is lithium diisopropylamide or lithium hexamethyldisilazide; and
coupling comprises contacting a compound of formula (V) with a compound of formula (VI) in the presence of a coupling agent selected from the group consisting of:
    dicyclohexylcarbodiimide, carbonyldiimidazole, 1-(3-dimethylaminopropyl)-3-ethylcarbodiimide, O-(1H-benzotriazol-1-yl)-N,N,N',N'-tetra-methyluronium tetraflouroborate, benzotriazol-1-yl-oxy-tri-pyrrolidinophosphonium hexafluorophosphate and benzotriazol-1-yl-oxy-tris-dimethylamino-phosphonium hexafluorophosphate.

In an even more preferred embodiment,
$R^1$ is —$CH_2CH(CH_3)_2$;
$R^2$ is —$CH(CH_3)_2$;
$R^3$ is selected from the group consisting of:
    —$OC_{1-5}$ alkyl, —$NHCH_2C(O)OC_{1-5}$ alkyl, —$NHCH_2C(O)NR^7R^8$ and —$NHCH_2C(O)NHCH_3$; and
$R^7$ and $R^8$ are taken together to form a morpholine ring.

In a second embodiment, the present invention describes a process for the preparation of a compound of formula (X-a):

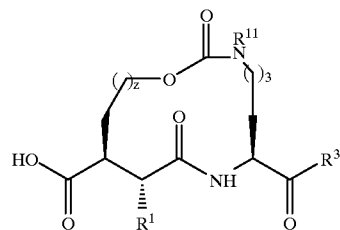

(X-a)

or a pharmaceutically acceptable salt form thereof,
wherein:
$R^1$ is selected from the group consisting of:
    $C_{1-5}$ alkyl substituted with 0–5 $R^{1a}$, —$(CH_2)_r$—$C_{3-10}$ cycloalkyl substituted with 0–5 $R^{1a}$, and —$(CH_2)_r$-aryl substituted with 0–5 $R^{1a}$;
$R^{1a}$ is selected independently at each occurrence from the group consisting of:
    hydrogen, —$CF_3$, —$CF_2CF_3$, —$NR^{1b}R^{1c}$, —$Si(R^{1d})_3$, $C_{1-5}$ alkyl, $C_{3-10}$ cycloalkyl, and aryl substituted with 0–5 $R^{1e}$;
$R^{1b}$ and $R^{1c}$ are selected independently at each occurrence from the group consisting of:
    $C_{1-5}$ alkyl, $C_{3-5}$ cycloalkyl and phenyl;
$R^{1d}$ is selected independently at each occurrence from the group consisting of:
    $C_{1-5}$ alkyl, $C_{1-5}$ haloalkyl, and aryl substituted with 0–5 $R^{1e}$;
$R^{1e}$ is selected independently at each occurrence from the group consisting of:
    $C_{1-5}$ alkyl, —$(CH_2)_r$—$OR^{1f}$, —OH, halo, —$NH_2$, and —$(CF_2)_rCF_3$;
$R^{1f}$ is selected independently at each occurrence from the group consisting of:
    $C_{1-5}$ alkyl, $C_{3-5}$ cycloalkyl and phenyl;
$R^3$ is selected from the group consisting of:
    —$OR^4$, —$NR^5R^6$, —$NR^6(OR^5)$, $C_{1-5}$ alkyl substituted with 0–3 $R^{3a}$, —$(CH_2)_r$-aryl substituted with 0–5 $R^{3a}$, and —$(CH_2)_r$-heterocyclic substituted with 0–3 $R^{3a}$;

$R^{3a}$ is selected independently at each occurrence from the group consisting of:
 hydrogen, $C_{1-5}$ alkyl, halo, hydroxy, —O—(CH$_2$)$_r$—$R^{3b}$, —(CH$_2$)$_r$—C(O)R$^{3b}$, —(CH$_2$)$_r$—SO$_2$NHR$^{3b}$, —(CH$_2$)$_r$—C(O)NHR$^{3b}$, —(CH$_2$)$_r$—OC(O)R$^{3b}$, —(CH$_2$)$_r$—NHSO$_2$R$^{3b}$, aryl, —(CH$_2$)$_r$—NHC(O)R$^{3b}$, and —(CH$_2$)$_r$—C(O)OR$^{3b}$;

$R^{3b}$ is selected independently at each occurrence from the group consisting of:
 $C_{1-5}$ alkyl, $C_{3-5}$ cycloalkyl and phenyl;

$R^4$ is selected from the group consisting of:
 hydrogen, $C_1$–$C_{10}$ alkyl, —(CH$_2$)$_r$—$C_{3-10}$ cycloalkyl, —(CH$_2$)$_r$-heterocyclic, and —(CH$_2$)$_r$-aryl substituted with 0–5 R$^{4a}$;

$R^{4a}$ is selected independently at each occurrence from the group consisting of:
 $C_{1-5}$ alkyl, —(CH$_2$)$_r$—OR$^{4b}$, —OH, halo, —NH$_2$, and —(CF$_2$)$_r$CF$_3$;

$R^{4b}$ is selected independently at each occurrence from the group consisting of:
 $C_{1-5}$ alkyl, $C_{3-5}$ cycloalkyl and phenyl;

$R^5$ is selected from the group consisting of:
 $C_1$–$C_5$ alkyl, —(CH$_2$)$_r$—$C_3$–$C_{10}$ cycloalkyl, —(CHR$^{5a}$Y)$_n$—R$^9$, —(CR$^7$R$^8$)$_n$—O—C(R$^7$R$^8$)$_r$—R$^9$, —(CR$^7$R$^8$)$_r$—R$^9$, and —(CR$^7$R$^8$)$_r$CONR$^7$R$^8$;

$R^{5a}$ is selected independently at each occurrence from the group consisting of:
 hydrogen, $C_{1-10}$ alkyl substituted with 0–3 R$^{5b}$, —(CH$_2$)$_r$-aryl substituted with 0–3 R$^{5b}$, and —(CH$_2$)$_r$—O—(CH$_2$)$_r$-aryl substituted with 0–3 R$^{5b}$;

$R^{5b}$ is selected independently at each occurrence from the group consisting of:
 hydrogen, halo, hydroxy, —OR$^{5c}$, —NHC(O)CH$_3$, -aryl-(CH$_2$)$_r$—NH$_2$, -aryl-(CH$_2$)$_r$-aryl, $C_{1-10}$ alkyl substituted with 0–3 R$^{5d}$, and —(CH$_2$)$_r$-aryl substituted with 0–3 R$^{5d}$;

$R^{5c}$ is selected independently at each occurrence from the group consisting of:
 $C_{1-5}$ alkyl, $C_{3-5}$ cycloalkyl and phenyl;

$R^{5d}$ is selected independently at each occurrence from the group consisting of;
 hydrogen, $C_{1-5}$ alkyl, —O—(CH$_2$)$_r$—R$^{5e}$, —OH, halo, —NHC(O)CH$_3$, and —C(O)NH$_2$;

$R^{5e}$ is selected independently at each occurrence from the group consisting of:
 $C_{1-5}$ alkyl, $C_{3-5}$ cycloalkyl and phenyl;

$R^6$ is selected from the group consisting of:
 hydrogen, $C_1$–$C_{10}$ alkyl, —(CH$_2$)$_r$-aryl, —(CH$_2$)$_r$—C(O)R$^{6a}$, —(CH$_2$)$_r$-heterocyclic and phenyl substituted with 0–5 R$^{6c}$;

$R^{6a}$ is selected independently at each occurrence from the group consisting of;
 hydrogen, $C_{1-5}$ alkyl, —O—(CH$_2$)$_r$—R$^{6b}$, —OH, halo, —NHC(O)CH$_3$, and —C(O)NH$_2$;

$R^{6b}$ is selected independently at each occurrence from the group consisting of:
 $C_{1-5}$ alkyl, $C_{3-5}$ cycloalkyl and phenyl;

$R^{6c}$ is selected independently at each occurrence from the group consisting of:
 halogen, NO$_2$, —R$^{6d}$, and —O—(CH$_2$)$_r$—R$^{6d}$;

$R^{6d}$ is selected independently at each occurrence from the group consisting of:
 $C_{1-5}$ alkyl, $C_{3-5}$ cycloalkyl and phenyl;

Alternatively, $R^5$ and $R^6$ combine to form a 3 to 8 membered heterocyclic ring containing 1 to 3 additional heteroatoms selected from —O—, —NR$^6$—, —S(O)p—, and —C(O)—, optionally fused to a phenyl ring;

$R^7$ and $R^8$ may be H or R$^{5a}$;

Alternatively, $R^7$ and $R^8$ combine to form 3 to 7 membered heterocyclic ring substituted with 1–3 R$^{7a}$, containing 1–3 additional heteroatoms selected from —O—, —S(O)p-, and —NR$^6$—, optionally fused to an aryl ring substituted with 0–3 R$^{7c}$;

$R^{7a}$ is selected independently at each occurrence from the group consisting of:
 hydrogen, $C_{1-5}$ alkyl, $C_{3-5}$ cycloalkyl, hydroxy, halo, —OR$^{7b}$, —NHC(O)CH$_3$, —C(O)NH$_2$, and aryl;

$R^{7b}$ is selected independently at each occurrence from the group consisting of:
 $C_{1-5}$ alkyl, $C_{1-5}$ cycloalkyl and phenyl;

$R^{7c}$ is selected independently at each occurrence from the group consisting of;
 hydrogen, $C_{1-5}$ alkyl, $C_{3-5}$ cycloalkyl, hydroxy, halo, —O(CH$_2$)$_r$—R$^{7d}$, —NHC(O)CH$_3$, —C(O)NH$_2$, and aryl;

$R^{7d}$ is selected independently at each occurrence from the group consisting of:
 $C_{1-5}$ alkyl, $C_{1-5}$ cycloalkyl and phenyl;

$R^9$ is selected from the group consisting of: hydrogen, $C_{1-5}$ alkyl, —C(O)OC$_{1-5}$ alkyl, —(CH$_2$)$_r$-aryl substituted with 0–3 R$^{9a}$, and a 5 or 6 membered heterocyclic ring containing from 0 to 2 N, O or S(O)p, and substituted with 0–3 R$^{9a}$;

$R^{9a}$ is selected from the group consisting of:
 —OH, —O—(CH$_2$)$_r$—R$^{9b}$, —C(O)OR$^{9b}$, NHR$^{10}$ and aryl;

$R^{9b}$ is selected from the group consisting of:
 $C_{1-5}$ alkyl, $C_{1-5}$ cycloalkyl and phenyl;

$R^{10}$ is independently at each occurrence H or $C_{1-10}$ alkyl substituted with 0–3 R$^{10a}$;

$R^{10a}$ is selected independently at each occurrence from the group consisting of:
 hydrogen, $C_1$–$C_{10}$ alkyl substituted with 0–3 R$^{10b}$, and —(CH$_2$)$_r$-aryl substituted with 0–3 R$^{10b}$;

$R^{10b}$ is selected independently at each occurrence from the group consisting of:
 hydrogen, halo, hydroxy, —OR$^{10c}$, —NHC(O)CH$_3$, —(CH$_2$)$_r$—C(O)NH$_2$, -aryl-NH$_2$, and —SO$_2$NH$_2$;

$R^{10c}$ is selected independently at each occurrence from the group consisting of:
 $C_{1-5}$ alkyl, $C_{1-5}$ cycloalkyl and phenyl;

$R^{11}$ is selected independently at each occurrence from the group consisting of:
 hydrogen, $C_1$–$C_{10}$ alkyl substituted with 0–3 R$^{11a}$, and —(CH$_2$)$_r$-aryl substituted with 0–3 R$^{11a}$;

$R^{11a}$ is selected independently at each occurrence from the group consisting of:
 hydrogen, halo, hydroxy, —OR$^{11b}$, —NHC(O)CH$_3$, —(CH$_2$)$_r$—C(O)NH$_2$, -aryl-NH$_2$, and —SO$_2$NH$_2$;

$R^{11b}$ is selected independently at each occurrence from the group consisting of:
 $C_{1-5}$ alkyl, $C_{1-5}$ cycloalkyl and phenyl;

n is selected from 1, 2 and 3;

p is selected independently at each occurrence from 0, 1 and 2;

r is selected independently at each occurrence from 0, 1, 2, and 3;

Y is selected from the group consisting of:
—CONR$^{10}$—, —NR$^{10}$CO—, —SO$_2$NR$^{10}$—, —NR$^{10}$SO$_2$—, and a 5- membered heterocyclic ring; and z is selected from 1, 2, 3, 4 and 5;
the process comprising:
cyclizing a compound of formula (VIII-a):

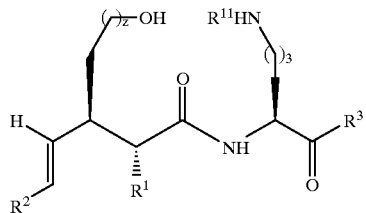

(VIII-a)

or an acceptable salt form thereof;
wherein:
R$^2$ is selected from the group consisting of:
C$_{1-10}$ alkyl, C$_{3-10}$ cycloalkyl, and —(CH$_2$)$_r$-phenyl substituted with 0–3 R$^{2a}$;

R$^{2a}$ is selected independently at each occurrence from the group consisting of:
C$_{1-5}$ alkyl, —(CH$_2$)$_r$—OR$^{2b}$, —OH, halo, —NH$_2$, and —(CF$_2$)$_r$CF$_3$;

R$^{2b}$ is selected independently at each occurrence from the group consisting of:
C$_{1-5}$ alkyl, C$_{3-5}$ cycloalkyl and phenyl;
to form a compound of formula (IX-a):

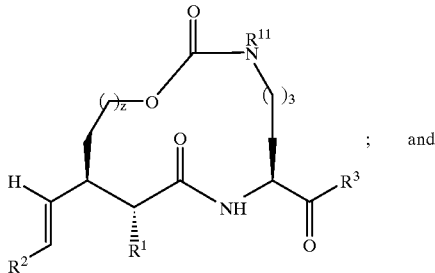

(IX-a)

; and contacting the compound of formula (IX-a) with an oxidizing agent to form a compound of formula (X-a) or a pharmaceutically acceptable salt form thereof.

In a preferred embodiment, R$^1$ is C$_{1-5}$ alkyl;
R$^2$ is selected from the group consisting of:
C$_{1-10}$ alkyl, C$_{3-10}$ cycloalkyl, and —(CH$_2$)$_r$-phenyl;
R$^3$ is —OR$^4$ or —NR$^5$R$^6$
R$^4$ is selected from the group consisting of:
hydrogen, C$_{1-10}$ alkyl, —(CH$_2$)$_r$—C$_{3-10}$ cycloalkyl, and —(CH$_2$)$_r$-phenyl;
R$^5$ is selected from the group consisting of:
C$_{1-5}$ alkyl, —(CH$_2$)$_r$—C$_{3-10}$ cycloalkyl, —CH$_2$—CONHR$^{10}$, —CH$_2$—C(O)OC$_{1-5}$ alkyl, —CH$_2$—CONR$^7$R$^8$, and —(CH$_2$)$_r$-phenyl;
R$^6$ is selected from hydrogen or C$_1$–C$_{10}$ alkyl;
R$^7$ and R$^8$ form a 6 membered saturated ring containing —O— or —NR$^6$—;
R$^{10}$ is H or C$_{1-5}$ alkyl;

R$^{11}$ is selected from the group consisting of:
hydrogen, C$_1$–C$_{10}$ alkyl, and phenyl;
r is selected from 0, 1, or 2;
z is 2;
cyclizing comprises contacting the free base of the compound of formula (XII-a) with phosgene or an equivalent thereof in the presence of an acid scavenger; and
the oxidizing agent is KMnO$_4$ in NaIO$_4$ or ozone.

In a more preferred embodiment, R$^1$ is —CH$_2$CH(CH$_3$)$_2$;
R$^2$ is —CH(CH$_3$)$_2$;
R$^3$ is selected from the group consisting of:
—OC$_{1-5}$ alkyl, —NHCH$_2$C(O)OC$_{1-5}$ alkyl, —NHCH$_2$C(O)NR$^7$R$^8$ and —NHCH$_2$C(O)NHCH$_3$; and R$^7$ and R$^8$ are taken together to form a morpholine ring;
cyclizing comprises contacting the free base of the compound of formula (XII-a) with phosgene or an equivalent thereof in the presence of an acid scavenger selected from the group consisting of:
triethylamine, diisopropylamine, and pyridine; and the oxidizing agent is ozone.

In an even more preferred embodiment, R$^3$ is —OCH$_3$.

In a third embodiment, the present invention describes a process for the preparation of a compound of formula (X):

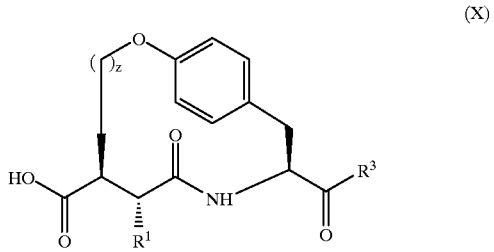

(X)

or a pharmaceutically acceptable salt form thereof;
wherein:
R$^1$ is selected from the group consisting of:
C$_{1-5}$ alkyl substituted with 0–5 R$^{1a}$, —(CH$_2$)$_r$—C$_{3-10}$ cycloalkyl substituted with 0–5 R$^{1a}$, and —(CH$_2$)$_r$-aryl substituted with 0–5 R$^{1a}$;

R$^{1a}$ is selected independently at each occurrence from the group consisting of:
hydrogen, —CF$_3$, —CF$_2$CF$_3$, —NR$^{1b}$R$^{1c}$, —Si(R$^{1d}$)$_3$, C$_{1-5}$ alkyl, C$_{3-10}$ cycloalkyl, and aryl substituted with 0–5 R$^{1e}$;

R$^{1b}$ and R$^{1c}$ are selected independently at each occurrence from the group consisting of:
C$_{1-5}$ alkyl, C$_{3-5}$ cycloalkyl and phenyl;

R$^{1d}$ is selected independently at each occurrence from the group consisting of:
C$_{1-5}$ alkyl, C$_{1-5}$ haloalkyl, and aryl substituted with 0–5 R$^{1e}$;

R$^{1e}$ is selected independently at each occurrence from the group consisting of:
C$_{1-5}$ alkyl, —(CH$_2$)$_r$—OR$^{1f}$, —OH, halo, —NH$_2$, and —(CF$_2$)$_r$CF$_3$;

R$^{1f}$ is selected independently at each occurrence from the group consisting of:
C$_{1-5}$ alkyl, C$_{3-5}$ cycloalkyl and phenyl;

R$^3$ is selected from the group consisting of:
—OR$^4$, —NR$^5$R$^6$, —NR$^6$(OR$^5$), C$_{1-5}$ alkyl substituted with 0–3 R$^{3a}$, —(CH$_2$)$_r$-aryl substituted with 0–5 R$^{3a}$, and —(CH$_2$)$_r$-heterocyclic substituted with 0–3 R$^{3a}$;

$R^{3a}$ is selected independently at each occurrence from the group consisting of:
hydrogen, $C_{1-5}$ alkyl, halo, hydroxy, —O—$(CH_2)_r$—$R^{3b}$, —$(CH_2)_r$—$C(O)R^{3b}$, —$(CH_2)_r$—$SO_2NHR^{3b}$, —$(CH_2)_r$—$C(O)NHR^{3b}$, —$(CH_2)_r$—$OC(O)R^{3b}$, —$(CH_2)_r$—$NHSO_2R^{3b}$, aryl, —$(CH_2)_r$—$NHC(O)R^{3b}$, and —$(CH_2)_r$—$C(O)OR^{3b}$;

$R^{3b}$ is selected independently at each occurrence from the group consisting of:
$C_{1-5}$ alkyl, $C_{3-5}$ cycloalkyl and phenyl;

$R^4$ is selected from the group consisting of:
hydrogen, $C_1$–$C_{10}$ alkyl, —$(CH_2)_r$—$C_{3-10}$ cycloalkyl, —$(CH_2)_r$-heterocyclic, and —$(CH_2)_r$-aryl substituted with 0–5 $R^{4a}$;

$R^{4a}$ is selected independently at each occurrence from the group consisting of:
$C_{1-5}$ alkyl, —$(CH_2)_r$—$OR^{4b}$, —OH, halo, —$NH_2$, and —$(CF_2)_rCF_3$;

$R^{4b}$ is selected independently at each occurrence from the group consisting of:
$C_{1-5}$ alkyl, $C_{3-5}$ cycloalkyl and phenyl;

$R^5$ is selected from the group consisting of:
$C_1$–$C_5$ alkyl, —$(CH_2)_r$—$C_3$–$C_{10}$ cycloalkyl, —$(CHR^{5a}Y)_n$—$R^9$, —$(CR^7R^8)_n$—O—$C(R^7R^8)_r$—$R^9$, —$(CR^7R^8)_r$—$R^9$, and —$(CR^7R^8)_rCONR^7R^8$;

$R^{5a}$ is selected independently at each occurrence from the group consisting of:
hydrogen, $C_{1-10}$ alkyl substituted with 0–3 $R^{5b}$, —$(CH_2)_r$-aryl substituted with 0–3 $R^{5b}$, and —$(CH_2)_r$—O—$(CH_2)_r$-aryl substituted with 0–3 $R^{5b}$;

$R^{5b}$ is selected independently at each occurrence from the group consisting of:
hydrogen, halo, hydroxy, —$OR^{5c}$, —$NHC(O)CH_3$, -aryl-$(CH_2)_r$—$NH_2$, -aryl-$(CH_2)_r$-aryl, $C_{1-10}$ alkyl substituted with 0–3 $R^{5d}$, and —$(CH_2)_r$-aryl substituted with 0–3 $R^{5d}$;

$R^{5c}$ is selected independently at each occurrence from the group consisting of:
$C_{1-5}$ alkyl, $C_{3-5}$ cycloalkyl and phenyl;

$R^{5d}$ is selected independently at each occurrence from the group consisting of;
hydrogen, $C_{1-5}$ alkyl, —O—$(CH_2)_r$—$R^{5e}$, —OH, halo, —$NHC(O)CH_3$, and —$C(O)NH_2$;

$R^{5e}$ is selected independently at each occurrence from the group consisting of:
$C_{1-5}$ alkyl, $C_{3-5}$ cycloalkyl and phenyl;

$R^6$ is selected from the group consisting of:
hydrogen, $C_1$–$C_{10}$ alkyl, —$(CH_2)_r$-aryl, —$(CH_2)_r$—$C(O)R^{6a}$, —$(CH_2)_r$-heterocyclic and phenyl substituted with 0–5 $R^{6c}$;

$R^{6a}$ is selected independently at each occurrence from the group consisting of;
hydrogen, $C_{1-5}$ alkyl, —O—$(CH_2)_r$—$R^{6b}$, —OH, halo, —$NHC(O)CH_3$, and —$C(O)NH_2$;

$R^{6b}$ is selected independently at each occurrence from the group consisting of:
$C_{1-5}$ alkyl, $C_{3-5}$ cycloalkyl and phenyl;

$R^{6c}$ is selected independently at each occurrence from the group consisting of:
halogen, $NO_2$, —$R^{6d}$, and —O—$(CH_2)_r$—$R^{6d}$;

$R^{6d}$ is selected independently at each occurrence from the group consisting of:
$C_{1-5}$ alkyl, $C_{3-5}$ cycloalkyl and phenyl;

Alternatively, $R^5$ and $R^6$ combine to form a 3 to 8 membered heterocyclic ring containing 1 to 3 additional heteroatoms selected from —O—, —$NR^6$—, —$S(O)p$-, and —$C(O)$—, optionally fused to a phenyl ring;

$R^7$ and $R^8$ may be H or $R^{5a}$;

Alternatively, $R^7$ and $R^8$ combine to form 3 to 7 membered heterocyclic ring substituted with 1–3 $R^{7a}$, containing 1–3 additional heteroatoms selected from —O—, —$S(O)p$-, and —$NR^6$—, optionally fused to an aryl ring substituted with 0–3 $R^{7c}$;

$R^{7a}$ is selected independently at each occurrence from the group consisiting of:
hydrogen, $C_{1-5}$ alkyl, $C_{3-5}$ cycloalkyl, hydroxy, halo, —$OR^{7b}$, —$NHC(O)CH_3$, —$C(O)NH_2$, and aryl;

$R^{7b}$ is selected independently at each occurrence from the group consisting of:
$C_{1-5}$ alkyl, $C_{1-5}$ cycloalkyl and phenyl;

$R^{7c}$ is selected independently at each occurrence from the group consisting of;
hydrogen, $C_{1-5}$ alkyl, $C_{3-5}$ cycloalkyl, hydroxy, halo, —$O(CH_2)_r$—$R^{7d}$, —$NHC(O)CH_3$, —$C(O)NH_2$, and aryl;

$R^{7d}$ is selected independently at each occurrence from the group consisting of:
$C_{1-5}$ alkyl, $C_{1-5}$ cycloalkyl and phenyl;

$R^9$ is selected from the group consisting of: hydrogen, $C_{1-5}$ alkyl, —$C(O)OC_{1-5}$ alkyl, —$(CH_2)_r$-aryl substituted with 0–3 $R^{9a}$, and a 5 or 6 membered heterocyclic ring containing from 0 to 2 N, O or $S(O)p$, and substituted with 0–3 $R^{9a}$;

$R^{9a}$ is selected from the group consisting of:
—OH, —O—$(CH_2)_r$—$R^{9b}$, —$C(O)OR^{9b}$, $NHR^{10}$ and aryl;

$R^{9b}$ is selected from the group consisting of:
$C_{1-5}$ alkyl, $C_{1-5}$ cycloalkyl and phenyl;

$R^{10}$ is independently at each occurrence H or $C_{1-10}$ alkyl substituted with 0–3 $R^{10a}$;

$R^{10a}$ is selected independently at each occurrence from the group consisting of:
hydrogen, $C_1$–$C_{10}$ alkyl substituted with 0–3 $R^{10b}$, and —$(CH_2)_r$-aryl substituted with 0–3 $R^{10b}$;

$R^{10b}$ is selected independently at each occurrence from the group consisting of:
hydrogen, halo, hydroxy, —$OR^{10c}$, —$NHC(O)CH_3$, —$(CH_2)_r$—$C(O)NH_2$, -aryl-$NH_2$, and —$SO_2NH_2$;

$R^{10c}$ is selected independently at each occurrence from the group consisting of:
$C_{1-5}$ alkyl, $C_{1-5}$ cycloalkyl and phenyl;

n is selected from 1, 2 and 3;

p is selected independently at each occurrence from 0, 1 and 2;

r is selected independently at each occurrence from 0, 1, 2, and 3;

Y is selected from the group consisting of:
—$CONR^{10}$—, —$NR^{10}CO$—, —$SO_2NR^{10}$—, —$NR^{10}SO_2$—, and a 5 membered heterocyclic ring; and z is selected from 1, 2, 3, 4 and 5;
the process comprising:
cyclizing a compound of formula (VIII):

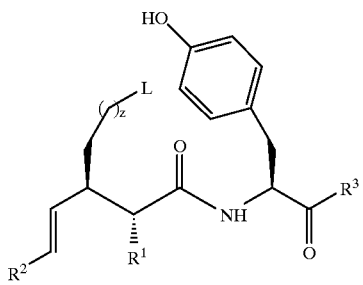

(VIII)

wherein:
L is a leaving group;
$R^2$ is selected from the group consisting of:
  $C_{1-10}$ alkyl, $C_{3-10}$ cycloalkyl, and —$(CH_2)_r$-phenyl substituted with 0–3 $R^{2a}$;
$R^{2a}$ is selected independently at each occurrence from the group consisting of:
  $C_{1-5}$ alkyl, —$(CH_2)_r$—$OR^{2b}$, —OH, halo, —$NH_2$, and —$(CF_2)_rCF_3$;
$R^{2b}$ is selected independently at each occurrence from the group consisting of:
  $C_{1-5}$ alkyl, $C_{3-5}$ cycloalkyl and phenyl;
to give a compound of formula (IX):

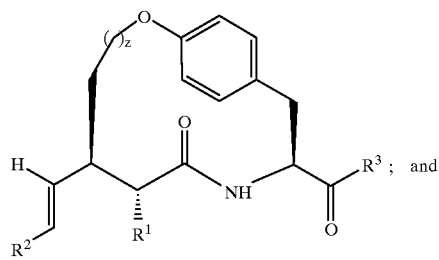

(IX)

contacting the compound of formula (IX) with an oxidizing agent to give a compound of formula (X),
or a pharmaceutically acceptable salt form thereof.
In a preferred embodiment, $R^1$ is $C_{1-5}$ alkyl;
$R^2$ is selected from the group consisting of:
  $C_{1-10}$ alkyl, $C_{3-10}$ cycloalkyl, and —$(CH_2)_r$-phenyl;
$R^3$ is —$OR^4$ or —$NR^5R^6$
$R^4$ is selected from the group consisting of:
  hydrogen, $C_{1-10}$ alkyl, —$(CH_2)_r$—$C_{3-10}$ cycloalkyl, and —$(CH_2)_r$-phenyl;
$R^5$ is selected from the group consisting of:
  $C_{1-5}$ alkyl, —$(CH_2)_r$—$C_{3-10}$ cycloalkyl, —$CH_2$—$CONHR^{10}$, —$CH_2$—$C(O)OC_{1-5}$ alkyl, —$CH_2$—$CONR^7R^8$, and —$(CH_2)_r$-phenyl;
$R^6$ is selected from hydrogen or $C_{1-10}$ alkyl;
$R^7$ and $R^8$ form a 6 membered saturated ring containing —O— or —$NR^6$—;
$R^{10}$ is H or $C_{1-5}$ alkyl;
r is selected from 0, 1, or 2;
z is 2;
the leaving group is selected from the group consisting of: chlorine, bromine, iodine, mesylate and tosylate;
cyclizing comprises contacting a compound of formula (VIII) with a suitable base in a suitable solvent at a suitable temperature; and
the oxidizing agent is $KMnO_4$ in $NaIO_4$ or ozone.
In a more preferred embodiment, $R^1$ is —$CH_2CH(CH_3)_2$;
$R^2$ is —$CH(CH_3)_2$; and,
$R^3$ is selected from the group consisting of:
  —$OC_{1-5}$ alkyl, —$NHCH_2C(O)OC_{1-5}$ alkyl, —$NHCH_2C(O)NR^7R^8$ and —$NHCH_2C(O)NHCH_3$; and $R^7$ and $R^8$ are taken together to form a morpholine ring;
the leaving group is bromine;
cyclizing comprises contacting the free base of a compound of formula (VIII) with cesium carbonate in dimethyl formamide and dimethylsulfoxide at about 70° C. to about 90° C.; and
the oxidizing agent is ozone.
In an even more preferred embodiment, $R^3$ is —$OCH_3$.
In a fourth embodiment, the present invention describes a compound of formula (III):

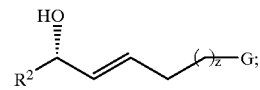

(III)

wherein:
$R^2$ is —$CH(CH_3)_2$;
G is —$OCH_2OCH_3$; and
z is 2.
In a fifth embodiment, the present invention describes a compound of formula (IV):

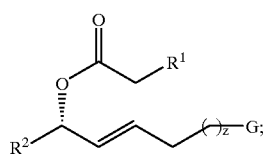

(IV)

wherein:
$R^1$ is —$CH_2CH(CH_3)_2$
$R^2$ is —$CH(CH_3)_2$;
G is —$OCH_2OCH_3$; and
z is 2.
In a sixth embodiment, the present invention describes a compound of formula (IV-a):

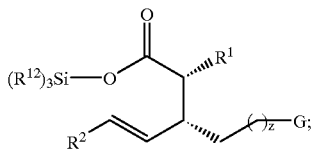

(V)

wherein:
$R^1$ is —$CH_2CH(CH_3)_2$;
$R^2$ is —$CH(CH_3)_2$;
$R^{12}$ is selected independently at each occurrence from $C_{1-6}$ alkyl or phenyl;
G is —$OCH_2OCH_3$ or —O-t-butyldimethylsilyl; and z is 2.

In a more preferred embodiment, the compound of formula (V) is:

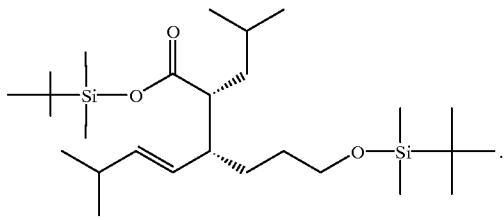

In another preferred embodiment, the compound of formula (V) is:

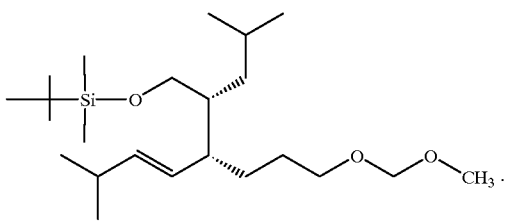

In a seventh embodiment, the present invention describes a compound of formula (V):

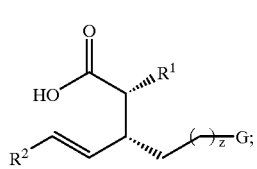

(V)

wherein:

$R^1$ is —$CH_2CH(CH_3)_2$;

$R^2$ is —$CH(CH_3)_2$;

G is —$OCH_2OCH_3$ or —O-t-butyldimethylsilyl; and z is 2.

In a more preferred embodiment, the compound of formula (V) is:

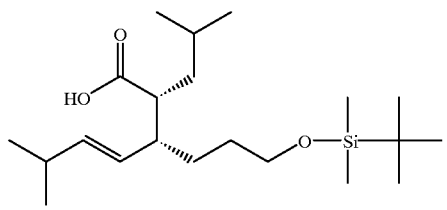

or a salt form thereof.

In another preferred embodiment, the compound of formula (V) is:

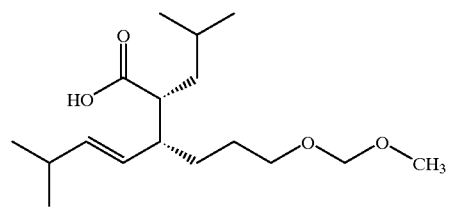

or a salt form thereof.

In an eighth embodiment, the present invention describes a compound of formula (VII):

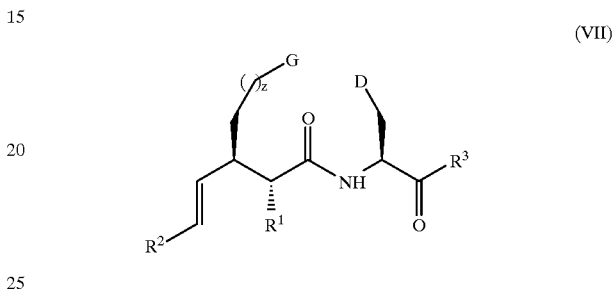

(VII)

or a salt form thereof;
wherein:

D is $P^1$—$NR^{11}$—$CH_2CH_2CH_2$—, or para HO—$C_6H_4$—;

G is —OP or halogen;

P is a suitable oxygen protecting group;

$P^1$ is a suitable nitrogen protecting group;

$P^1$ is a suitable nitrogen protecting group;

$R^1$ is selected from the group consisting of:
  $C_{1-5}$ alkyl substituted with 0–5 $R^{1a}$, —$(CH_2)_r$—$C_{3-10}$ cycloalkyl substituted with 0–5 $R^{1a}$, and —$(CH_2)_r$-aryl substituted with 0–5 $R^{1a}$;

$R^{1a}$ is selected independently at each occurrence from the group consisting of:
  hydrogen, —$CF_3$, —$CF_2CF_3$, —$NR^{1b}R^{1c}$, —$Si(R^{1d})_3$, $C_{1-5}$ alkyl, $C_{3-10}$ cycloalkyl, and aryl substituted with 0–5 $R^{1e}$;

$R^{1b}$ and $R^{1c}$ are selected independently at each occurrence from the group consisting of:
  $C_{1-5}$ alkyl, $C_{3-5}$ cycloalkyl and phenyl;

$R^{1d}$ is selected independently at each occurrence from the group consisting of:
  $C_{1-5}$ alkyl, $C_{1-5}$ haloalkyl, and aryl substituted with 0–5 $R^{1e}$;

$R^{1e}$ is selected independently at each occurrence from the group consisting of:
  $C_{1-5}$ alkyl, —$(CH_2)_r$—$OR^{1f}$, —OH, halo, —$NH_2$, and —$(CF_2)_rCF_3$;

$R^{1f}$ is selected independently at each occurrence from the group consisting of:
  $C_{1-5}$ alkyl, $C_{3-5}$ cycloalkyl and phenyl;

$R^2$ is selected from the group consisting of:
  $C_{1-10}$ alkyl, $C_{3-10}$ cycloalkyl, and —$(CH_2)_r$-phenyl substituted with 0–3 $R^{2a}$;

$R^{2a}$ is selected independently at each occurrence from the group consisting of:
  $C_{1-5}$ alkyl, —$(CH_2)_r$—$OR^{2b}$, —OH, halo, —$NH_2$, and —$(CF_2)_rCF_3$;

$R^{2b}$ is selected independently at each occurrence from the group consisting of:
  $C_{1-5}$ alkyl, $C_{3-5}$ cycloalkyl and phenyl;

$R^3$ is selected from the group consisting of:
  —$OR^4$, —$NR^5R^6$, —$NR^6(OR^5)$, $C_{1-5}$ alkyl substituted with 0–3 $R^{3a}$, —$(CH_2)_r$-aryl substituted with 0–5 $R^{3a}$, and —$(CH_2)_r$-heterocyclic substituted with 0–3 $R^{3a}$;

$R^{3a}$ is selected independently at each occurrence from the group consisting of:
  hydrogen, $C_{1-5}$ alkyl, halo, hydroxy, —O—$(CH_2)_r$—$R^{3b}$, —$(CH_2)_r$—$C(O)R^{3b}$, —$(CH_2)_r$—$SO_2NHR^{3b}$, —$(CH_2)_r$—$C(O)NHR^{3b}$, —$(CH_2)_r$—$OC(O)R^{3b}$, —$(CH_2)_r$—$NHSO_2R^{3b}$, aryl, —$(CH_2)_r$—$NHC(O)R^{3b}$, and —$(CH_2)_r$—$C(O)OR^{3b}$;

$R^{3b}$ is selected independently at each occurrence from the group consisting of:
  $C_{1-5}$ alkyl, $C_{3-5}$ cycloalkyl and phenyl;

$R^4$ is selected from the group consisting of:
  hydrogen, $C_1$–$C_{10}$ alkyl, —$(CH_2)_r$—$C_{3-10}$ cycloalkyl, —$(CH_2)_r$-heterocyclic, and —$(CH_2)_r$-aryl substituted with 0–5 $R^{4a}$;

$R^{4a}$ is selected independently at each occurrence from the group consisting of:
  $C_{1-5}$ alkyl, —$(CH_2)_r$—$OR^{4b}$, —OH, halo, —$NH_2$, and —$(CF_2)_rCF_3$;

$R^{4b}$ is selected independently at each occurrence from the group consisting of:
  $C_{1-5}$ alkyl, $C_{3-5}$ cycloalkyl and phenyl;

$R^5$ is selected from the group consisting of:
  $C_1$–$C_5$ alkyl, —$(CH_2)_r$—$C_3$–$C_{10}$ cycloalkyl, —$(CHR^{5a}Y)_n$—$R^9$, —$(CR^7R^8)_n$—O—$C(R^7R^8)_r$—$R^9$, —$(CR^7R^8)_r$—$R^9$, and —$(CR^7R^8)_rCONR^7R^8$;

$R^{5a}$ is selected independently at each occurrence from the group consisting of:
  hydrogen, $C_{1-10}$ alkyl substituted with 0–3 $R^{5b}$, —$(CH_2)_r$-aryl substituted with 0–3 $R^{5b}$, and —$(CH_2)_r$—O—$(CH_2)_r$-aryl substituted with 0–3 $R^{5b}$;

$R^{5b}$ is selected independently at each occurrence from the group consisting of:
  hydrogen, halo, hydroxy, —$OR^{5c}$, —$NHC(O)CH_3$, -aryl-$(CH_2)_r$—$NH_2$, -aryl-$(CH_2)_r$-aryl, $C_{1-10}$ alkyl substituted with 0–3 $R^{5d}$, and —$(CH_2)_r$-aryl substituted with 0–3 $R^{5d}$;

$R^{5c}$ is selected independently at each occurrence from the group consisting of:
  $C_{1-5}$ alkyl, $C_{3-5}$ cycloalkyl and phenyl;

$R^{5d}$ is selected independently at each occurrence from the group consisting of;
  hydrogen, $C_{1-5}$ alkyl, —O—$(CH_2)_r$—$R^{5e}$, —OH, halo, —$NHC(O)CH_3$, and —$C(O)NH_2$;

$R^{5e}$ is selected independently at each occurrence from the group consisting of:
  $C_{1-5}$ alkyl, $C_{3-5}$ cycloalkyl and phenyl;

$R^6$ is selected from the group consisting of:
  hydrogen, $C_1$–$C_{10}$ alkyl, —$(CH_2)_r$-aryl, —$(CH_2)_r$—$C(O)R^{6a}$, —$(CH_2)_r$-heterocyclic, and phenyl substituted with 0–5 $R^{6c}$;

$R^{6a}$ is selected independently at each occurrence from the group consisting of;
  hydrogen, $C_{1-5}$ alkyl, —O—$(CH_2)_r$—$R^{6b}$, —OH, halo, —$NHC(O)CH_3$, and —$C(O)NH_2$;

$R^{6b}$ is selected independently at each occurrence from the group consisting of:
  $C_{1-5}$ alkyl, $C_{3-5}$ cycloalkyl and phenyl;

$R^{6c}$ is selected independently at each occurrence from the group consisting of:
  halogen, $NO_2$, —$R^{6d}$, and —O—$(CH_2)_r$—$R^{6d}$;

$R^{6d}$ is selected independently at each occurrence from the group consisting of:
  $C_{1-5}$ alkyl, $C_{3-5}$ cycloalkyl and phenyl;

Alternatively, $R^5$ and $R^6$ combine to form a 3 to 8 membered heterocyclic ring containing 1 to 3 additional heteroatoms selected from —O—, —$NR^6$—, —S(O)p—, and —C(O)—, optionally fused to a phenyl ring;

$R^7$ and $R^8$ may be H or $R^{5a}$;

Alternatively, $R^7$ and $R^8$ combine to form 3 to 7 membered heterocyclic ring substituted with 1–3 $R^{7a}$, containing 1–3 additional heteroatoms selected from —O—, —S(O)p—, and —$NR^6$—, optionally fused to an aryl ring substituted with 0–3 $R^{7c}$;

$R^{7a}$ is selected independently at each occurrence from the group consisiting of:
  hydrogen, $C_{1-5}$ alkyl, $C_{3-5}$ cycloalkyl, hydroxy, halo, —$OR^{7b}$, —$NHC(O)CH_3$, —$C(O)NH_2$, and aryl;

$R^{7b}$ is selected independently at each occurrence from the group consisting of:
  $C_{1-5}$ alkyl, $C_{1-5}$ cycloalkyl and phenyl;

$R^{7c}$ is selected independently at each occurrence from the group consisting of;
  hydrogen, $C_{1-5}$ alkyl, $C_{3-5}$ cycloalkyl, hydroxy, halo, —$O(CH_2)_r$—$R^{7d}$, —$NHC(O)CH_3$, —$C(O)NH_2$, and aryl;

$R^{7d}$ is selected independently at each occurrence from the group consisting of:
  $C_{1-5}$ alkyl, $C_{1-5}$ cycloalkyl and phenyl;

$R^9$ is selected from the group consisting of: hydrogen, $C_{1-5}$ alkyl, —$C(O)OC_{1-5}$ alkyl, —$(CH_2)_r$-aryl substituted with 0–3 $R^{9a}$, and a 5 or 6 membered heterocyclic ring containing from 0 to 2 N, O or S(O)p, and substituted with 0–3 $R^{9a}$;

$R^{9a}$ is selected from the group consisting of:
  —OH, —O—$(CH_2)_r$—$R^{9b}$, —$C(O)OR^{9b}$, —$NHR^{10}$ and aryl;

$R^{9b}$ is selected from the group consisting of:
  $C_{1-5}$ alkyl, $C_{1-5}$ cycloalkyl and phenyl;

$R^{10}$ is independently at each occurrence H or $C_{1-10}$ alkyl substituted with 0–3 $R^{10a}$;

$R^{10a}$ is selected independently at each occurrence from the group consisting of:
  hydrogen, $C_1$–$C_{10}$ alkyl substituted with 0–3 $R^{10b}$, and —$(CH_2)_r$-aryl substituted with 0–3 $R^{10b}$;

$R^{10b}$ is selected independently at each occurrence from the group consisting of:
  hydrogen, halo, hydroxy, —$OR^{10c}$, —$NHC(O)CH_3$, —$(CH_2)_r$—$C(O)NH_2$, -aryl-$NH_2$, and —$SO_2NH_2$;

$R^{10c}$ is selected independently at each occurrence from the group consisting of:
  $C_{1-5}$ alkyl, $C_{1-5}$ cycloalkyl and phenyl;

$R^{11}$ is selected independently at each occurrence from the group consisting of:
  hydrogen, $C_1$–$C_{10}$ alkyl substituted with 0–3 $R^{11a}$, and —$(CH_2)_r$-aryl substituted with 0–3 $R^{11a}$;

$R^{11a}$ is selected independently at each occurrence from the group consisting of:
  hydrogen, halo, hydroxy, —$OR^{11b}$, —$NHC(O)CH_3$, —$(CH_2)_r$—$C(O)NH_2$, -aryl-$NH_2$, and —$SO_2NH_2$;

$R^{11b}$ is selected independently at each occurrence from the group consisting of:

C$_{1-5}$ alkyl, C$_{1-5}$ cycloalkyl and phenyl;
n is selected from 1, 2 and 3;
p is selected independently at each occurrence from 0, 1 and 2;
r is selected independently at each occurrence from 0, 1, 2, and 3;
Y is selected from the group consisting of: —CONR$^{10}$—, —NR$^{10}$CO—, —SO$_2$NR$^{10}$—, —NR$^{10}$SO$_2$—, and a 5 membered heterocyclic ring; and
z is selected from 1, 2, 3, 4 and 5.

In a ninth embodiment, the present invention describes a compound of formula (IX):

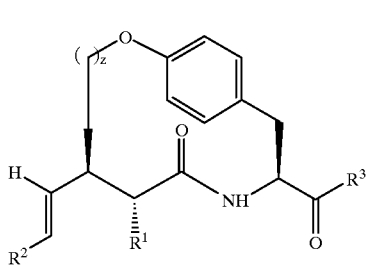

(IX)

or a salt form thereof;
wherein:
P$^1$ is a suitable nitrogen protecting group;
R$^1$ is selected from the group consisting of:
C$_{1-5}$ alkyl substituted with 0–5 R$^{1a}$, —(CH$_2$)$_r$—C$_{3-10}$ cycloalkyl substituted with 0–5 R$^{1a}$, and —(CH$_2$)$_r$-aryl substituted with 0–5 R$^{1a}$;
R$^{1a}$ is selected independently at each occurrence from the group consisting of:
hydrogen, —CF$_3$, —CF$_2$CF$_3$, —NR$^{1b}$R$^{1c}$, —Si(R$^{1d}$)$_3$, C$_{1-5}$ alkyl, C$_{3-10}$ cycloalkyl, and aryl substituted with 0–5 R$^{1e}$;
R$^{1b}$ and R$^{1c}$ are selected independently at each occurrence from the group consisting of:
C$_{1-5}$ alkyl, C$_{3-5}$ cycloalkyl and phenyl;
R$^{1d}$ is selected independently at each occurrence from the group consisting of:
C$_{1-5}$ alkyl, C$_{1-5}$ haloalkyl, and aryl substituted with 0–5 R$^{1e}$;
R$^{1e}$ is selected independently at each occurrence from the group consisting of:
C$_{1-5}$ alkyl, (CH$_2$)$_r$—OR$^{1f}$, —OH, halo, —NH$_2$, and —(CF$_2$)$_r$CF$_3$;
R$^{1f}$ is selected independently at each occurrence from the group consisting of:
C$_{1-5}$ alkyl, C$_{3-5}$ cycloalkyl and phenyl;
R$^2$ is selected from the group consisting of:
C$_{1-10}$ alkyl, C$_{3-10}$ cycloalkyl, and —(CH$_2$)$_r$-phenyl substituted with 0–3 R$^{2a}$;
R$^{2a}$ is selected independently at each occurrence from the group consisting of:
C$_{1-5}$ alkyl, —(CH$_2$)$_r$—OR$^{2b}$, —OH, halo, —NH$_2$, and —(CF$_2$)$_r$CF$_3$;
R$^{2b}$ is selected independently at each occurrence from the group consisting of:
C$_{1-5}$ alkyl, C$_{3-5}$ cycloalkyl and phenyl;
R$^3$ is selected from the group consisting of:
—OR$^4$, —NR$^5$R$^6$, —NR$^6$(OR$^5$), C$_{1-5}$ alkyl substituted with 0–3 R$^{3a}$, —(CH$_2$)$_r$-aryl substituted with 0–5 R$^{3a}$, and —(CH$_2$)$_r$-heterocyclic substituted with 0–3 R$^{3a}$;

R$^{3a}$ is selected independently at each occurrence from the group consisting of:
hydrogen, C$_{1-5}$ alkyl, halo, hydroxy, —O—(CH$_2$)$_r$—R$^{3b}$, —(CH$_2$)$_r$—C(O)R$^{3b}$, —(CH$_2$)$_r$—SO$_2$NHR$^{3b}$, —(CH$_2$)$_r$—C(O)NHR$^{3b}$, —(CH$_2$)$_r$—OC(O)R$^{3b}$, —(CH$_2$)$_r$—NHSO$_2$R$^{3b}$, aryl, —(CH$_2$)$_r$—NHC(O) R$^{3b}$, and —(CH$_2$)$_r$—C(O)OR$^{3b}$;
R$^{3b}$ is selected independently at each occurrence from the group consisting of:
C$_{1-5}$ alkyl, C$_{3-5}$ cycloalkyl and phenyl;
R$^4$ is selected from the group consisting of:
hydrogen, C$_1$–C$^{10}$ alkyl, —(CH$_2$)$_r$—C$_{3-10}$ cycloalkyl, —(CH$_2$)$_r$-heterocyclic, and —(CH$_2$)$_r$-aryl substituted with 0–5 R$^{4a}$;
R$^{4a}$ is selected independently at each occurrence from the group consisting of:
C$_{1-5}$ alkyl, —(CH$_2$)$_r$—OR$^{4b}$, —OH, halo, —NH$_2$, and —(CF$_2$)$_r$CF$_3$;
R$^{4b}$ is selected independently at each occurrence from the group consisting of:
C$_{1-5}$ alkyl, C$_{3-5}$ cycloalkyl and phenyl;
R$^5$ is selected from the group consisting of:
C$_1$–C$_5$ alkyl, —(CH$_2$)$_r$—C$_3$–C$_{10}$ cycloalkyl, —(CHR$^{5a}$Y)$_n$—R$^9$, —(CR$^7$R$^8$)$_n$—O—C(R$^7$R$^8$)$_r$—R$^9$, —(CR$^7$R$^8$)$_r$—R$^9$, and —(CR$^7$R$^8$)$_r$CONR$^7$R$^8$;
R$^{5a}$ is selected independently at each occurrence from the group consisting of:
hydrogen, C$_{1-10}$ alkyl substituted with 0–3 R$^{5b}$, —(CH$_2$)$_r$-aryl substituted with 0–3 R$^{5b}$, and —(CH$_2$)$_r$—O—(CH$_2$)$_r$-aryl substituted with 0–3 R$^{5b}$;
R$^{5b}$ is selected independently at each occurrence from the group consisting of:
hydrogen, halo, hydroxy, —OR$^{5c}$, —NHC(O)CH$_3$, -aryl-(CH$_2$)$_r$—NH$_2$, -aryl-(CH$_2$)$_r$-aryl, C$_{1-10}$ alkyl substituted with 0–3 R$^{5d}$, and —(CH$_2$)$_r$-aryl substituted with 0–3 R$^{5d}$;
R$^{5c}$ is selected independently at each occurrence from the group consisting of:
C$_{1-5}$ alkyl, C$_{3-5}$ cycloalkyl and phenyl;
R$^{5d}$ is selected independently at each occurrence from the group consisting of;
hydrogen, C$_{1-5}$ alkyl, —O—(CH$_2$)$_r$—R$^{5e}$, —OH, halo, —NHC(O)CH$_3$, and —C(O)NH$_2$;
R$^{5e}$ is selected independently at each occurrence from the group consisting of:
C$_{1-5}$ alkyl, C$_{3-5}$ cycloalkyl and phenyl;
R$^6$ is selected from the group consisting of:
hydrogen, C$_{1-10}$ alkyl, —(CH$_2$)$_r$-aryl, —(CH$_2$)$_r$—C(O) R$^{6a}$, —(CH$_2$)$_r$-heterocyclic, and phenyl substituted with 0–5 R$^{6c}$;
R$^{6a}$ is selected independently at each occurrence from the group consisting of;
hydrogen, C$_{1-5}$ alkyl, —O—(CH$_2$)$_r$—R$^{6b}$, —OH, halo, —NHC(O)CH$_3$, and —C(O)NH$_2$;
R$^{6b}$ is selected independently at each occurrence from the group consisting of:
C$_{1-5}$ alkyl, C$_{3-5}$ cycloalkyl and phenyl;
R$^{6c}$ is selected independently at each occurrence from the group consisting of:
halogen, NO$_2$, —R$^{6d}$, and —O—(CH$_2$)$_r$—R$^{6d}$;
R$^{6d}$ is selected independently at each occurrence from the group consisting of:
C$_{1-5}$ alkyl, C$_{3-5}$ cycloalkyl and phenyl;

29

Alternatively, $R^5$ and $R^6$ combine to form a 3 to 8 membered heterocyclic ring containing 1 to 3 additional heteroatoms selected from —O—, —$NR^6$—, —S(O)p-, and —C(O)—, optionally fused to a phenyl ring;

$R^7$ and $R^8$ may be H or $R^{5a}$;

Alternatively, $R^7$ and $R^8$ combine to form 3 to 7 membered heterocyclic ring substituted with 1–3 $R^{7a}$, containing 1–3 additional heteroatoms selected from —O—, —S(O)p-, and —$NR^6$—, optionally fused to an aryl ring substituted with 0–3 $R^{7c}$;

$R^{7a}$ is selected independently at each occurrence from the group consisiting of:
hydrogen, $C_{1-5}$ alkyl, $C_{3-5}$ cycloalkyl, hydroxy, halo, —$OR^{7b}$, —$NHC(O)CH_3$, —$C(O)NH_2$, and aryl;

$R^{7b}$ is selected independently at each occurrence from the group consisting of:
$C_{1-5}$ alkyl, $C_{1-5}$ cycloalkyl and phenyl;

$R^{7c}$ is selected independently at each occurrence from the group consisting of;
hydrogen, $C_{1-5}$ alkyl, $C_{3-5}$ cycloalkyl, hydroxy, halo, —$O(CH_2)_r$—$R^{7d}$, —$NHC(O)CH_3$, —$C(O)NH_2$, and aryl;

$R^{7d}$ is selected independently at each occurrence from the group consisting of:
$C_{1-5}$ alkyl, $C_{1-5}$ cycloalkyl and phenyl;

$R^9$ is selected from the group consisting of: hydrogen, $C_{1-5}$ alkyl, —$C(O)OC_{1-5}$ alkyl, —$(CH_2)_r$-aryl substituted with 0–3 $R^{9a}$, and a 5 or 6 membered heterocyclic ring containing from 0 to 2 N, O or S(O)p, and substituted with 0–3 $R^{9a}$;

$R^{9a}$ is selected from the group consisting of: —OH, —O—$(CH_2)_r$—$R^{9b}$, —$C(O)OR^{9b}$, —$NHR^{10}$ and aryl;

$R^{9b}$ is selected from the group consisting of: $C_{1-5}$ alkyl, $C_{1-5}$ cycloalkyl and phenyl;

$R^{10}$ is independently at each occurrence H or $C_{1-10}$ alkyl substituted with 0–3 $R^{10a}$;

$R^{10a}$ is selected independently at each occurrence from the group consisting of:
hydrogen, $C_1$–$C_{10}$ alkyl substituted with 0–3 $R^{10b}$, and —$(CH_2)_r$-aryl substituted with 0–3 $R^{10b}$;

$R^{10b}$ is selected independently at each occurrence from the group consisting of:
hydrogen, halo, hydroxy, —$OR^{10c}$, —$NHC(O)CH_3$, —$(CH_2)_r$—$C(O)NH_2$, -aryl-$NH_2$, and —$SO_2NH_2$;

$R^{10c}$ is selected independently at each occurrence from the group consisting of:
$C_{1-5}$ alkyl, $C_{1-5}$ cycloalkyl and phenyl;

n is selected from 1, 2 and 3;

p is selected independently at each occurrence from 0, 1 and 2;

r is selected independently at each occurrence from 0, 1, 2, and 3;

Y is selected from the group consisting of: —$CONR^{10}$—, —$NR^{10}CO$—, —$SO_2NR^{10}$—, —$NR^{10}SO_2$—, and a 5 membered heterocyclic ring; and z is selected from 1, 2, 3, 4 and 5.

30

In a preferred embodiment, the compound of formula (IX) is:

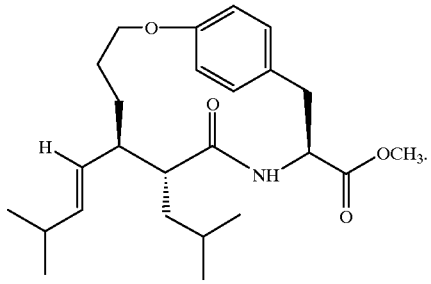

In another preferred embodiment, the compound of formula (IX) is:

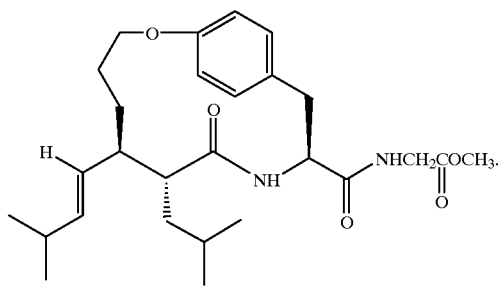

In another preferred embodiment, the compound of formula (IX) is:

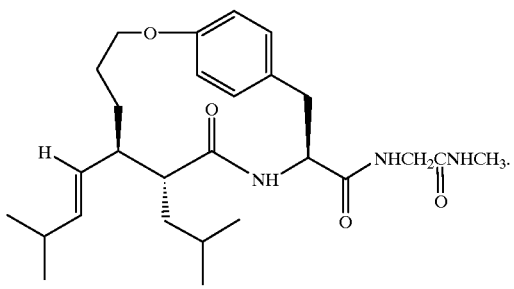

In a tenth embodiment, the present invention describes a compound formula (IX-a):

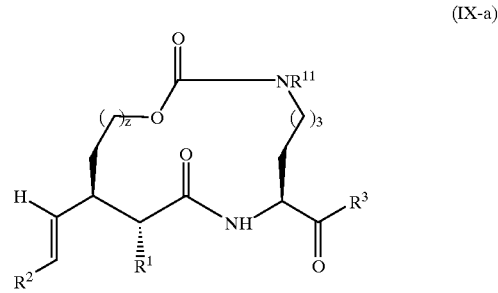

(IX-a)

or a salt form thereof;
wherein:
$P^1$ is a suitable nitrogen protecting group;
$R^1$ is selected from the group consisting of:

$C_{1-5}$ alkyl substituted with 0–5 $R^{1a}$, —$(CH_2)_r$—$C_{3-10}$ cycloalkyl substituted with 0–5 $R^{1a}$, and —$(CH_2)_r$-aryl substituted with 0–5 $R^{1a}$;

$R^{1a}$ is selected independently at each occurrence from the group consisting of:
hydrogen, —$CF_3$, —$CF_2CF_3$, —$NR^{1b}R^{1c}$, —$Si(R^{1d})_3$, $C_{1-5}$ alkyl, $C_{3-10}$ cycloalkyl, and aryl substituted with 0–5 $R^{1e}$;

$R^{1b}$ and $R^{1c}$ are selected independently at each occurrence from the group consisting of:
$C_{1-5}$ alkyl, $C_{3-5}$ cycloalkyl and phenyl;

$R^{1d}$ is selected independently at each occurrence from the group consisting of:
$C_{1-5}$ alkyl, $C_{1-5}$ haloalkyl, and aryl substituted with 0–5 $R^{1e}$;

$R^{1e}$ is selected independently at each occurrence from the group consisting of:
$C_{1-5}$ alkyl, —$(CH_2)_r$—$OR^{1f}$, —OH, halo, —$NH_2$, and —$(CF_2)_rCF_3$;

$R^{1f}$ is selected independently at each occurrence from the group consisting of:
$C_{1-5}$ alkyl, $C_{3-5}$ cycloalkyl and phenyl;

$R^2$ is selected from the group consisting of:
$C_{1-10}$ alkyl, $C_{3-10}$ cycloalkyl, and —$(CH_2)_r$-phenyl substituted with 0–3 $R^{2a}$;

$R^{2a}$ is selected independently at each occurrence from the group consisting of:
$C_{1-5}$ alkyl, —$(CH_2)_r$—$OR^{2b}$, —OH, halo, —$NH_2$, and —$(CF_2)_rCF_3$;

$R^{2b}$ is selected independently at each occurrence from the group consisting of:
$C_{1-5}$ alkyl, $C_{3-5}$ cycloalkyl and phenyl;

$R^3$ is selected from the group consisting of:
—$OR^4$, —$NR^5R^6$, —$NR^6(OR^5)$, $C_{1-5}$ alkyl substituted with 0–3 $R^{3a}$, —$(CH_2)_r$-aryl substituted with 0–5 $R^{3a}$, and —$(CH_2)_r$-heterocyclic substituted with 0–3 $R^{3a}$;

$R^{3a}$ is selected independently at each occurrence from the group consisting of:
hydrogen, $C_{1-5}$ alkyl, halo, hydroxy, —O—$(CH_2)_r$—$R^{3b}$, —$(CH_2)_r$—$C(O)R^{3b}$, —$(CH_2)_r$—$SO_2NHR^{3b}$, —$(CH_2)_r$—$C(O)NHR^{3b}$, —$(CH_2)_r$—$OC(O)R^{3b}$, —$(CH_2)_r$—$NHSO_2R^{3b}$, aryl, —$(CH_2)_r$—$NHC(O)R^{3b}$, and —$(CH_2)_r$—$C(O)OR^{3b}$;

$R^{3b}$ is selected independently at each occurrence from the group consisting of:
$C_{1-5}$ alkyl, $C_{3-5}$ cycloalkyl and phenyl;

$R^4$ is selected from the group consisting of:
hydrogen, $C_1$–$C_{10}$ alkyl, —$(CH_2)_r$—$C_{3-10}$ cycloalkyl, —$(CH_2)_r$-heterocyclic, and —$(CH_2)_r$-aryl substituted with 0–5 $R^{4a}$;

$R^{4a}$ is selected independently at each occurrence from the group consisting of:
$C_{1-5}$ alkyl, —$(CH_2)_r$—$OR^{4b}$, —OH, halo, —$NH_2$, and —$(CF_2)_rCF_3$;

$R^{4b}$ is selected independently at each occurrence from the group consisting of:
$C_{1-5}$ alkyl, $C_{3-5}$ cycloalkyl and phenyl;

$R^5$ is selected from the group consisting of:
$C_1$–$C_5$ alkyl, —$(CH_2)_r$—$C_3$-$C_{10}$ cycloalkyl, —$(CHR^{5a}Y)_n$—$R^9$, —$(CR^7R^8)_n$—O—$C(R^7R^8)_r$—$R^9$, —$(CR^7R^8)_r$—$R^9$, and —$(CR^7R^8)_r CONR^7R^8$;

$R^{5a}$ is selected independently at each occurrence from the group consisting of:
hydrogen, $C_{1-10}$ alkyl substituted with 0–3 $R^{5b}$, —$(CH_2)_r$-aryl substituted with 0–3 $R^{5b}$, and —$(CH_2)_r$—O—$(CH_2)_r$-aryl substituted with 0–3 $R^{5b}$;

$R^{5b}$ is selected independently at each occurrence from the group consisting of:
hydrogen, halo, hydroxy, —$OR^{5c}$, —$NHC(O)CH_3$, -aryl-$(CH_2)_r$—$NH_2$, -aryl-$(CH_2)_r$-aryl, $C_{1-10}$ alkyl substituted with 0–3 $R^{5d}$, and —$(CH_2)_r$-aryl substituted with 0–3 $R^{5d}$;

$R^{5c}$ is selected independently at each occurrence from the group consisting of:
$C_{1-5}$ alkyl, $C_{3-5}$ cycloalkyl and phenyl;

$R^{5d}$ is selected independently at each occurrence from the group consisting of;
hydrogen, $C_{1-5}$ alkyl, —O—$(CH_2)_r$—$R^{5e}$, —OH, halo, —$NHC(O)CH_3$, and —$C(O)NH_2$;

$R^{5e}$ is selected independently at each occurrence from the group consisting of:
$C_{1-5}$ alkyl, $C_{3-5}$ cycloalkyl and phenyl;

$R^6$ is selected from the group consisting of:
hydrogen, $C_1$–$C_{10}$ alkyl, —$(CH_2)_r$-aryl, —$(CH_2)_r$—$C(O)R^{6a}$, —$(CH_2)_r$-heterocyclic, and phenyl substituted with 0–5 $R^{6c}$;

$R^{6a}$ is selected independently at each occurrence from the group consisting of;
hydrogen, $C_{1-5}$ alkyl, —O—$(CH_2)_r$—$R^{6b}$, —OH, halo, —$NHC(O)CH_3$, and —$C(O)NH_2$;

$R^{6b}$ is selected independently at each occurrence from the group consisting of:
$C_{1-5}$ alkyl, $C_{3-5}$ cycloalkyl and phenyl;

$R^{6c}$ is selected independently at each occurrence from the group consisting of:
halogen, $NO_2$, —$R^{6d}$, and —O—$(CH_2)_r$—$R^{6d}$;

$R^{6d}$ is selected independently at each occurrence from the group consisting of:
$C_{1-5}$ alkyl, $C_{3-5}$ cycloalkyl and phenyl;

Alternatively, $R^5$ and $R^6$ combine to form a 3 to 8 membered heterocyclic ring containing 1 to 3 additional heteroatoms selected from —O—, —$NR^6$—, —$S(O)p$—, and —$C(O)$—, optionally fused to a phenyl ring;

$R^7$ and $R^8$ may be H or $R^{5a}$;

Alternatively, $R^7$ and $R^8$ combine to form 3 to 7 membered heterocyclic ring substituted with 1–3 $R^{7a}$, containing 1–3 additional heteroatoms selected from —O—, —$S(O)p$—, and —$NR^6$—, optionally fused to an aryl ring substituted with 0–3 $R^{7c}$;

$R^{7a}$ is selected independently at each occurrence from the group consisiting of:
hydrogen, $C_{1-5}$ alkyl, $C_{3-5}$ cycloalkyl, hydroxy, halo, —$OR^{7b}$, —$NHC(O)CH_3$, —$C(O)NH_2$, and aryl;

$R^{7b}$ is selected independently at each occurrence from the group consisting of:
$C_{1-5}$ alkyl, $C_{1-5}$ cycloalkyl and phenyl;

$R^{7c}$ is selected independently at each occurrence from the group consisting of;
hydrogen, $C_{1-5}$ alkyl, $C_{3-5}$ cycloalkyl, hydroxy, halo, —$O(CH_2)_r$—$R^{7d}$, —$NHC(O)CH_3$, —$C(O)NH_2$, and aryl;

$R^{7d}$ is selected independently at each occurrence from the group consisting of:
$C_{1-5}$ alkyl, $C_{1-5}$ cycloalkyl and phenyl;

$R^9$ is selected from the group consisting of: hydrogen, $C_{1-5}$ alkyl, —$C(O)OC_{1-5}$ alkyl, —$(CH_2)_r$-aryl substituted with 0–3 $R^{9a}$, and a 5 or 6 membered heterocyclic ring containing from 0 to 2 N, O or S(O)p, and substituted with 0–3 $R^{9a}$;

$R^{9a}$ is selected from the group consisting of:
—OH, —O—$(CH_2)_r$—$R^{9b}$, —C(O)O$R^{9b}$, —NH$R^{10}$ and aryl;

$R^{9b}$ is selected from the group consisting of:
$C_{1-5}$ alkyl, $C_{1-5}$ cycloalkyl and phenyl;

$R^{10}$ is independently at each occurrence H or $C_{1-10}$ alkyl substituted with 0–3 $R^{10a}$;

$R^{10a}$ is selected independently at each occurrence from the group consisting of: hydrogen, $C_1$–$C_{10}$ alkyl substituted with 0–3 $R^{10b}$, and —$(CH_2)_r$-aryl substituted with 0–3 $R^{10b}$;

$R^{10b}$ is selected independently at each occurrence from the group consisting of:
hydrogen, halo, hydroxy, —O$R^{10c}$, —NHC(O)CH$_3$, —$(CH_2)_r$—C(O)NH$_2$, -aryl-NH$_2$, and —SO$_2$NH$_2$;

$R^{10c}$ is selected independently at each occurrence from the group consisting of:
$C_{1-5}$ alkyl, $C_{1-5}$ cycloalkyl and phenyl;

$R^{11}$ is selected independently at each occurrence from the group consisting of:
hydrogen, $C_1$–$C_{10}$ alkyl substituted with 0–3 $R^{11a}$, and —$(CH_2)_r$-aryl substituted with 0–3 $R^{11a}$;

$R^{11a}$ is selected independently at each occurrence from the group consisting of:
hydrogen, halo, hydroxy, —O$R^{11b}$, —NHC(O)CH$_3$, —$(CH_2)_r$—C(O)NH$_2$, -aryl-NH$_2$, and —SO$_2$NH$_2$;

$R^{11b}$ is selected independently at each occurrence from the group consisting of:
$C_{1-5}$ alkyl, $C_{1-5}$ cycloalkyl and phenyl;

n is selected from 1, 2 and 3;

p is selected independently at each occurrence from 0, 1 and 2;

r is selected independently at each occurrence from 0, 1, 2, and 3;

Y is selected from the group consisting of: —CON$R^{10}$—, —N$R^{10}$CO—, —SO$_2$N$R^{10}$—, —N$R^{10}$SO$_2$—, and a 5 membered heterocyclic ring; and z is selected from 1, 2, 3, 4 and 5.

In a preferred embodiment, the compound of formula (IX-a) is:

In another preferred embodiment, the compound of formula (IX-a) is:

In another preferred embodiment, the compound of formula (IX-a) is:

DEFINITIONS

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

The following terms and abbreviations are used herein and defined as follows. The abbreviation: "THF" as used herein means tetrahydrofuran, "HPLC" as used herein means high performance liquid chromatograpy, "MOM" as used herein means methoxymethyl, "TBDS" means tert-butyldimethylsilane or tert-butyldimethylsilyl, "LDA" means lithium diisopropylamide, "py" means pyridine, "GC" means gas chromatography, "EE" means enantiomeric excess, "DE" means diastereomeric excess, "DIEA" means N,N-diisopropylethylamine, "BOC" means the protecting group tert-butyloxycarbonyl.

Suitable halogenated solvents include, but are not limited to: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include, but are not limited to: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable protic solvents include, but are not limited to: water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents include, but are not limited to: tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide (DMSO), propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include, but are not limited to: benzene, cyclohexane, pentane, hexane, toluene, cycloheptane, methylcyclohexane, heptane, ethylbenzene, m-, o-, or p-xylene, octane, indane, nonane, or naphthalene.

Suitable acids include, but are not limited to: hydrochloric acid, hydrobromic acid, sulfuric acid, phosphoric acid, nitric acid, and those acids referred to as organic acids.

Suitable organic acids include, but are not limited to: formic acid, acetic acid, propionic acid, butanoic acid, methanesulfonic acid, p-toluene sulfonic acid, benzenesulfonic acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

As used herein, a "suitable acid scavenger" refers to any species known in the art of organic synthesis capable of accepting a proton without reacting with the starting material or product. Examples include but are not limited to tertiary amines such as trimethylamine, triethylamine, N-methylmorpholine, diisopropylethylamine, pyridine, piperidine, and the like.

Suitable bases include, but are not limited to: lithium hydroxide, sodium hydroxide, potassium hydroxide, lithium carbonate, sodium carbonate, and potassium carbonate.

Strong bases include, but are not limited to, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The compounds described herein may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. Methods on how to prepare optically active forms from optically active starting materials are known in the art, such as by resolution of racemic forms or by synthesis. All chiral, diastereomeric, racemic forms and all geometric isomeric forms of a structure are intended.

The present invention includes all isotopes of atoms occurring in the intermediates or final compounds. Isotopes include those atoms having the same atomic number but different mass numbers. By way of general example and without limitation, isotopes of hydrogen include tritium and deuterium. Isotopes of carbon include C-13 and C-14.

When any variable (for example but not limited to $R^{1a}$, $R^{1b}$, $R^{1c}$, etc.) occurs more than one time in any constituent or in any formula, its definition on each occurrence is independent of its definition at every other occurrence. Thus, for example, if a group is shown to be substituted with 0–3 $R^{1a'}$, then said group may optionally be substituted with up to three $R^{1a'}$ and $R^{1a'}$ at each occurrence is selected independently from the defined list of possible $R^{1a'}$.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent. Such restrictions to the substituents which are compatible with the reaction conditions will be readily apparent to one skilled in the art and alternate methods must then be used.

The term "substituted", as used herein, means that any one or more hydrogen on the designated atom is replaced with a selection from the indicated group, provided that the designated atom's normal valency is not exceeded, and that the substitution results in a stable compound.

As used herein, any carbon range such as "$C_x$–$C_y$" is intended to mean a minimum of "x" carbons and a maximum of "y" carbons representing the total number of carbons in the substituent to which it refers. For example, "$C_3$–$C_{10}$ alkylcarbonyloxyalkyloxy" could contain one carbon for "alkyl", one carbon for "carbonyloxy" and one carbon for "alkyloxy" giving a total of three carbons, or a larger number of carbons for each carbon in an alkyl group not to exceed a total of ten carbons.

As used herein, "alkyl" is intended to include both branched and straight-chain saturated aliphatic hydrocarbon groups having the specified number of carbon atoms; for example, $C_1$–$C_4$ alkyl includes methyl, ethyl, n-propyl, i-propyl, n-butyl, i-butyl, s-butyl, and t-butyl; for example $C_1$–$C_{10}$ alkyl includes $C_1$–$C_4$ alkyl, pentyl, hexyl, heptyl, octyl, nonyl, decyl, and isomer thereof.

As used herein, "cycloalkyl" is intended to include saturated ring groups, including mono-, bi-, or poly-cyclic ring systems, such as cyclopropyl, cyclobutyl, cyclopentyl, cyclohexyl, cycloheptyl, cyclooctyl, and adamantyl.

As used herein, "Alkenyl" is intended to include hydrocarbon chains of either a straight or branched configuration and one or more unsaturated carbon-carbon bonds which may occur in any stable point along the chain, such as ethenyl, 1-propenyl, 2-propenyl, 1-butenyl, 2-butenyl, 3-butenyl, 1,3-butadienyl and the like. "Alkynyl" is intended to include hydrocarbon chains of either a straight or branched configuration and one or more triple carbon-carbon bonds which may occur in any stable point along the chain, such as ethynyl, propynyl, butynyl and the like.

"Aryl" is intended to mean phenyl or naphthyl. The term "arylalkyl" represents an aryl group attached through an alkyl bridge; for example $C_7$–$C_{11}$ arylalkyl can represent benzyl, phenylethyl and the like.

As used herein, "halo" or "halogen" refers to fluoro, chloro, bromo and iodo. Haloalkyl as used herein refers to an alkyl group containing a specified number of carbon atoms substituted with 1–10 halogens.

As used herein, the term "mesylate" is intended to mean —$OSO_2CH_3$. As used herein, the term "tosylate" is intended to mean —$OSO_2$—$C_6H_4$—$CH_3$, wherein $C_6H_4$ is a phenyl group and the methyl group is in the para position.

As used herein, the term "chain terminus" is intended to mean the G group at the end of the alkyl chain in the formula —$(CH_2)_z$—G.

As used herein, the term "hydroxide" is intended to mean lithium hydroxide, calcium hydroxide, magnesium hydroxide, sodium hydroxide, or potassium hydroxide.

As used herein, the term "heterocycle", "heterocyclic" or "heterocyclic ring" is intended to mean a stable 5- to 10-membered monocyclic or bicyclic or 5- to 10-membered bicyclic heterocyclic ring which may be saturated, partially unsaturated, or aromatic, and which consists of carbon atoms and from 1 to 3 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl or oxazolidinyl. Also included are fused ring and spiro compounds containing, for example, the above heterocycles.

As used herein, the term "suitable oxygen protecting group" includes those known in the art of organic synthesis to be temporary functional groups attached to oxygen which render it unreactive to the reagents in question, and can be readily removed to liberate the free oxygen. Examples of oxygen protecting groups include those which protect the oxygen of alcohol group (R—OH) and the oxygen of a carboxyl group (R—(C=O)O—).

Examples of alcohol protecting groups include, but are not limited to, the following: 1) ether types such as tetrahydropyranyl, triphenylmethyl, benzyl, allyl, tetrahydrofuranyl, methoxymethyl (MOM), benzyloxymethyl, p-methoxybenzyloxymethyl, 2-trimethylsilylethoxymethyl (SEM), t-butoxymethyl, methylthiomethyl, 2-methoxyethoxymethyl (MEM), trichloroethoxymethyl, t-butyl, p-methoxybenzyl, t-butyldimethylsilyl (TBDMS), o-nitrobenzyl, p-nitrobenzyl, p-methoxyphenyldiphenylmethyl, triisopropylsilyl, t-butyldiphenylsilyl; 2) ester types such as acetate, formate, mono-chloro, di-chloro, and trichloroacetate, methoxyacetate, triflouroacetate, triphenylmethoxy acetate, phenoxyacetate, pivaloate, adamantoate, benzoate, p-phenyl benzoate, isobutyrate, chlorodiphenylacetate; 3) carbonate types such as methyl, ethyl, 2,2,2-trichloroethyl, isobutyl, vinyl, allyl, p-nitrophenyl, benzyl, p-methoxybenzyl; 4) sulfonate types such as sulfate, methane sulfonate, benzylsulfonate, tosylate.

Examples of carboxyl protecting groups include, but are not limited to, the following: 1) substituted methyl ester type such as methoxymethyl, tetrahydropyranyl, benzyloxymethyl, N-phthalimidomethyl; 2) 2-substituted ethyl ester type such as 2,2,2-trichloroethyl, 2-methylthioethyl, t-butylethyl, cinnamylethyl, benzylethyl, 2-(2'-pyridyl)ethyl; 3) substituted benzyl ester type such as triphenylmethyl, 9-anthrylmethyl, p-nitrobenzyl, 4-picolyl, 2,4,6-trimethylbenzyl; 4) silyl ester type such as trimethylsilyl, t-butyldimethylsilyl, phenyldimethylsilyl; 5) miscellaneous type such as oxazole, orthoester; 6) amides type such as N,N-dimethyl, piperidinyl, pyrrolindinyl; and 7) hydrazide type such as alkylated hydrazides.

As used herein, the term "suitable nitrogen protecting group" includes those known in the art of organic synthesis to be a temporary functional group attached to nitrogen which renders it unreactive to the reagents in question, and can be readily removed to liberate the free nitrogen. Examples of nitrogen protecting groups include those which protect the nitrogen of an amine group (R—$NH_2$) and the nitrogen of an amide group (R—(C=O)NH—).

Examples of amine protecting groups include, but are not limited to, the following: 1) amide types such as formyl, trifluoroacetyl, phthalyl, and p-toluenesulfonyl; 2) aromatic carbamate types such as benzyl (Cbz) and benzyl substituted one or more time with with alkyl, cyano, nitro, chloro, fluoro, bromo, and methoxy; diphenylmethyl, 1-(p-biphenyl)-1-methylethyl, 9-fluorenylmethyl (Fmoc), 2-phenylethyl, and cinnamyl, 3) aliphatic carbamate types such as tert-butyl (Boc), ethyl, diisopropylmethyl, allyl, vinyl, t-amyl, diisopropylmethyl, and isobutyl ; 4) cyclic alkyl carbamate types such as cyclopentyl, cyclohexyl, cyclopropylmethyl, and adamantyl; 5) alkyl types such as triphenylmethyl (trityl) and benzyl; 6) trialkylsilane such as trimethylsilane; and 7) thiol containing types such as phenylthiocarbonyl and dithiasuccinoyl.

Examples of amide protecting groups include, but are limited to the substituted amides such as allyl, methoxymethyl, benzyloxymethyl, t-butyldimethylsiloxymethyl, methoxy, benzyloxy, t-butyldimethylsilyl, dimethoxybenzyl, and t-butyloxycarbonyl.

Groups which serve as nitrogen and oxygen protecting groups, and the methods employed to add and remove them will be readily understood by one skilled in the art, and are further described in *Protective Groups in Organic Synthesis,* Greene, 2nd ed., John Wiley & Sons, Inc., N.Y., 1991, the disclosure of which is hereby incorporated by reference.

As used herein, "S-Alpine Borane®" refers to B-isopinocampheyl-9-borabicyclo[3.3.1]nonane.

As used herein, "coupling agents" refers to an agent which is known in the art of organic synthesis capable of reacting in the presence of a carboxylic acid and an amine to produce an amide. Examples of such agents include, but are not limited to dicyclohexylcarbodiimide (DCC), diisopropylcarbodiimide (DIC), carbonyldiimidazole (CDI), 1-(3-dimethylamino propyl)-3-ethylcarbodiimide (EDC), O-(1H-benzo triazol-1-yl)-N,N,N',N',-tetramethyluronium tetraflouroborate (TBTU), and benzotriazol-1-yl-oxy-tripyrrolidinophosphonium hexafluorophosphate (PyBOP), (benzotriazolyloxy)tris(di methylamino)phosphonium hexafluorophosphate (BOP) and 2,3-dichloro-5,6-dicyano-1,4-benzoquinone (DDQ).

As used herein, "suitable silylating agent" means any agent which when reacted with an oxygen produces a silyl ester. Examples of such agents include, but are not limited to the flouro, bromo, chloro, iodo and anhydride derivatives of trimethylsilyl, triethylsilyl, triisopropylsilyl, dimethylisopropylsilyl, diethylisopropylsilyl, dimethythexylsilyl, t-butyldimethylsilyl, t-butyldiphenylsilyl, tribenzylsilyl, triphenylsilyl, diphenylmethylsilyl, and t-butylmethoxyphenylsilyl.

As used herein, "leaving group" means any group known in the art of organic synthesis to be displaced in a nucleophilic substitution reaction. These include, but are not limited to halogens, sulfate esters ($-SO_2R$), phosphate esters, azides, and the like.

As used herein, "pharmaceutically acceptable salts" refer to derivatives of the disclosed compounds wherein the intermediates or final compound are modified by making acid or base salts of the intermediates or final compounds. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the intermediates or final compounds include the conventional non-toxic salts or the quaternary ammonium salts from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts are generally prepared by reacting the free base or acid with stoichiometric amounts or with an excess of the desired salt-forming inorganic or organic acid or base in a suitable solvent or various combinations of solvents.

The pharmaceutically acceptable salts of the acids of the intermediates or final compounds are prepared by combination with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The present invention is contemplated to be practiced on at least a multigram scale, kilogram scale, multi kilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The methods of the present invention, by way of example and without limitation, may be further understood by reference to Schemes 2–4. Schemes 2–4 provide the general synthesis of compounds of formula (III)–(X). Compound of formula (II) can be prepared by methods described by S. D. Burke, et al. in *Tet. Lett.* 30, 6299 (89). Compounds of formula (VI) can be prepared by methods described in commonly assigned U.S. application Ser. No. 08/743439, the disclosure of which is hereby incorporated by reference. It is readily understood by one skilled in the art that alcohols and amines can be reacted with various compounds which, when attached to these atoms act as protecting groups. These groups are readily put on and removed by methods described in *Protective Groups in Organic Synthesis,* Greene, 2nd ed., John Wiley & Sons, Inc., N.Y., 1991. Further, alcohols may be converted to halogens and halogens may be converted to alcohols by methods described in *Advanced Organic Chemistry,* March, 3rd ed., John Wiley & Sons, Inc., N.Y., 1985, p. 382–384 and 326 respectively, the disclosure of which is hereby incorporated by reference.

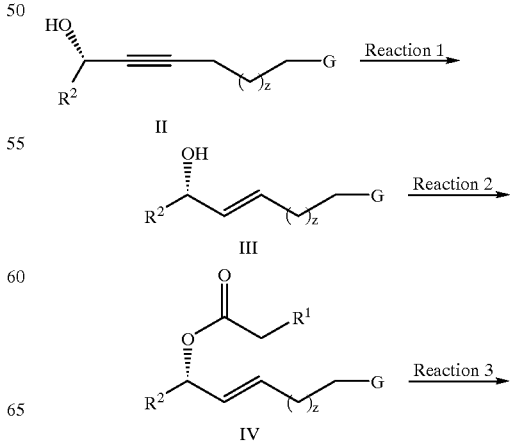

Scheme 2

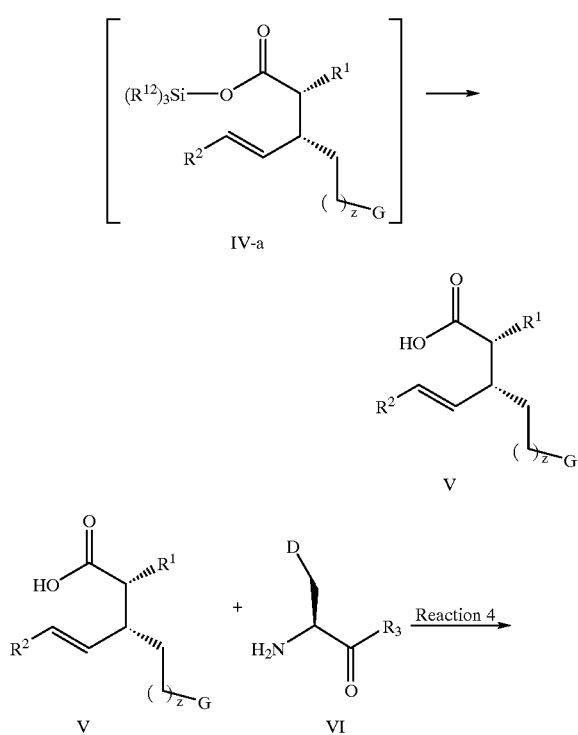
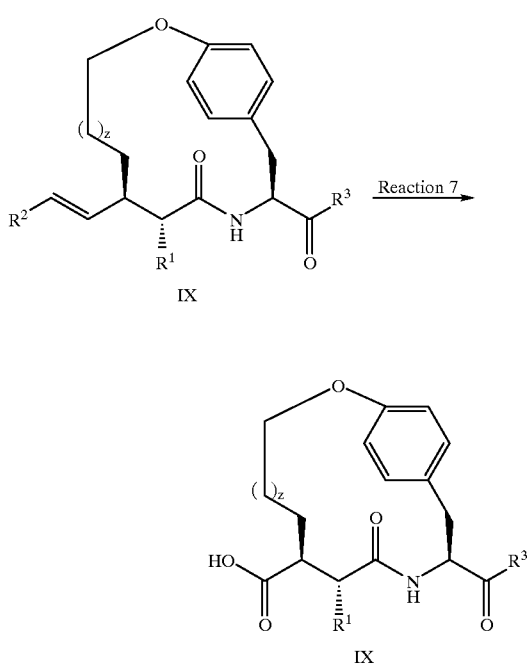
Scheme 3
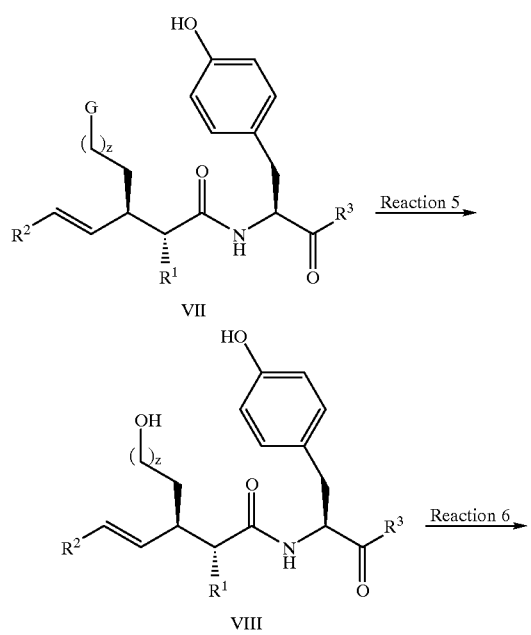
Scheme 4
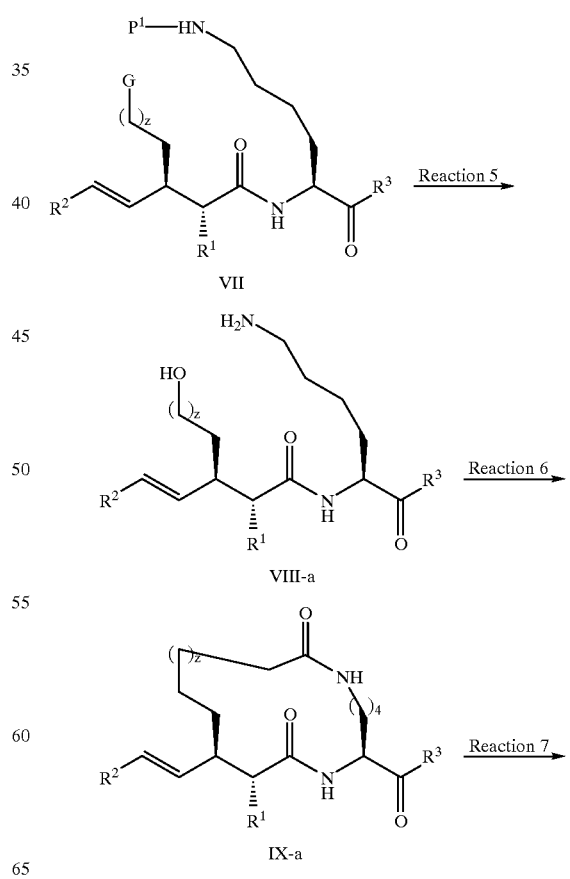

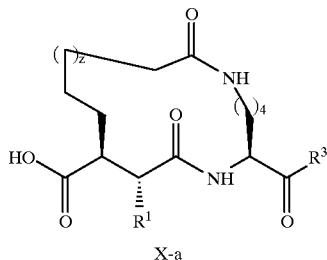

X-a

SYNTHESIS

In Reaction 1, the propargylic alcohol (II) is reduced to the E-allylic alcohol (III). A vessel is preferably charged with about 10 mL of solvent per gram of reducing agent. While numerous reaction solvents are possible, ethers, cyclic ethers and toluene are preferred. Tetrahydrofuran is most preferred. The solution is preferably cooled to about 0° C. with continuous agitation. The reducing agent is preferably added to the solution after the desired temperature is achieved. While numerous reducing agents are possible, lithium aluminum hydride, Red-Al, diisobutylaluminum hydride, Li—NH$_3$ and EtNH$_2$ are preferred. LiAlH$_4$ is most preferred. Enough reducing agent is added to preferably produce a concentration of about 1.0M in the reaction solvent. The number of equivalents of reducing agent after addition is preferably about 1.0 to about 2.0 equivalents based on 1 equivalent of starting material. More preferred is about 1.2 to about 1.5 equivalents. The temperature is preferably kept below about 10° C. during the addition of the starting material. A solution of the propargylic alcohol, preferably in the reaction solvent, is slowly added to the stirred solution. Preferably, the solution contains 10 mL of solvent per gram of propargyl alcohol and is added to the reaction vessel at about 0° C. After the addition is complete, the reaction is preferably allowed to warm up to about 10° C. to about 30° C. and then preferably heated to about 65° C. to about 70° C. for about 1 hour. If THF is the reaction solvent, the solution is preferably refluxed. Reaction progression is preferably monitored by removing an aliquot of the reaction mixture and quenching it, preferably by the addition of aqueous hydroxide. The reaction is considered complete when an organic extract of the reaction shows no trace of starting material by gas chromatography. The reaction mixture is preferably quenched at about 0° C. to about 10° C. by the careful addition of water. The salts of the residue are removed, preferably by filtering through a Celite pad. The cake is preferably washed with a volatile organic solvent such as an ether, or hydrocarbon of which tert-butyl methyl ether is preferred. The mother liquor is preferably washed once with an aqueous salt solution and dried. Numerous methods of drying are suitable, including the addition of drying agents such as sodium or magnesium sulfate and azeotropic distillation. The addition of magnesium sulfate is preferred followed by filtration. The solvent may be removed, preferably under vacuum to give the desired product. The product may be purified, preferably by vacuum distillation which will be readily understood by one skilled in the art.

In Reaction 2, the allylic alcohol (III) is acylated to give the Claisen precursor E-allyl ester (IV). The allylic alcohol (III) is preferably dissolved in about 5 mL to about 15 mL of the reaction solvent per gram of starting material. Numerous reaction solvents are possible, such as ethers, alkyl cyanides, halogenated and aryl solvents of which acetonitrile, THF, methylene chloride, toluene, diethyl ether, and dimethoxyethane are preferred. Acetonitrile is most preferred. The temperature of the resultant solution is preferably cooled to about 0° C. If R$^2$ is an aryl group the reaction is preferably cooled to about −78° C. to about −30° C. to avoid a [3,3] sigmatropic rearrangement. About −35° C. to about −45° C. is more preferred. An amine base is preferably added at the reduced temperature. Numerous amine bases may be used, of which pyridine, N-methyl morpholine and triethylamine are preferred. Pyridine is most preferred. The amount of base is preferably about 1.0 to about 2.0 equivalents. More preferred is about 1.2 to about 1.5 equivalents. An acid halide is preferably added dropwise to the solution. The amount of acid halide used is preferably about 1.0 to about 1.5 equivalents. The reaction is preferably warmed to about room temperature and stirred for about 1 to about 10 hours. The reaction is considered complete when the starting material has been completely consumed as evident by gas chromatography. After the reaction is judged complete, the solution is preferably cooled below room temperature and quenched by the addition of a suitable aqueous acid such as hydrochloric acid. The aqueous layer is preferably withdrawn and the non-aqueous layer extracted with additional portions of the aqueous acid. The aqueous layers are preferably combined and extracted with the reaction solvent or if the reaction solvent is water miscible, a suitable organic solvent. Preferred solvents include hydrocarbons, ether, aryls, chlorinated and acetates. All organic extracts are preferably combined, and washed with water, an aqueous base such as sodium bicarbonate and a salt solution such as aqueous sodium chloride. The organic solution is preferably dried and concentrated. Numerous methods of drying are suitable, including the addition of drying agents such as sodium or magnesium sulfate and azeotropic distillation. The addition of magnesium sulfate is preferred followed by filtration. The solvent may be removed under vacuum and the product may be purified, preferably by vacuum distillation to give the desired product which will be readily understood by one skilled in the art.

In Reaction 3, the allylic ester (IV) is converted the silyl ester anti-adduct, which may be isolated or hydrolyzed during work-up to give the corresponding acid (VI). The allylic ester is preferably dissolved in a suitable anhydrous solvent under inert atmosphere to give a molarity of about 0.9 to about 1.1 molar. Preferred solvents include cyclic or acyclic ethers such as diethyl ether, t-butyl methyl ether, tetrahydrofuran and dimethoxyethane, with tetrahydrofuran being most preferred. A suitable silylating agent is preferably dissolved in the solution. Preferred silylating agents include trimethyl silylchloride and t-butyldimethylsilylchloride. The amount of silylating agent is preferably about 1.0 to about 1.2 equivalents based on the allylic ester.

The allylic ester/silylating agent solution is preferably added to a second solution of reaction solvent containing a suitable strong base to form the desired E-enolate which is trapped by the alkylsilylhalide. This order of addition is preferred because it minimizes the degree of self condensation. Alternatively, a solution of the silylating agent may be added to a solution containing the allylic ester and base. While numerous bases may be used, lithium hexamethyldisilazide, lithium diisopropylamide and lithium tetramethyl piperidide (TMP) are preferred. Lithium diisopropylamide is most preferred. The solution preferably contains about 1.0 to about 1.5 equivalents of base based on allylic ester. About 1.1 to about 1.3 is most preferred. The basic solution preferably has a molarity of about 0.2 to about 1.0. The addition is preferably performed at a reduced temperature of about −78° C. to about −60° C. Most preferred is about −78° C. to about −70° C. The addition should be performed over the course of about 30 minutes to about 2 hours depending upon scale, preferably keeping the temperature within the preferred range. The resulting mixture is preferably stirred at a temperature of about −78° C. to about −70° C. for about 15 minutes to about 60 minutes. About 30 minutes to about 45 minutes is preferred. About 5 equivalents to about 8 equivalents of an additive such as such as 1,1,2,2-tetramethylethylene diamine (TMEDA), hexamethylphosphoramide (HMPA), and 1,3-dimethyl-3,4,5,6-tetrahydro-2(1H)-pyrimidinone (DMPU) may be introduced, preferably keeping the reaction below about −60° C., with below about −70° C. being most preferred. The reaction is preferably stirred keeping the temperature within the preferred range preferably for about 1 to about 5 hours. Most preferred is about 2 to about 4 hours, preferably followed by allowing the solution to warm up over about 1 to about 4 hours. The room temperature solution is preferably stirred overnight. More preferably, the reaction stirs about 5 to about 16 hours at room temperature prior to work-up.

The silyl ester may be isolated, if desired. This is preferably accomplished by the addition of a suitable solvent. Such suitable solvents include ethers and hydrocarbons, with hexane being preferred. The resultant solution is preferably extracted with water and an aqueous salt solution such as sodium chloride, and the organic layer preferably dried. Numerous methods of drying are suitable, including the addition of drying agents such as sodium or magnesium sulfate and azeotropic distillation. The addition of magnesium sulfate is preferred followed by filtration. The solvent may be removed, preferably under vacuum. The desired stereochemistry is preferably determined using the isolated silyl ester intermediate. The diastereoselectivity of the reaction preferably produces the preferred diastereomer in a ratio of about 10:1 for the anti:syn stereochemistry, respectively. More preferred is about 15:1 or higher. Most preferred when G is OMOM is about 18:1 or higher. Most preferred when G is OTBDMS is about 30:1 or higher. The preferred method of analysis for determining the chiral purity is gas chromatography. The weight percent yield of the reaction is preferably about 70 to about 99 percent. More preferred is about 80 to about 99 percent.

Alternatively, the reaction may be quenched with water and treated with hydroxide to cleave the silyl ester. The amount of hydroxide is preferably about 1 to about 3 equivalents based on the substrate. More preferred is about 1.5 to about 2.0 equivalents. While numerous hydroxide sources are possible, lithium hydroxide is preferred. The lithium carboxylate is generally soluble in organic solvents, and may be extracted into a suitable organic solvent. Preferably, the reaction solution is concentrated prior to extraction. All organic extracts are preferably combined, and washed with water, an aqueous base such as sodium bicarbonate and a salt solution such as aqueous sodium chloride. The organic solution is preferably dried and concentrated. Numerous methods of drying are suitable, including the addition of drying agents such as sodium or magnesium sulfate and azeotropic distillation. The addition of magnesium sulfate is preferred followed by fitration. The solvent may be removed under vacuum and the product may be purified, preferably by vacuum distillation to give the desired product which will be readily understood by one skilled in the art.

In Reaction 4, the anti-succinic acid adduct (V) is coupled with an amino acid derivative (VI). The free acid anti-succinate adduct from the Claisen rearrangement (V) is preferably dissolved in a suitable solvent. The amount of solvent employed is preferably from about 5 mLs to about 15 mLs per gram of starting material. A wide variety of solvents may be employed including aprotic, ether, halogented, and aryl solvents. Preferred are tetrahydrofuran, acetonitrile and N,N-dimethylformamide. N,N-dimethylformamide is most preferred. The amino acid is preferably dissolved with the starting material. The amount of amino acid is preferably from about 1.0 to about 1.5 equivalents. Most preferred is from about 1.0 to about 1.2 equivalents. An acid scavenger is preferably added to the vessel. While numerous chemical species may act as acid scavengers, tertiary amine bases such as pyridine, N-methyl morpholine, N,N-diisopropylethylamine and triethylamine are preferred. Triethylamine is most preferred. The preferred amount of acid scavenger is from about 1.0 to about 5.0 equivalents. Most preferred is about 2.0 to about 4.0 equivalents. The resultant solution is preferably cooled. The most preferred reaction temperature is about 0° C. to about 5° C. After the desired temperature is achieved, a coupling agent is preferably added to the solution. Many reagents may act as suitable coupling agents for the formation of the amide bond including thlonyl chloride, dicyclohexylcarbodiimide (DCC), carbonyldiimidazole (CDI), 1-(3-dimethylaminopropyl)-3-ethylcarbodiimide (EDC), O-(1H-benzotriazol-1-yl)-N,N,N',N',-tetramethyluronium tetraflouroborate (TBTU), benzotriazol-1-yl-oxy-tripyrrolidinophosphonium hexafluorophosphate (PyBOP) and benzotriazol-1-yl-oxy-tris-dimethylamino-phosphonium hexafluorophosphate (BOP). PyBOP and thionyl chloride are most preferred. It will be readily understood by one skilled in the art of organic synthesis that the use of thionyl chloride may be accompanied by an acid scavenger if labile protecting groups are present. Further, the order in which some of the components of a amide forming coupling reaction may be changed without substantially affecting the outcome of the reaction. For example, the base may be added after the coupling agent, or the acid may be first combined with the coupling agent before the addition of the nucleophile.

The reaction is preferably stirred at a reduced temperature for a period of about 1 hour to about 3 hours, then preferably allowed to warm to room temperature and stir for about 1 to about 4 hours. The reaction is considered complete when the starting acid has been been completely consumed, preferably as monitored by thin layer chromatography or NMR. The reaction is preferably diluted with an organic solvent, such as an ether, acetate, chlorinated or aryl solvent of which ethyl acetate is preferred. The organic solution is preferably washed with a suitable acid, with the most preferred being citric acid. The organic solution is preferably further washed with an aqueous base such as sodium bicarbonate and a salt solution such as aqueous sodium chloride. The organic solution is preferably dried and concentrated. Numerous methods of drying are suitable, including the addition of drying agents such as sodium or magnesium sulfate and azeotropic distillation. The addition of sodium sulfate is preferred followed by fitration. The solvent may be removed under vacuum and the product may be purified, preferably by recrystallization in a suitable solvent, the choice of which will be readily understood by one skilled in the art.

In Reaction 5, the coupled product may be deprotected either by liberating the protected oxygen, protected nitrogen, both, or neither depending upon the amino acid and chain terminus chosen. It will be understood by one skilled in the art, that if group G is a halogen, it will be converted to an oxygen only if a carbamate bridge is desired, as in the case of a macrocycle containing a lysine residue. Otherwise, the alkyl terminus is ready to undergo substitution with the phenolic alcohol of tyrosine. The halogen may be converted to an alcohol, preferably through the use of $CBr_4$ if a carbamate bridge is desired. This conversion will be readily understood by one skilled in the art. If however, the group G is a protected alcohol, conditions appropriate for the removal of the protecting group will be employed, such as the preferred method which is treatment with acid. With similiar reasoning, if lysine is the amino acid, the ω-protected nitrogen may be simultaneously deprotected under appropriate conditions, depending upon the protecting group. The preferred method of deprotection is the use of acid, for example when a butyloxycarbonyl (BOC) group is the nitrogen protector. If the tyrosine derivative is desired, the alcohol may be converted to the halogen by methods known in the art.

The following conditions may be used for the deprotection of alcohols.

Conditions to remove tetrahydropyranyl, triphenylmethyl, tetrahydrofuranyl, methoxymethyl, benzyloxymethyl, p-methoxybenzyloxymethyl, 2-trimethylsilyl ethoxymethyl, t-butoxymethyl, methylthiomethyl, 2-methoxyethoxymethyl, trichloroethoxymethyl, t-butyl, p-methoxyphenyldiphenyl methyl, may include: (a) 1–4M HCl in anhydrous or aqueous methanol, ethanol, isopropanol, tetrahydrofuran, dioxane, or diethyl ether; (b) 1–4M $H_2SO_4$ in anhydrous or aqueous methanol, ethanol, isopropanol, tetrahydrofuran, dioxane, or diethyl ether; (c) poly styrene sulfonic acid resin in anhydrous or aqueous methanol, ethanol, isopropanol, tetrahydrofuran, dioxane, or diethyl ether; (d) 10–100% trifluoroacetic acid in dichloromethane; or (e) p-toluenesulfonic acid or camphorsulfonic acid in anhydrous or aqueous methanol, ethanol, isopropanol.

Conditions to remove benzyl, benzyloxymethyl, p-methoxybenzyloxymethyl, p-methoxybenzyl, o-nitrobenzyl, p-nitrobenzyl which employ hydrogenolysis in the presence of 1–17% palladium on carbon, or palladium black may only be used to the extent that they do not effect the integrity of the double bond in structure (VII). Examples of such conditions include the use of pressures in combination with amounts of catalyst sufficient to reduce the double bond which will be readily understood by one skilled in the art. Conditions to remove o-nitrobenzyl group include irradiation of the compound at 320 nm wavelength for 5–60 minutes. These conditions can only be employed to the extent that they do not reduce the double bond in the Claisen product which will be readily understood by one skilled in the art.

Conditions to remove 2-trimethylsilylethoxymethyl, t-butyldimethylsilyl, triisopropylsilyl, t-butyldiphenylsilyl may include: treatment of the compound with tetrabutylammonium fluoride; or hydrogen flouride pyridine complex in THF, DMF or dimethylpropyleneurea.

Conditions to remove allyl may include: isomerization of the allyl ether with [Ir(COD)(Ph$_2$MeP)$_2$]PF$_6$ or (Ph$_3$P)$_3$RhCl in tetrahydrofuran, diethyl ether or dioxane followed by hydrolysis with aqueous HgCl$_2$.

It will be readily understood by one skilled in the art, that certain conditions used to deprotect hydroxy groups, will also be appropriate for the removal of nitrogen protecting groups such as t-butyloxycarbonyl (BOC). These conditions may include (a) 1–4M HCl in anhydrous or aqueous methanol, ethanol, isopropanol, tetrahydrofuran, dioxane, or diethyl ether; (b) 1–4M $H_2SO_4$ in anhydrous or aqueous methanol, ethanol, isopropanol, tetrahydrofuran, dioxane, or diethyl ether; (c) polystyrene sulfonic acid resin in anhydrous or aqueous methanol, ethanol, isopropanol, tetrahydrofuran, dioxane, or diethyl ether; (d) 10–100% trifluoroacetic acid in dichloromethane; or (e) p-toluenesulfonic acid or camphorsulfonic acid in anhydrous or aqueous methanol, ethanol, isopropanol. The following non-acidic conditions may be used for the deprotection of nitrogens.

| Protecting Group, Abbreviation | Preferred Nonacidic Removal Conditions |
|---|---|
| 2-trimethylsilylethyl carbamate, Teoc | $ZnCl_2$ in $CH_3NO_2$ |
| 1,1-dimethyl-2,2-dibromoethyl carbamate, DB-t-Boc | solvolysis with ethanol |
| 1-methyl-1-(4-biphenylyl)ethyl carbamate, Bpoc | tetrazole in trifluoroethanol |
| 2-(p-toluenesulfonyl)ethyl carbamate | 1 M NaOH in alcohol |
| m-nitrophenyl carbamate | photolysis |
| o-nitrobenzyl carbamate | photolysis |
| 3,5-dimethoxybenzyl carbamate | photolysis |
| 3,4-dimethoxy-6-nitrobenzyl carbamate | photolysis |
| N'-p-toluenesulfonylamino-carbonyl | alcoholysis |
| phthalimide | $CH_3NH_2$ in ethanol |
| dithiasuccinimide, Dts | mercaptoethanol and $Et_3N$ |
| 2,5-dimethylpyrrole | ozonolysis |
| benzyl | Na and $NH_3$ |
| methanesulfonamide, Ms | lithium aluminum hydride |

In Reaction 6, the compound is cyclized. Two cyclization procedures are possible depending upon the bridging unit desired. If an ether linker is desired, the chain terminus may be a halogen in reactions 1–5. The halogen may also be derived later in the synthesis from an alcohol, which may be deprotected in reaction 5, then converted to either a halogen, or a sulfonate (or phosphate) ester by procedures known in the art. Such procedures for conversion to a halogen include treatment with $CBr_4$ and $PPh_3$ in a suitable solvent. Such procedures for conversion of an alcohol to a sulfonate ester include treatment with a halo derivative of the desired sulfonyl group in the presence of an acid scavenger. The other reactive end is either the phenolic alcohol of tyrosine, or the ω-nitrogen of lysine.

The cyclization substrate is preferably dissolved in a suitable solvent. Preferred solvents include N,N-dimethylformamide and dimethylsulfoxide. A base is preferably dissolved in a suitable solvent. Preferred solvents include N,N-dimethylformamide and dimethyl seulfoxide. Most preferred is about a 4:1 mixture of N,N-dimethylformamide and dimethylsulfoxide. The basic solution is preferably heated. Preferred temperatures are about 40° C. to about 80° C. The solution containing the substrate is preferably added to the basic solution. The resultant solution is preferably heated until the starting material is consumed. Preferred temperatures are about 40° C. to about 80° C. More preferred is about 60° C. to about 85° C. Most preferred is 75° C. to about 85° C. The reaction is judged complete when the starting material is consumed, as evident by TLC. The reaction is preferably cooled and quenched with a suitable acid such as sodium bisulfate. The solution is preferably partitioned between the quenching acid and an organic solvent. Preferred organic solvents include aryls, chlorinated hydrocarbons, ethers and acetates. Most preferred is ethyl acetate. The aqueous layer is preferably extracted two to three times with the extraction solvent. The combined organics are then preferably washed two to three times with water and a saturated salt solution such as aqueous sodium chloride. The organic solution is preferably dried and concentrated. Numerous methods of drying are suitable, including the addition of drying agents such as sodium or magnesium sulfate and azeotropic distillation. The addition of sodium sulfate is preferred followed by fitration. The solvent may be removed under vacuum and the product may be purified, preferably by recrystallization in a suitable solvent, the choice of which will be readily understood by one skilled in the art.

If a carbamate linker (—OCONH—) is desired, the chain terminus is preferably an alcohol, deprotected in reaction 5. The chain terminus may also be a halogen through reaction 1–5, converted to an alcohol by procedures known in the art, such as treatment with hydroxide in a suitable solvent system. The other reactive end is the ω-nitrogen of lysine, preferably deprotected in Step 5.

The starting material is preferably dissolved in a suitable solvent. While numerous solvents are possible, ethers are preferred. Tetrahydrofuran is most preferred. The solution is preferably cooled. Preferred temperatures include about −78° C. to about 5° C. Most preferred is about −5° C. to about 5° C. An acid scavenger is preferably added via syringe or dropping funnel. While numerous chemical species may act as acid scavengers, tertiary amine bases such as pyridine, N-methyl morpholine, N,N-diisopropyl ethylamine, and triethylamine are preferred. N,N-diisopropylethylamine is most preferred. The preferred amount of acid scavenger is from about 1.0 to about 5.0 equivalents. Most preferred is about 2.0 to about 4.0 equivalents. A phosgene or phosgene equivalent is preferably added dropwise. The reaction is preferably stirred for about 1 to about 7 hours. More preferred is about 4 to about 6 hours, warming the reaction to room temperature during the last hour after isocyanate formation if evident by TLC. A catalyst is preferably dissolved in the reaction solvent and added. The preferred concentration when all material is added is about 0.3 M to about 0.5 M. Preferred catalysts include, but are not limited to cupric halides and alkyl tin reagents such as dibutyltin dilaurate, which is preferred. The amount of catalyst is preferably about 1 percent to about 10 percent by weight of the starting material. Most preferred is about 4 percent to 6 percent. The reaction is preferably stirred for about 1 to about 5 additional hours. The reaction is considered complete when all starting material has been consumed, as evident by TLC. Product formation may also be evident by HPLC. The reaction is preferably diluted with a water immiscible organic solvent, such as an ether, aryl or acetate. The solution is preferably stirred to achieve the dissolution of any solids, followed by extraction with an acid aqueous medium. Saturated ammonium chloride is preferred. The organics are preferably washed one to two times with water and a salt solution such as aqueous sodium chloride. The organic solution is preferably dried and concentrated. Numerous methods of drying are suitable, including the addition of drying agents such as sodium or magnesium sulfate and azeotropic distillation. The addition of sodium sulfate is preferred followed by fitration. The solvent may be removed under vacuum and the product may be purified, preferably by recrystallization in a suitable solvent, the choice of which will be readily understood by one skilled in the art.

In Reaction 7, the olefin is oxidized to give a carboxylate group. The substrate is preferably taken up in a suitable solvent. While many solvents may be used, alcoholic solvents are preferred. Methanol is most preferred. The solution is preferably cooled. Preferred temperatures are about −78° C. to about 5° C. A suitable oxidizing agent is preferably added. Preferred oxidizing agents include ozone and potassium permanganate in sodium periodate. Ozone is most preferred. Preferably, ozone is bubbled through the solution. The solution preferably turns blue, and is monitored by TLC. The reaction is considered complete when the starting material is consumed. An inert gas is preferably bubbled through the solution to to remove residual ozone. The mixture is preferably concentrated under reduced pressure. The residual material is preferably dissolved in a suitable acid. Suitable acids include organic and mineral acids. Organic acids are preferred. Formic acid is most preferred. The acid addition is preferably followed by the addition of a peracid. Aqueous hydrogen peroxide is preferred. The percent weight of the peroxide solution in water is preferably about 3 percent to 50 percent by weight. Most preferred is about 20 percent to 30 percent. The mixture is preferably stirred for a suitable period of time at room temperature. The amount of time is preferably 1 to 7 hours, or until the starting material is consumed, as evident by TLC. The reaction is preferably quenched by the addition of an aqueous acid at reduced temperature. The preferred acid is sodium bisulfate. The reaction may be tested for peroxide, as is understood in the art. The product may be isolated by extraction with an organic solvent such as aryl, ether or acetate. The organics are preferably washed one to two times with water and a salt solution such as aqueous sodium chloride. The organic solution is preferably dried and concentrated. Numerous methods of drying are suitable, including the addition of drying agents such as sodium or magnesium sulfate and azeotropic distillation. The addition of sodium sulfate is preferred followed by fitration. The solvent may be removed under vacuum and the product may be purified, preferably by recrystallization in a suitable solvent, the choice of which will be readily understood by one skilled in the art.

The present invention may be further exemplified, without limitation, by reference to Schemes 5–6.

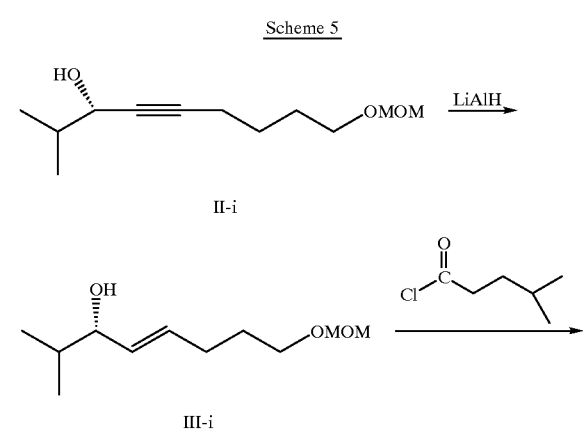

-continued
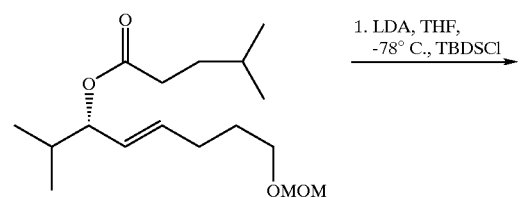
IV-i
1. LDA, THF, −78° C., TBDSCl →
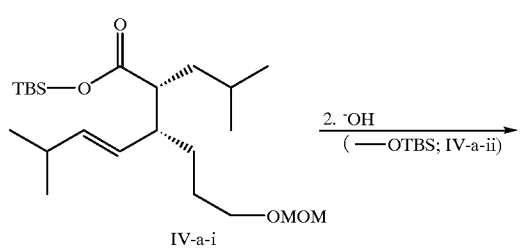
IV-a-i
2. ⁻OH
(—OTBS; IV-a-ii) →
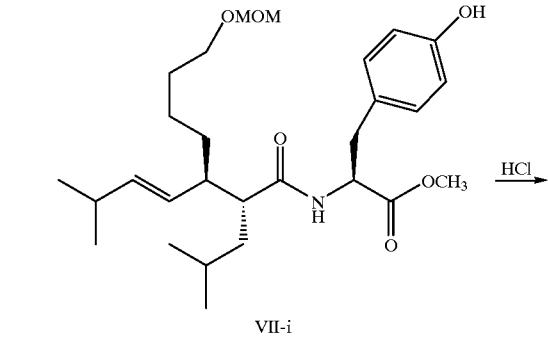
V-i
+
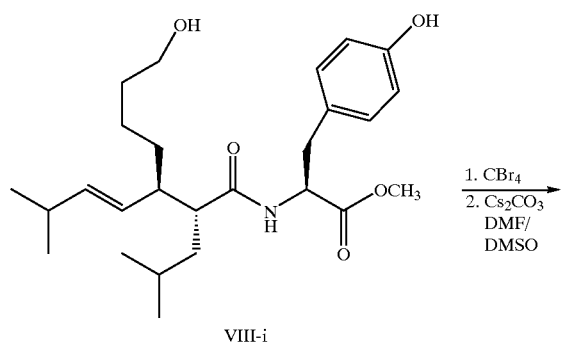
VI-i
BOP →
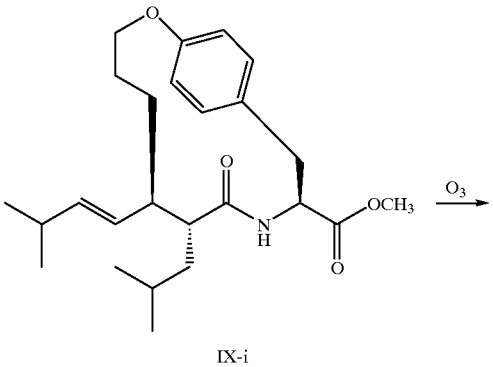
IX-i
O₃ →
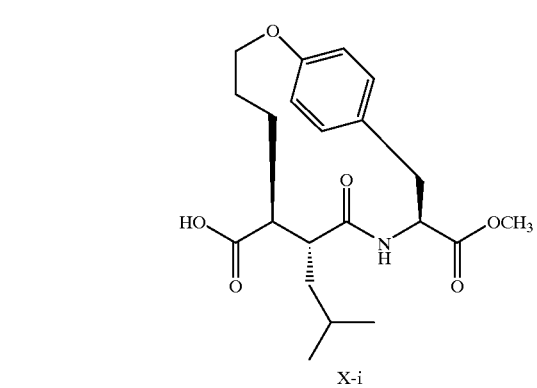
X-i
Scheme 6
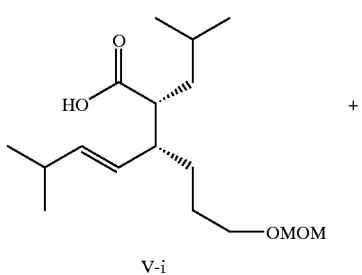
V-i
+
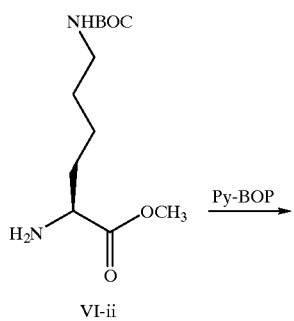
VI-ii
Py-BOP →
VII-i
HCl →
VIII-i
1. CBr₄
2. Cs₂CO₃
DMF/DMSO
→

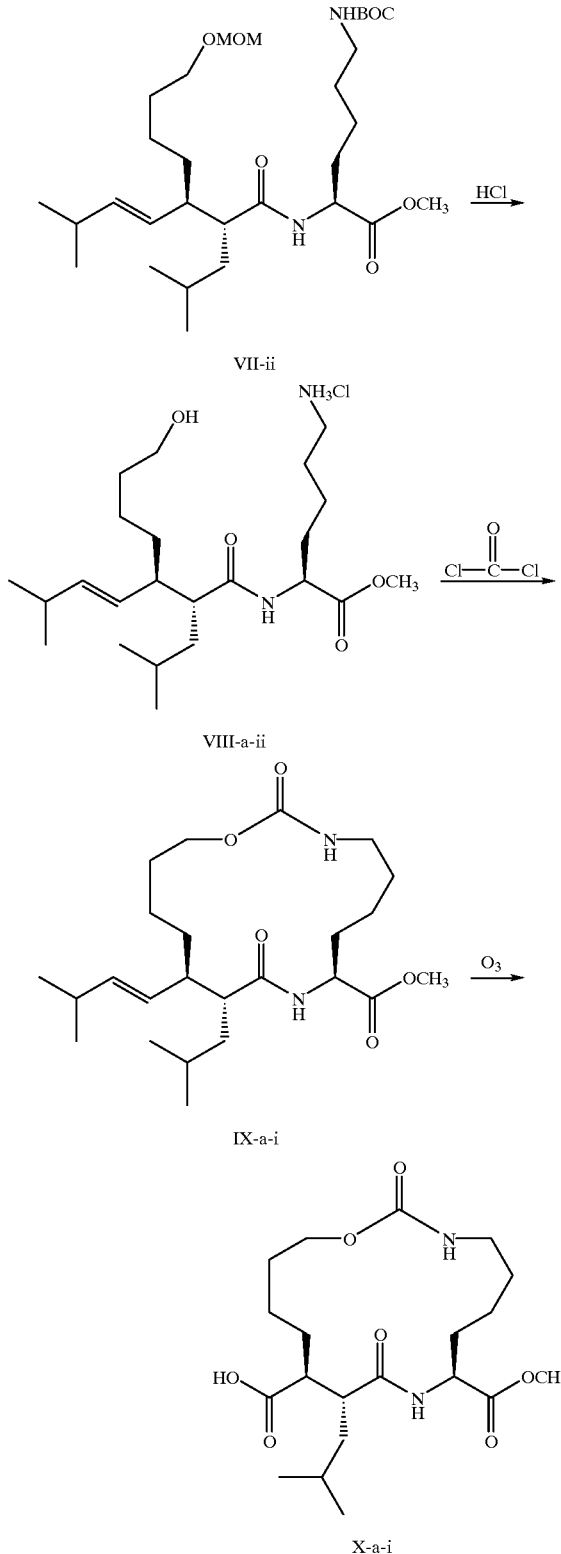

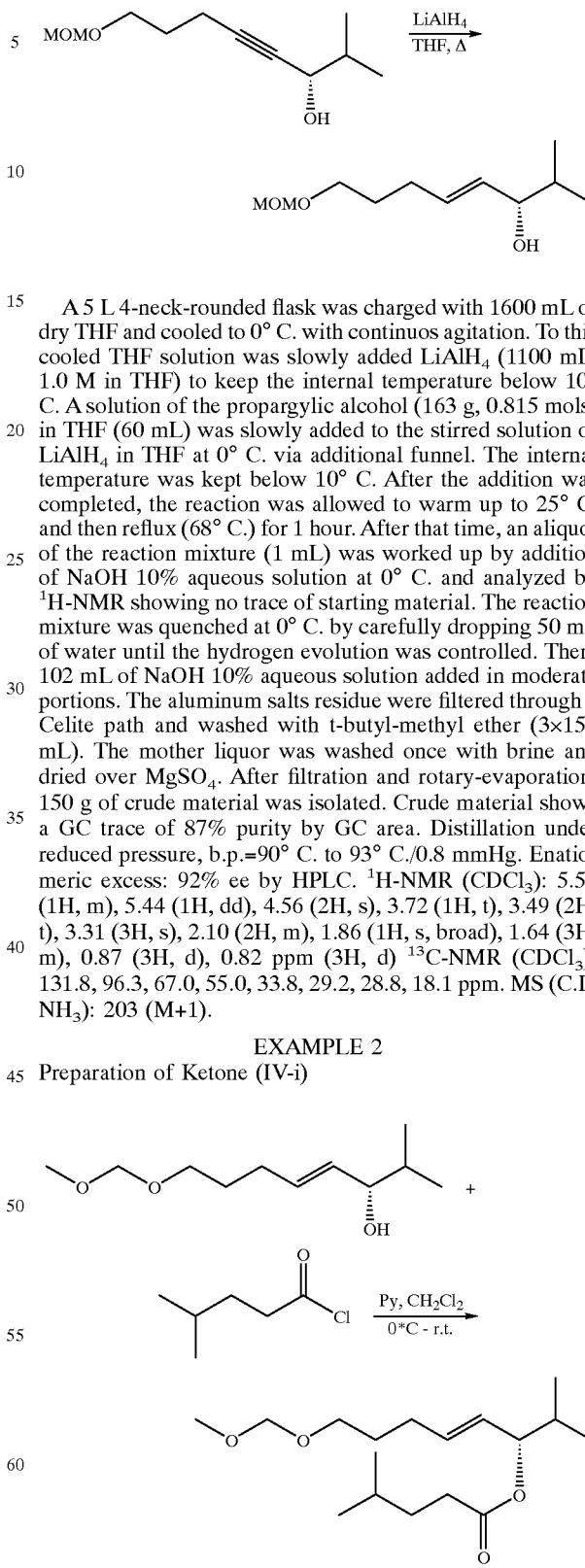

EXAMPLE 1
Preparation of Allylic Alcohol (III-i)

A 5 L 4-neck-rounded flask was charged with 1600 mL of dry THF and cooled to 0° C. with continuos agitation. To this cooled THF solution was slowly added LiAlH$_4$ (1100 mL, 1.0 M in THF) to keep the internal temperature below 10° C. A solution of the propargylic alcohol (163 g, 0.815 mols) in THF (60 mL) was slowly added to the stirred solution of LiAlH$_4$ in THF at 0° C. via additional funnel. The internal temperature was kept below 10° C. After the addition was completed, the reaction was allowed to warm up to 25° C. and then reflux (68° C.) for 1 hour. After that time, an aliquot of the reaction mixture (1 mL) was worked up by addition of NaOH 10% aqueous solution at 0° C. and analyzed by $^1$H-NMR showing no trace of starting material. The reaction mixture was quenched at 0° C. by carefully dropping 50 mL of water until the hydrogen evolution was controlled. Then, 102 mL of NaOH 10% aqueous solution added in moderate portions. The aluminum salts residue were filtered through a Celite path and washed with t-butyl-methyl ether (3×150 mL). The mother liquor was washed once with brine and dried over MgSO$_4$. After filtration and rotary-evaporation, 150 g of crude material was isolated. Crude material shows a GC trace of 87% purity by GC area. Distillation under reduced pressure, b.p.=90° C. to 93° C./0.8 mmHg. Enatiomeric excess: 92% ee by HPLC. $^1$H-NMR (CDCl$_3$): 5.58 (1H, m), 5.44 (1H, dd), 4.56 (2H, s), 3.72 (1H, t), 3.49 (2H, t), 3.31 (3H, s), 2.10 (2H, m), 1.86 (1H, s, broad), 1.64 (3H, m), 0.87 (3H, d), 0.82 ppm (3H, d) $^{13}$C-NMR (CDCl$_3$): 131.8, 96.3, 67.0, 55.0, 33.8, 29.2, 28.8, 18.1 ppm. MS (C.I., NH$_3$): 203 (M+1).

EXAMPLE 2
Preparation of Ketone (IV-i)

The following examples are meant to be illustrative of the present invention. These examples are presented to exemplify the invention, and are not to be construed as limiting the inventors scope.

In a 2 L 4-neck-rounded flask was dissolved the allylic alcohol (121 g, 0.60 mols) in CH$_2$Cl$_2$ (1.2 L) and cooled to 0° C. with continues agitation, under nitrogen. To this stirred solution was added pyridine (72.79 mL, 0.90 mols) in one portion. 4-Methyl valeryl chloride (121 g, 0.90 mols) was charged into an additional funnel and added to the stirred reaction mixture at 0° C. dropwise. The solution turned yellow during addition. The reaction mixture was allowed to warm slowly to r.t. After 10 h of stirring at r.t. no starting material was shown on TLC (hexane/ethyl acetate:4:1 v/v). The solution was cooled to 0° C. and quenched with 400 mL of HCl (0.5 M). The organic phase was washed three times with HCl (0.5 M, 200 mL). The combined aqueous layers were extracted once with 300 mL of $CH_2Cl_2$. The combined organic layers was subsequently washed once with 300 mL of water, 300 mL $NaHCO_3$ (sat.) and 400 mL of brine. Finally, the solution was dried over $MgSO_4$ and rotary evaporated to afford 208 g (112%) of crude allylic ester. The product was purified by reduced pressure distillation. b.p.= 125 to 128° C./0.8 mmHg. Enantiomeric excess: 93%ee by HPLC. $^1$H-NMR (CDCl$_3$): 5.68 (1H, m), 5.38 (1H, q), 5.00 (1H, t), 4.62 (2H, s), 3.52 (2H, t), 3.34 (3H, s), 2.30 (2H, t), 2.14 (2H, q), 1.83 (1H, m), 1.67 (2H, m), 1.54 (3H, m), 0.92 (6H, dd), 0.89 ppm (6H, dd). $^{13}$C-NMR (CDCl$_3$): 173.2, 134.1, 127.2, 96.3, 79.1, 66.9, 55.0, 33.1, 32.7, 32.0, 29.0, 28.8, 27.6, 22.2, 18.0 ppm. MS (C.I., $NH_3$): 301(M+1).

EXAMPLE 3
Preparation of Silyl Ester (IV-a-i)

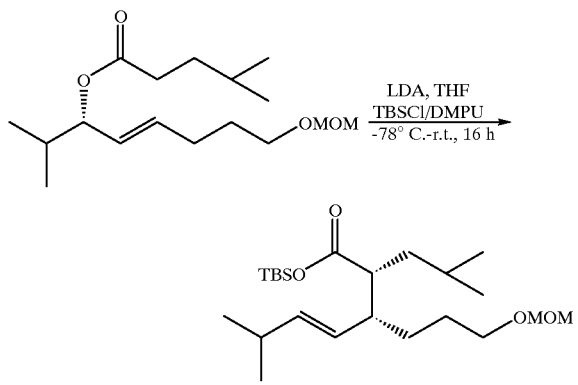

To a dry 500 mL 3-neck-round bottom flask equipped with a magnetic stirring bar, nitrogen inlet and outlet under nitrogen atmosphere was charged with 150 mL of dry THF and diisopropylamine (4.36 g, 43.05 mmol, 1.3 equivalent). The solution was cooled to 0° C. with stirring. To this solution, n-butyl lithium (26.9 mL of 1.6 M solution in THF, 43.05 mmol, 1.3 equivalent) was added slowly (in such a rate that internal temperature did not exceed 5° C.). The solution was stirred at 0° C. for 1 hour and then cooled to −78° C. The titled allylic ester (9.95 g, 33.12 mmol) in 35 mL THF solution was added very slowly (in such a rate that internal temperature did not exceed −72° C.) to the LDA solution with vigorous stirring. The reaction mixture was stirred for 45 minutes at −78° C. followed by the addition of TBSCl (5.5 g in 45 ml of THF, 36.4 mmol, 1.1 equivalent) slowly (internal temperature<−72° C.) and then DMPU (25 mL) slowly (internal temperature<−72° C.). The reaction mixture was stirred at −78° C. for 30 minutes, and then gradually warmed from −78° C. to room temperature and stirred at room temperature for 14 hours. The reaction was then quenched with saturated ammonium chloride solution (150 mL) and extracted with hexane (3×150 ml). The combined organic phases were dried with anhydrous magnesium sulfate (10 g). Filtration to filtered magnesium sulfate, and the solvents were removed with rotoevaporate under reduced pressure. The residue was then dried under high vacuum to produce 11.3 g (83% yield). The enantio-selectivity: 93%ee (by GC), diastereoselectivity, anti/syn >30:1 (by NMR). $^{13}$C-NMR (300 MHz, ppm, CDCl3): 17.5, 21.5, 22.2, 22.6, 22.7, 23.7, 25.4, 25.5, 25.6, 26.5, 27.6, 29.7, 31.1, 39.5, 46.0, 50.5, 55.0, 67.7, 96.3, 127.9, 140.4, 176.1. $^1$H-NMR (300 MHz, ppm, CDCl3, J=Hz): 0.16 (s, 6H), 0.82 (dd, J=5.7, 5.7, 6H), 0.84, (s, 9H), 0.88 (d, J=23, 6H), 1.09~1.22 (m, 3H), 1.23~1.49 (m, 4H), 2.02 (m, 1H), 2.16 (m, 3H), 2.24 (s, 3H), 3.37 (t, J=6.1, 2H), 4.49 (s, 2H), 4.87 (dd, J=15.57, 8.25, 1H), 5.29 (dd, J=15.2, 8.25, 1H).

EXAMPLE 4
Preparation of Silyl Ester (IV-a-ii)

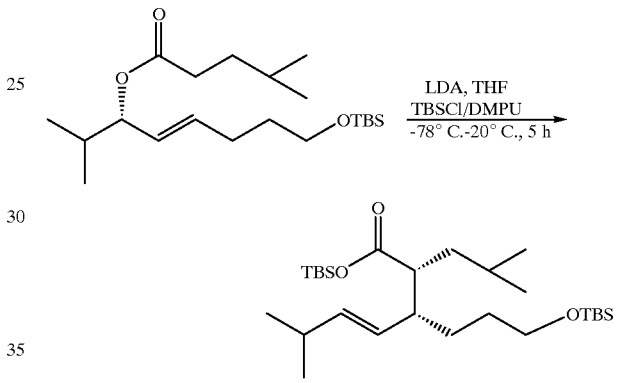

To a dry 500 mL 3-neck-round bottom flask equipped with a magnetic stirring bar, nitrogen inlet and outlet under nitrogen atmosphere was charged with 150 mL of dry THF and diisopropylamine (4.01 g, 39.63 mmol, 1.3 equivalent). The solution was cooled to 0° C. with stirring. To this solution, n-butyl lithium (39.6 mmol, 24.8 mL of 1.6 M solution in THF, 1.3 equivalent) was added slowly (in such a rate that internal temperature did not exceed 5° C.). The solution was stirred at 0° C. for 1 hour and then cooled to −78° C. The titled allylic ester (11.3 g, 30.5 mmol) in 35 mL THF solution was added very slowly (in such a rate that internal temperature did not exceed −72° C.) to the LDA solution with vigorous stirring. The reaction mixture was stirred for 45 minutes at −78° C. followed by the addition of TBSCl (5.05 g in 45 ml of THF, 33.5 mmol, 1.1 equivalent) slowly (internal temperature<−72° C.) and then DMPU (25 mL) slowly (internal temperature<−72° C.). The reaction mixture was stirred at −78° C. for 30 minutes, and then gradually warmed from −78° C. to −20° C. in a period of 5 hours. The reaction was then quenched with saturated ammonium chloride solution (150 mL) and extracted with hexane (3×150 ml). The combined organic phases were dried with anhydrous magnesium sulfate (10 g). Filtration to filtered magnesium sulfate, and the solvents were removed with rotoevaporate under reduced pressure. The residue was then dried under high vacuum to afford the crude product, which was purified by silicon gel chromatography to afford the desired product (12.5 g, 83% yield). The enantioselectivity: 94%ee (by GC), diastereoselectivity, anti/syn >20:1 (by NMR). $^{13}$C-NMR (ppm, free acid, CDCl3): 18.3, 21.5, 22.6, 23.6, 25.9, 26.4, 29.2, 30.5, 31.1, 38.8, 45.5, 48.7, 63.1, 127.7, 140.5, 181.7. $^1$H-NMR (300 MHz, ppm, CDCl3, J=Hz): −0.034 (s, 6H), 0.85 (dd, J=6.5, 6.5, 6H), 0.85, (s, 9H), 0.94 (d, J=22, 6H), 1.15~1.29 (m, 3H), 1.30~1.57 (m, 4H), 2.09 (m, 1H), 2.18~2.32 (m, 3H), 3.53 (t, J=5.3, 2H), 4.95 (dd, J=15.19, 7.79, 1H), 5.29 (dd, J=15.02, 7.79, 1H).

EXAMPLE 5
Preparation of Amide (VII-ii)

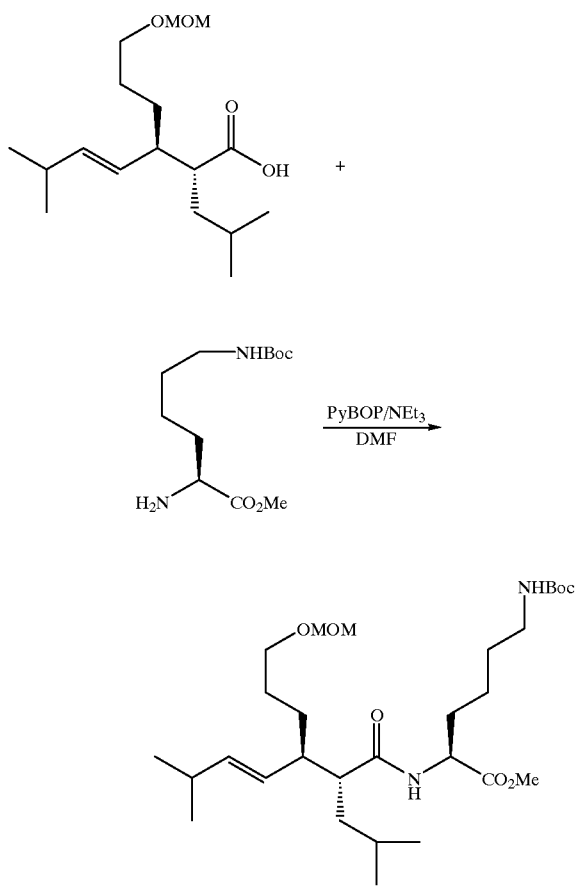

To a solution of the acid(2.4 g, 8 mmol) and ω-N-Boc-L-Lysine methyl ester hydrogen chloride salt(2.4 g, 8 mmol) in DMF(30 ml) cooled in an ice water bath was injected triethylamine(6.7 ml, 48 mmol) followed by addition of PyBop(4.70 g, 8 mmol). Stirring was continued at 0° C. for 2 hrs and rt for 3 hrs. The resulting mixture was diluted with EtOAc (150 ml) and then washed with aqueous NaHCO$_3$, brine, dried over Na$_2$SO$_4$. The EtOAc solution was concentrated and the residue was flush chromatographed on silica gel to afford the product as a white solid(3.59 g, 83%). Diastereomeric Excess: >95% by $^1$H NMR. $^1$H-NMR (CDCl$_3$): 6.04(1H, d), 5.40(1H, dd), 4.96(1H, dd), 4.76(1H, broad), 4.64(1H, m), 4.58(2H, s), 3.76(3H, s), 3.46(2H, m), 3.34(3H, s), 3.08(2H, q), 2.28(1H, m), 1.96–2.16(2H, m), 1.84(1H, m), 1.14–1.68(10, m), 1.46(9H, s), 0.98(6H, d), 0.86(6H, d). MS(ESI): 543(M+1).

EXAMPLE 6

Preparation of Aminoalcohol (VIII-a-i)

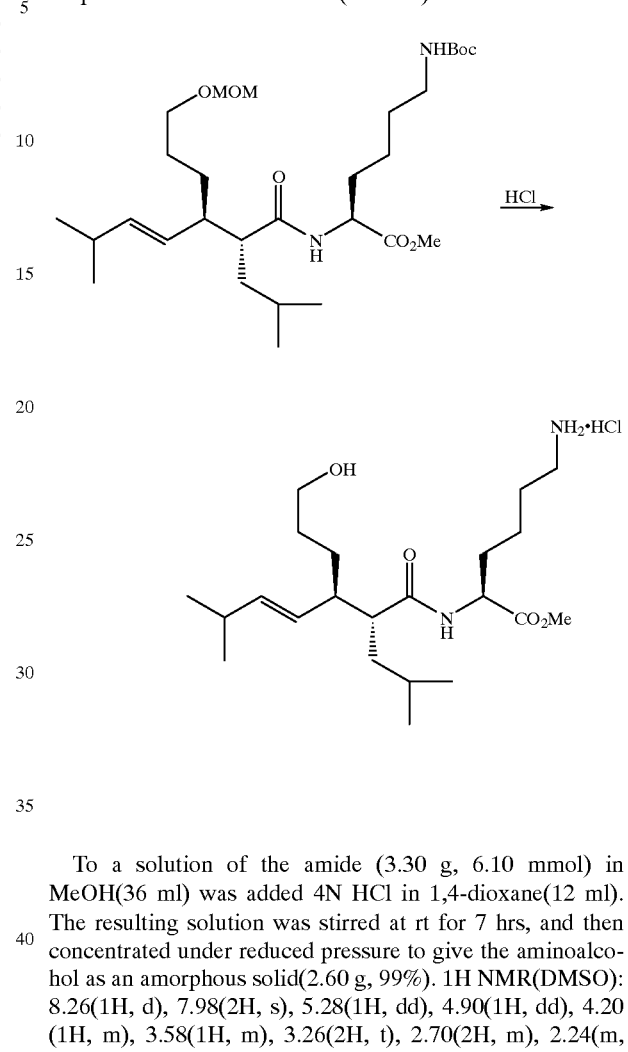

To a solution of the amide (3.30 g, 6.10 mmol) in MeOH(36 ml) was added 4N HCl in 1,4-dioxane(12 ml). The resulting solution was stirred at rt for 7 hrs, and then concentrated under reduced pressure to give the aminoalcohol as an amorphous solid(2.60 g, 99%). 1H NMR(DMSO): 8.26(1H, d), 7.98(2H, s), 5.28(1H, dd), 4.90(1H, dd), 4.20 (1H, m), 3.58(1H, m), 3.26(2H, t), 2.70(2H, m), 2.24(m, 1H), 2.10(1H, t), 1.82(1H, q), 1.00–1.70(13H, m), 0.92(6H, d), 0.78(3H, d), 0.74(3H, d). MS(ESI): 399(M+1).

EXAMPLE 7

Preparation of Cyclic Carbamate (IX-a-i)

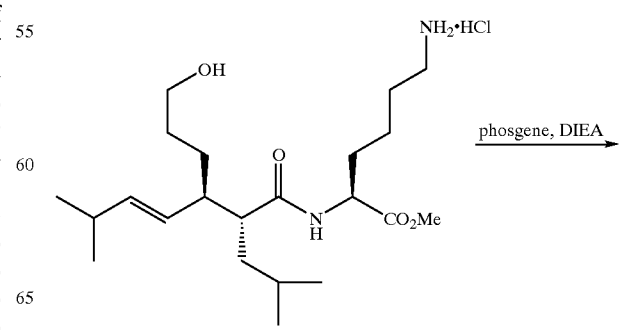

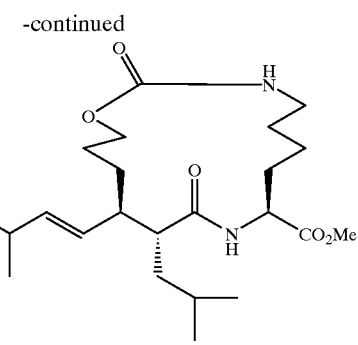

To a suspension of the aminoalcohol HCl salt(560 mg, 1.06 mmol) in THF(100 ml) cooled at −20° C. was added DIEA(0.58 ml). After stirring for 30 min, a solution of triphosgene(116 mg) in THF(10 ml) was injected, followed by the addition of a catalytic amount of dibutyltin dilaurate(5 mol%). The mixture was stirred at −20° C. for 5 hrs and then at rt overnight. After concentration, the solid residue was washed with hexane and further purified by flush chromatography using $CH_2Cl_2$ and MeOH as the eluent to afford the desired cyclic carbamate as a white solid(405 mg, 74%). 1H NMR(CDCl$_3$): 5.90(1H, d), 5.34 (1H, dd), 4.80(1H, dd), 4.80(2H, m), 4.40(1H, t), 3.78(1H, m), 3.68(3H, s), 3.38(1H, m), 2.94(1H, m), 2.20(2H, m), 1.80–2.04(3H, m), 0.94–1.60(10H, m), 0.90(6H, d), 0.88 (3H, d), 0.86(3H, d). MS(ESI): 425(M+1).

EXAMPLE 9

Preparation of Cyclophene (IX-i)

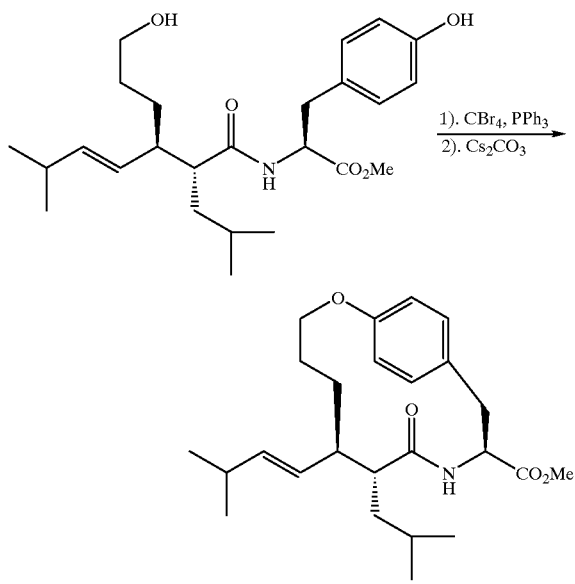

The phenol alcohol (530 mg, 1.22 mmol) and CBr$_4$(810 mg, 2.44 mmol) were mixed in THF (12 ml) and cooled with an ice water bath. To this solution was added a solution of PPh3(640 mg, 2.44 mmol) in THF(10 ml). The reaction mixture was stirred at rt overnight. After removal of THF, the residue chromatographed on silica gel using a mixture of EtOAc and Hexane as the eluent to afford the desired bromide as an amorphous solid(540 mg, 89%).

To a suspension of Cs$_2$CO$_3$(720 mg, 2.2 mmol) in DMF (13.2 ml) and DMSO(4.4 ml) heated at 60° C. was added a solution of the bromide(420 mg, 0.85 mmol) in DMF (6.5 ml). After addition, stirring was continued at 80° C. for 30 mins. The mixture was cooled down to to 0° C. with an ice-water bath and neutralized with citric acid. After removal of DMF and DMSO under reduced pressure, the residue was extracted with EtOAc and the EtOAc solution washed with NaHCO$_3$, brine, then dried. Chromatography after concentration on silica gel using a mixture of EtOAc and Hexane as the eluent gave a white solid(240 mg, 68%). $^1$H NMR (CDCl$_3$): 7.26(1H, d), 7.08(1H, d), 6.94(2H, s), 5.30(2H, m), 4.98(1H, m), 4.64(1H, dd), 4.20(1H, dd), 3.86(1H, m), 3.76(3H, s), 3.70(1H, dd), 2.60(1H, t), 2.24(1H, m), 1.86 (1H, m), 1.58(3H, m), 1.00–1.40(5H, m), 0.986(6H, d), 0.86(3H, d), 0.76(3H, d). MS(ESI), 416(M+1).

EXAMPLE 10

Preparation of Cyclic Carbamate Diacid Monomethyl Ester (X-a-i)

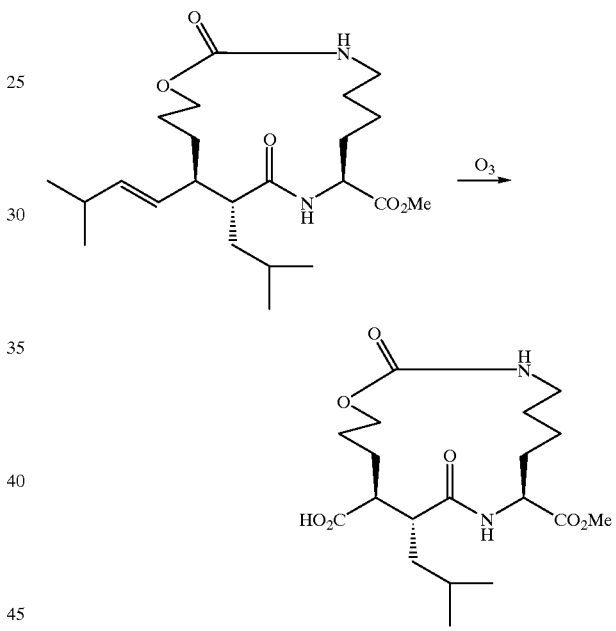

A solution of the cyclic carbamate (35 mg, 0.083 mmol) in methanol (5 ml) was cooled in an acetone-dry-ice bath. Into this solution was bubbled a O$_3$–O$_2$ flow. When the solution turned slightly blue, it was concentrated under reduced pressure. The residue thus obtained was dissolved in 4 ml of formic acid, followed by addition of 2 ml of 30% H2O2. The mixture was stirred at rt for 3 hrs. 1.8 g of sodium hydrobissulfite was added in portion. After addition, the reaction mixture was further stirred at rt for 30 mins (At this time peroxide test should be negative). After concentration, the residue was washed thoroughly with EtOAc and CH$_2$Cl$_2$. Concentration of the organic solution afforded a solid, which was further purified by plug-filtration. 26 mg of the product was obtained. 1H NMR (DMSO): 7.98(1H, d), 6.36(1H, s), 4.40(1H, m), 4.14(1H, m), 3.92(1H, d), 3.60 (3H, s), 3.04(2H, m), 2.50(1H, m), 2.20(1H, m), 1.30–1.80(13H, m), 0.88(3H, d), 0.82(3H, d). MS(ESI): 405(M+1).

Analyticla Methods

GC Test Method (Achiral)

For general analysis of reaction and products (Steps 1–3):
Chromatographic Conditions
- Column: J & W DB-17, 15 m×0.53 mm I.D., 1.0 um thick film thickness or equivalent
- Injector Temp.: 150° C.
- Detector Temp.: 280° C.
- Inlet Pressure: 2.8 psi
- Inlet Flow: 4 ml/min
- Stop time: 37.5 min
- Split Flow: splitless Oven Temperature Program
- Oven Initial Temp: 35° C. Time: 5 min
- Oven Program Rate: 15° C./min
- Oven Temperature: 240° C. Time: 2 min
- Oven Program Rate: 10° C./min
- Oven Temperature: 270° C. Time: 7 min Sample Preparation
- one drop of reaction mixture dissolved in ACN Approximate Retention Times
- Example 1: Propargyl-OH (II): 13.4 min Allyl-OH (III): 13.2 min
- Example 2: Allyl-ester (IV): 15.9 min
- Example 3: Claisen-silyl-ester (V): 15.5 min GC Test Method (chiral)

For the determination of silyl ester diastereomers following the Claisen rearrangement (step 3):
Chromatographic Conditions
- Column: J & W DB-17, 15 m×0.53 mm I.D., 1.0 um thick film thickness or equivalent
- Injector Temp.: 150° C.
- Detector Temp.: 280° C.
- Inlet Pressure: 2.8 psi
- Inlet Flow: 4 ml/min
- Stop time: 28.0 min
- Split Flow: splitless Oven Temperature Program
- Oven Initial Temp: 150° C. Time: 5 min
- Oven Program: 2° C./min→170° C. Time: 3 min
- Oven Program: 10° C./min→270° C.

Sample Preparation
- one drop of sample in acetonitrile

Approximate Retention Times
- Examples 3 and 4: Anti (silyl-ester): 15.1 min Syn (sylyl-ester): 15.6 min HPLC Method (Chiral)

Assay of Allyl Ester of step 1:
Chromatographic Conditions
- Column: Chiracel AD, 25 cm×4.6 mm i.d.
- Mobile Phase: 99% acetonitrile/1% isopropanol
- Flow rate: 1.0 mL/min
- Oven Temperature: 5° C.
- Injection volume: 5 uL
- Detection: 205 nm
- Stop time: 10 min
- Post time: 3 min Sample Preparation
- Sample Prep.: Dissolve sample into acetonitrile (eluent) and adjust concentration to approximately 1 mg/ml. The sample concentration may be adjusted to ensure the proper quantitation.

Retention Times
- Example 1: S enantiomer: 3.7 min R enantiomer: 4.0 min

HPLC Method (Achiral)

General method for monitoring of reactions and products of steps 4–7:
Column: 25 cm×4.6 mm id. Ultracarb 5 C8 (Phenomenex)
Mobile Phase: A: 0.1% trifluoroacetic acid in HPLC grade water B: 0.1% trifluoroacetic acid in HPLC grade acetonitrile

| Gradient: | t = 0 min | 60% A 40% B |
|---|---|---|
| | t = 5 min | 60% A 40% B |
| | t = 10 min | 60% A 40% B |
| | t = 15 min | 55% A 45% B |
| | t = 20 min | 50% A 50% B |
| | t = 25 min | 0% A 100% B |
| | t = 30 min | 0% A 100% B |

Flow Rate: 1.0 mL/min
Injection Volume: 5 microliters
Stop Time: 30 minutes
Oven Temp.: ambient
Detector: UV (220 nm)
Sample Prep.: Dissolve 25 mg of sample (dry solids weight) into the eluent and adjust concentration to approximately 1 mg/ml. Reaction aliquot (1–5 drops) may also be dissolved in eluent for monitoring reaction progression. The sample concentration may be adjusted to ensure the proper quantitation.

What is claimed is:
1. A process for the preparation of a compound of formula (VII):

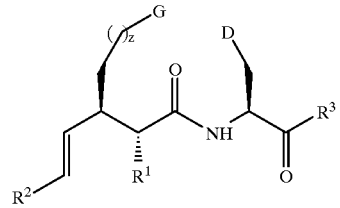

(VII)

or a salt form thereof;
wherein:
D is $P^1$—$NR^{11}$—$CH_2CH_2CH_2$—;
G is a halogen or —OP;
P is a suitable oxygen protecting group;
$P^1$ is a suitable nitrogen protecting group;
$R^1$ is selected from the group consisting of:
  $C_{1-5}$ alkyl substituted with 0–5 $R^{1a}$, —$(CH_2)_r$—$C_{3-10}$ cycloalkyl substituted with 0–5 $R^{1a}$, and —$(CH_2)_r$-aryl substituted with 0–5 $R^{1a}$;
$R^{1a}$ is selected independently at each occurrence from the group consisting of:
  hydrogen, —$CF_3$, —$CF_2CF_3$, —$NR^{1b}R^{1c}$, —$Si(R^{1d})_3$, $C_{1-5}$ alkyl, $C_{3-10}$ cycloalkyl, and aryl substituted with 0–5 $R^{1e}$;

$R^{1b}$ and $R^{1c}$ are selected independently at each occurrence from the group consisting of:
  $C_{1-5}$ alkyl, $C_{3-5}$ cycloalkyl and phenyl;
$R^{1d}$ is selected independently at each occurrence from the group consisting of:
  $C_{1-5}$ alkyl, $C_{1-5}$ haloalkyl, and aryl substituted with 0–5 $R^{1e}$;
$R^{1e}$ is selected independently at each occurrence from the group consisting of:
  $C_{1-5}$ alkyl, —(CH$_2$)$_r$—OR$^{1f}$, —OH, halo, —NH$_2$, and —(CF$_2$)$_r$CF$_3$;
$R^{1f}$ is selected independently at each occurrence from the group consisting of:
  $C_{1-5}$ alkyl, $C_{3-5}$ cycloalkyl and phenyl;
$R^2$ is selected from the group consisting of:
  $C_{1-10}$ alkyl, $C_{3-10}$ cycloalkyl, and —(CH$_2$)$_r$-phenyl substituted with 0–3 $R^{2a}$;
$R^{2a}$ is selected independently at each occurrence from the group consisting of:
  $C_{1-5}$ alkyl, —(CH$_2$)$_r$—OR$^{2b}$, —OH, halo, —NH$_2$, and —(CF$_2$)$_r$CF$_3$;
$R^{2b}$ is selected independently at each occurrence from the group consisting of:
  $C_{1-5}$ alkyl, $C_{3-5}$ cycloalkyl and phenyl;
$R^3$ is selected from the group consisting of:
  —OR$^4$, —NR$^5$R$^6$, —NR$^6$(OR$^5$), $C_{1-5}$ alkyl substituted with 0–3 $R^{3a}$, —(CH$_2$)$_r$-aryl substituted with 0–5 $R^{3a}$, and —(CH$_2$)$_r$-heterocyclic substituted with 0–3 $R^{3a}$;
$R^{3a}$ is selected independently at each occurrence from the group consisting of:
  hydrogen, $C_{1-5}$ alkyl, halo, hydroxy, —O—(CH$_2$)$_r$—R$^{3b}$, —(CH$_2$)$_r$—C(O)R$^{3b}$, —(CH$_2$)$_r$—SO$_2$NHR$^{3b}$, —(CH$_2$)$_r$—C(O)NHR$^{3b}$, —(CH$_2$)$_r$—OC(O)R$^{3b}$, —(CH$_2$)$_r$—NHSO$_2$R$^{3b}$, aryl, —(CH$_2$)$_r$—NHC(O)R$^{3b}$, and —(CH$_2$)$_r$—C(O)OR$^{3b}$;
$R^{3b}$ is selected independently at each occurrence from the group consisting of:
  $C_{1-5}$ alkyl, $C_{3-5}$ cycloalkyl and phenyl;
$R^4$ is selected from the group consisting of:
  hydrogen, $C_1$–$C_{10}$ alkyl, —(CH$_2$)$_r$—C$_{3-10}$ cycloalkyl, —(CH$_2$)$_r$-heterocyclic, and —(CH$_2$)$_r$-aryl substituted with 0–5 $R^{4a}$;
$R^{4a}$ is selected independently at each occurrence from the group consisting of:
  $C_{1-5}$ alkyl, —(CH$_2$)$_r$—OR$^{4b}$, —OH, halo, —NH$_2$, and —(CF$_2$)$_r$CF$_3$;
$R^{4b}$ is selected independently at each occurrence from the group consisting of:
  $C_{1-5}$ alkyl, $C_{3-5}$ cycloalkyl and phenyl;
$R^5$ is selected from the group consisting of:
  $C_1$–$C_5$ alkyl, —(CH$_2$)$_r$—$C_3$–$C_{10}$ cycloalkyl, —(CHR$^{5a}$Y)$_n$—R$^9$, —(CR$^7$R$^8$)$_n$—O—C(R$^7$R$^8$)$_r$—R$^9$, —(CR$^7$R$^8$)$_r$—R$^9$, and —(CR$^7$R$^8$)$_r$CONR$^7$R$^8$;
$R^{5a}$ is selected independently at each occurrence from the group consisting of:
  hydrogen, $C_{1-10}$ alkyl substituted with 0–3 $R^{5b}$, —(CH$_2$)$_r$-aryl substituted with 0–3 $R^{5b}$, and —(CH$_2$)$_r$—O—(CH$_2$)$_r$-aryl substituted with 0–3 $R^{5b}$;
$R^{5b}$ is selected independently at each occurrence from the group consisting of:
  hydrogen, halo, hydroxy, —OR$^{5c}$, —NHC(O)CH$_3$, -aryl-(CH$_2$)$_r$—NH$_2$, -aryl-(CH$_2$)$_r$-aryl, $C_{1-10}$ alkyl substituted with 0–3 $R^{5d}$, and —(CH$_2$)$_r$-aryl substituted with 0–3 $R^{5d}$;
$R^{5c}$ is selected independently at each occurrence from the group consisting of:
  $C_{1-5}$ alkyl, $C_{3-5}$ cycloalkyl and phenyl;
$R^{5d}$ is selected independently at each occurrence from the group consisting of;
  hydrogen, $C_{1-5}$ alkyl, —O—(CH$_2$)$_r$—R$^{5e}$, —OH, halo, —NHC(O)CH$_3$, and —C(O)NH$_2$;
$R^{5e}$ is selected independently at each occurrence from the group consisting of:
  $C_{1-5}$ alkyl, $C_{3-5}$ cycloalkyl and phenyl;
$R^6$ is selected from the group consisting of:
  hydrogen, $C_1$–$C_{10}$ alkyl, —(CH$_2$)$_r$-aryl, —(CH$_2$)$_r$—C(O)R$^{6a}$, —(CH$_2$)$_r$-heterocyclic, and phenyl substituted with 0–5 $R^{6c}$;
$R^{6a}$ is selected independently at each occurrence from the group consisting of;
  hydrogen, $C_{1-5}$ alkyl, —O—(CH$_2$)$_r$—R$^{6b}$, —OH, halo, —NHC(O)CH$_3$, and —C(O)NH$_2$;
$R^{6b}$ is selected independently at each occurrence from the group consisting of:
  $C_{1-5}$ alkyl, $C_{3-5}$ cycloalkyl and phenyl;
$R^{6c}$ is selected independently at each occurrence from the group consisting of:
  halogen, NO$_2$, —R$^{6d}$, and —O—(CH$_2$)$_r$—R$^{6d}$;
$R^{6d}$ is selected independently at each occurrence from the group consisting of:
  $C_{1-5}$ alkyl, $C_{3-5}$ cycloalkyl and phenyl;
alternatively, $R^5$ and $R^6$ combine to form a 3—to 8— membered heterocyclic ring containing 1 to 3 additional heteroatoms selected from —O—, —NR$^6$—, —S(O)p-, and —C(O)—, optionally fused to a phenyl ring;
$R^7$ and $R^8$ may be H or $R^{5a}$;
alternatively, $R^7$ and $R^8$ combine to form 3 to 7 membered heterocyclic ring substituted with 1–3 $R^{7a}$, containing 1–3 additional heteroatoms selected from —O—, —S(O)p-, and —NR$^6$—, optionally fused to an aryl ring substituted with 0–3 $R^{7c}$;
$R^{7a}$ is selected independently at each occurrence from the group consisiting of:
  hydrogen, $C_{1-5}$ alkyl, $C_{3-5}$ cycloalkyl, hydroxy, halo, —OR$^{7b}$, —NHC(O)CH$_3$, —C(O)NH$_2$, and aryl;
$R^{7b}$ is selected independently at each occurrence from the group consisting of:
  $C_{1-5}$ alkyl, $C_{1-5}$ cycloalkyl and phenyl;
$R^{7c}$ is selected independently at each occurrence from the group consisting of;
  hydrogen, $C_{1-5}$ alkyl, $C_{3-5}$ cycloalkyl, hydroxy, halo, —O(CH$_2$)$_r$—R$^{7d}$, —NHC(O)CH$_3$, —C(O)NH$_2$, and aryl;
$R^{7d}$ is selected independently at each occurrence from the group consisting of:
  $C_{1-5}$ alkyl, $C_{1-5}$ cycloalkyl and phenyl;
$R^9$ is selected from the group consisting of:
  hydrogen, $C_{1-5}$ alkyl, —C(O)OC$_{1-5}$ alkyl, —(CH$_2$)$_r$-aryl substituted with 0–3 $R^{9a}$, and a 5 or 6 membered heterocyclic ring containing from 0 to 2 N, O or S(O)p, and substituted with 0–3 $R^{9a}$;
$R^{9a}$ is selected from the group consisting of:
  —OH, —O—(CH$_2$)$_r$—R$^{9b}$, —C(O)OR$^{9b}$, —NHR$^{10}$ and aryl;

$R^{9b}$ is selected from the group consisting of:
  $C_{1-5}$ alkyl, $C_{1-5}$ cycloalkyl and phenyl;
$R^{10}$ is independently at each occurrence H or $C_{1-10}$ alkyl substituted with 0–3 $R^{10a}$;
$R^{10a}$ is selected independently at each occurrence from the group consisting of:
  hydrogen, $C_1$–$C_{10}$ alkyl substituted with 0–3 $R^{10b}$, and —$(CH_2)_r$-aryl substituted with 0–3 $R^{10b}$;
$R^{10b}$ is selected independently at each occurrence from the group consisting of:
  hydrogen, halo, hydroxy, —$OR^{10c}$, —$NHC(O)CH_3$, —$(CH_2)_r$—$C(O)NH_2$, -aryl-$NH_2$, and —$SO_2NH_2$;
$R^{10c}$ is selected independently at each occurrence from the group consisting of:
  $C_{1-5}$ alkyl, $C_{1-5}$ cycloalkyl and phenyl;
$R^{11}$ is selected independently at each occurrence from the group consisting of:
  hydrogen, $C_1$–$C_{10}$ alkyl substituted with 0–3 $R^{11a}$, and —$(CH_2)_r$-aryl substituted with 0–3 $R^{11a}$;
$R^{11a}$ is selected independently at each occurrence from the group consisting of:
  hydrogen, halo, hydroxy, —$OR^{11b}$, —$NHC(O)CH_3$, —$(CH_2)_r$—$C(O)NH_2$, -aryl-$NH_2$, and —$SO_2NH_2$;
$R^{11b}$ is selected independently at each occurrence from the group consisting of:
  $C_{1-5}$ alkyl, $C_{1-5}$ cycloalkyl and phenyl;
n is selected from 1, 2 and 3;
p is selected independently at each occurrence from 0, 1 and 2;
r is selected independently at each occurrence from 0, 1, 2, and 3;
Y is selected from the group consisting of:
  —$CONR^{10}$—, —$NR^{10}CO$—, —$SO_2NR^{10}$—, —$NR^{10}SO_2$—, and a 5 membered heterocyclic ring; and
z is selected from 1, 2, 3, 4 and 5;
the process comprising:
contacting a compound of formula (IV):

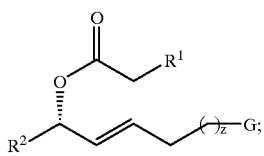

(IV)

wherein the double bond is in the E configuration; with a silylating agent in the presence of a strong base to give a compound of formula (IV-a):

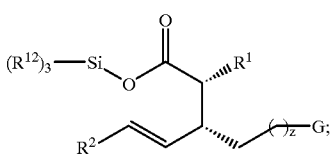

(IV-a)

wherein $R^{12}$ is selected independently at each occurrence from $C_{1-6}$ alkyl and phenyl;
contacting the compound of formula (IV-a) with hydroxide to form a compound of formula (V):

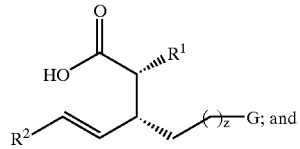

(V)

coupling the compound of formula (V) with a compound of the formula (VI):

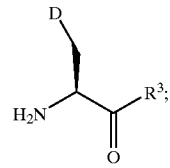

(VI)

to form a compound of formula (VII), or a salt form thereof.

2. The process of claim 1, wherein the compound of formula (IV) is prepared by the process comprising:
reducing a compound of the formula (II):

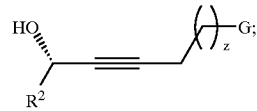

(II)

to form a compound of the formula (III):

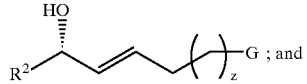

(III)

acylating the compound of formula (III) to form a compound of formula (IV).

3. The process of claim 1, wherein:
P is tert-butyldimethylsilyl or methoxymethyl;
$P^1$ is tert-butyloxycarbonyl;
$R^1$ is $C_{1-5}$ alkyl;
$R^2$ is selected from the group consisting of:
  $C_{1-10}$ alkyl, $C_{3-10}$ cycloalkyl, and —$(CH_2)_r$-phenyl;
$R^3$ is —$OR^4$ or —$NR^5R^6$
$R^4$ is selected from the group consisting of:
  hydrogen, $C_{1-10}$ alkyl, —$(CH_2)_r$—$C_{3-10}$ cycloalkyl, and —$(CH_2)_r$-phenyl;
$R^5$ is selected from the group consisting of:
  $C_{1-5}$ alkyl, —$(CH_2)_r$—$C_{3-10}$ cycloalkyl, —$CH_2$—$CONHR^{10}$, —$CH_2$—$C(O)OC_{1-5}$ alkyl, —$CH_2$—$CONR^7R^8$, and —$(CH_2)_r$-phenyl;
$R^6$ is selected from hydrogen or $C_1$–$C_{10}$ alkyl;
$R^7$ and $R^8$ form a 6 membered saturated ring containing —O— and —$NR^6$—;
$R^{10}$ is H or $C_{1-5}$ alkyl;
$R^{11}$ is selected from the group consisting of:
  hydrogen, $C_1$–$C_{10}$ alkyl, and phenyl;
r is selected from 0, 1, and 2; and
z is 2.

4. The process of claim 3, wherein:
the silylating agent is trimethylsilylchloride or t-butyldimethylsilylchloride;
the strong base is lithium diisopropylamide or lithium hexamethyldisilazide; and
coupling comprises contacting a compound of formula (V) with a compound of formula (VI) in the presence of a coupling agent selected from the group consisting of:
dicyclohexylcarbodiimide, carbonyldiimidazole, 1-(3-dimethylaminopropyl)-3-ethylcarbodiimide, O-(1H-benzotriazol-1-yl)-N,N,N',N'-tetra-methyluronium tetrafluoroborate, benzotriazol-1-yl-oxy-tri-pyrrolidinophosphonium hexafluorophosphate and benzotriazol-1-yl-oxy-tris-dimethylamino-phosphonium hexafluorophosphate.

5. The process of claim 4, wherein:
$R^1$ is —$CH_2CH(CH_3)_2$;
$R^2$ is —$CH(CH_3)_2$;
$R^3$ is selected from the group consisting of:
—$OC_{1-5}$ alkyl, —$NHCH_2C(O)OC_{1-5}$ alkyl, —$NHCH_2C(O)NR^7R^8$ and —$NHCH_2C(O)NHCH_3$; and
$R^7$ and $R^8$ are taken together to form a morpholine ring.

6. A process for the preparation of a compound of formula (X-a):

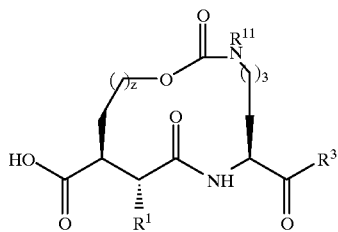

(X-a)

or a pharmaceutically acceptable salt form thereof, wherein:
$R^1$ is selected from the group consisting of:
$C_{1-5}$ alkyl substituted with 0–5 $R^{1a}$, —$(CH_2)_r$—$C_{3-10}$ cycloalkyl substituted with 0–5 $R^{1a}$, and —$(CH_2)_r$-aryl substituted with 0–5 $R^{1a}$;
$R^{1a}$ is selected independently at each occurrence from the group consisting of:
hydrogen, —$CF_3$, —$CF_2CF_3$, —$NR^{1b}R^{1c}$, —$Si(R^{1d})_3$, $C_{1-5}$ alkyl, $C_{3-10}$ cycloalkyl, and aryl substituted with 0–5 $R^{1e}$;
$R^{1b}$ and $R^{1c}$ are selected independently at each occurrence from the group consisting of:
$C_{1-5}$ alkyl, $C_{3-5}$ cycloalkyl and phenyl;
$R^{1d}$ is selected independently at each occurrence from the group consisting of:
$C_{1-5}$ alkyl, $C_{1-5}$ haloalkyl, and aryl substituted with 0–5 $R^{1e}$;
$R^{1e}$ is selected independently at each occurrence from the group consisting of:
$C_{1-5}$ alkyl, —$(CH_2)_r$—$OR^{1f}$, —OH, halo, —$NH_2$, and —$(CF_2)_rCF_3$;
$R^{1f}$ is selected independently at each occurrence from the group consisting of:
$C_{1-5}$ alkyl, $C_{3-5}$ cycloalkyl and phenyl;
$R^3$ is selected from the group consisting of:
—$OR^4$, —$NR^5R^6$, —$NR^6(OR^5)$, $C_{1-5}$ alkyl substituted with 0–3 $R^{3a}$, —$(CH_2)_r$-aryl substituted with 0–5 $R^{3a}$, and —$(CH_2)_r$-heterocyclic substituted with 0–3 $R^{3a}$;

$R^{3a}$ is selected independently at each occurrence from the group consisting of:
hydrogen, $C_{1-5}$ alkyl, halo, hydroxy, —O—$(CH_2)_r$—$R^{3b}$, —$(CH_2)_r$—$C(O)R^{3b}$, —$(CH_2)_r$—$SO_2NHR^{3b}$, —$(CH_2)_r$—$C(O)NHR^{3b}$, —$(CH_2)_r$—$OC(O)R^{3b}$, —$(CH_2)_r$—$NHSO_2R^{3b}$, aryl, —$(CH_2)_r$—$NHC(O)R^{3b}$, and —$(CH_2)_r$—$C(O)OR^{3b}$;
$R^{3b}$ is selected independently at each occurrence from the group consisting of:
$C_{1-5}$ alkyl, $C_{3-5}$ cycloalkyl and phenyl;
$R^4$ is selected from the group consisting of:
hydrogen, $C_1$–$C_{10}$ alkyl, —$(CH_2)_r$—$C_{3-10}$ cycloalkyl, —$(CH_2)_r$-heterocyclic, and —$(CH_2)_r$-aryl substituted with 0–5 $R^{4a}$;
$R^{4a}$ is selected independently at each occurrence from the group consisting of:
$C_{1-5}$ alkyl, —$(CH_2)_r$—$OR^{4b}$, —OH, halo, —$NH_2$, and —$(CF_2)_rCF_3$;
$R^{4b}$ is selected independently at each occurrence from the group consisting of:
$C_{1-5}$ alkyl, $C_{3-5}$ cycloalkyl and phenyl;
$R^5$ is selected from the group consisting of:
$C_1$–$C_5$ alkyl, —$(CH_2)_r$—$C_3$–$C_{10}$ cycloalkyl, —$(CHR^{5a}Y)_n$—$R^9$, —$(CR^7R^8)_n$—O—$C(R^7R^8)_r$—$R^9$, —$(CR^7R^8)_r$—$R^9$, and —$(CR^7R^8)_r CONR^7R^8$;
$R^{5a}$ is selected independently at each occurrence from the group consisting of:
hydrogen, $C_{1-10}$ alkyl substituted with 0–3 $R^{5b}$, —$(CH_2)_r$-aryl substituted with 0–3 $R^{5b}$, and —$(CH_2)_r$—O—$(CH_2)_r$-aryl substituted with 0–3 $R^{5b}$;
$R^{5b}$ is selected independently at each occurrence from the group consisting of:
hydrogen, halo, hydroxy, —$OR^{5c}$, —$NHC(O)CH_3$, -aryl-$(CH_2)_r$—$NH_2$, -aryl-$(CH_2)_r$-aryl, $C_{1-10}$ alkyl substituted with 0–3 $R^{5d}$, and —$(CH_2)_r$-aryl substituted with 0–3 $R^{5d}$;
$R^{5c}$ is selected independently at each occurrence from the group consisting of:
$C_{1-5}$ alkyl, $C_{3-5}$ cycloalkyl and phenyl;
$R^{5d}$ is selected independently at each occurrence from the group consisting of;
hydrogen, $C_{1-5}$ alkyl, —O—$(CH_2)_r$—$R^{5e}$, —OH, halo, —$NHC(O)CH_3$, and —$C(O)NH_2$;
$R^{5e}$ is selected independently at each occurrence from the group consisting of:
$C_{1-5}$ alkyl, $C_{3-5}$ cycloalkyl and phenyl;
$R^6$ is selected from the group consisting of:
hydrogen, $C_1$–$C_{10}$ alkyl, —$(CH_2)_r$-aryl, —$(CH_2)_r$—$C(O)R^{6a}$, —$(CH_2)_r$-heterocyclic and phenyl substituted with 0–5 $R^{6c}$;
$R^{6a}$ is selected independently at each occurrence from the group consisting of;
hydrogen, $C_{1-5}$ alkyl, —O—$(CH_2)_r$—$R^{6b}$, —OH, halo, —$NHC(O)CH_3$, and —$C(O)NH_2$;
$R^{6b}$ is selected independently at each occurrence from the group consisting of:
$C_{1-5}$ alkyl, $C_{3-5}$ cycloalkyl and phenyl;
$R^{6c}$ is selected independently at each occurrence from the group consisting of:
halogen, $NO_2$, —$R^{6d}$, and —O—$(CH_2)_r$—$R^{6d}$;
$R^{6d}$ is selected independently at each occurrence from the group consisting of:
$C_{1-5}$ alkyl, $C_{3-5}$ cycloalkyl and phenyl;

alternatively, $R^5$ and $R^6$ combine to form a 3- to 8- membered heterocyclic ring containing 1 to 3 additional heteroatoms selected from —O—, —$NR^6$—, —S(O)p-, and —C(O)—, optionally fused to a phenyl ring;

$R^7$ and $R^8$ may be H or $R^{5a}$;

alternatively, $R^7$ and $R^8$ combine to form 3- to 7- membered heterocyclic ring substituted with 1–3 $R^{7a}$, containing 1–3 additional heteroatoms selected from —O—, —S(O)p-, and —$NR^6$—, optionally fused to an aryl ring substituted with 0–3 $R^{7c}$;

$R^{7a}$ is selected independently at each occurrence from the group consisiting of:
hydrogen, $C_{1-5}$ alkyl, $C_{3-5}$ cycloalkyl, hydroxy, halo, —$OR^{7b}$, —$NHC(O)CH_3$, —$C(O)NH_2$, and aryl;

$R^{7b}$ is selected independently at each occurrence from the group consisting of:
$C_{1-5}$ alkyl, $C_{1-5}$ cycloalkyl and phenyl;

$R^{7c}$ is selected independently at each occurrence from the group consisting of;
hydrogen, $C_{1-5}$ alkyl, $C_{3-5}$ cycloalkyl, hydroxy, halo, —$O(CH_2)_r$—$R^{7d}$, —$NHC(O)CH_3$, —$C(O)NH_2$, and aryl;

$R^{7d}$ is selected independently at each occurrence from the group consisting of:
$C_{1-5}$ alkyl, $C_{1-5}$ cycloalkyl and phenyl;

$R^9$ is selected from the group consisting of:
hydrogen, $C_{1-5}$ alkyl, —$C(O)OC_{1-5}$ alkyl, —$(CH_2)_r$-aryl substituted with 0–3 $R^{9a}$, and a 5- or 6- membered heterocyclic ring containing from 0 to 2 N, O or S(O)p, and substituted with 0–3 $R^{9a}$;

$R^{9a}$ is selected from the group consisting of:
—OH, —O—$(CH_2)_r$—$R^{9b}$, —$C(O)OR^{9b}$, $NHR^{10}$ and aryl;

$R^{9b}$ is selected from the group consisting of:
$C_{1-5}$ alkyl, $C_{1-5}$ cycloalkyl and phenyl;

$R^{10}$ is independently at each occurrence H or $C_{1-10}$ alkyl substituted with 0–3 $R^{10a}$;

$R^{10a}$ is selected independently at each occurrence from the group consisting of:
hydrogen, $C_1$–$C_{10}$ alkyl substituted with 0–3 $R^{10b}$, and —$(CH_2)_r$-aryl substituted with 0–3 $R^{10b}$;

$R^{10b}$ is selected independently at each occurrence from the group consisting of:
hydrogen, halo, hydroxy, —$OR^{10c}$, —$NHC(O)CH_3$, —$(CH_2)_r$—$C(O)NH_2$, -aryl-$NH_2$, and —$SO_2NH_2$;

$R^{10c}$ is selected independently at each occurrence from the group consisting of:
$C_{1-5}$ alkyl, $C_{1-5}$ cycloalkyl and phenyl;

$R^{11}$ is selected independently at each occurrence from the group consisting of:
hydrogen, $C_1$–$C_{10}$ alkyl substituted with 0–3 $R^{11a}$, and —$(CH_2)_r$-aryl substituted with 0–3 $R^{11a}$;

$R^{11a}$ is selected independently at each occurrence from the group consisting of:
hydrogen, halo, hydroxy, —$OR^{11b}$, —$NHC(O)CH_3$, —$(CH_2)_r$—$C(O)NH_2$, -aryl-$NH_2$, and —$SO_2NH_2$;

$R^{11b}$ is selected independently at each occurrence from the group consisting of:
$C_{1-5}$ alkyl, $C_{1-5}$ cycloalkyl and phenyl;

n is selected from 1, 2 and 3;

p is selected independently at each occurrence from 0, 1 and 2;

r is selected independently at each occurrence from 0, 1, 2, and 3;

Y is selected from the group consisting of:
—$CONR^{10}$—, —$NR^{10}CO$—, —$SO_2NR^{10}$—, —$NR^{10}SO_2$—, and a 5 membered heterocyclic ring; and z is selected from 1, 2, 3, 4 and 5;

the process comprising:

cyclizing a compound of formula (VIII-a):

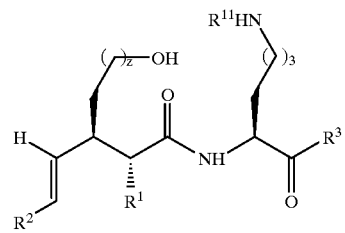

(VIII-a)

or a salt form thereof;

wherein:
$R^2$ is selected from the group consisting of:
$C_{1-10}$ alkyl, $C_{3-10}$ cycloalkyl, and —$(CH_2)_r$-phenyl substituted with 0–3 $R^{2a}$;

$R^{2a}$ is selected independently at each occurrence from the group consisting of:
$C_{1-5}$ alkyl, —$(CH_2)_r$—$OR^{2b}$, —OH, halo, —$NH_2$, and —$(CF_2)_rCF_3$;

$R^{2b}$ is selected independently at each occurrence from the group consisting of:
$C_{1-5}$ alkyl, $C_{3-5}$ cycloalkyl and phenyl;

to form a compound of formula (IX-a):

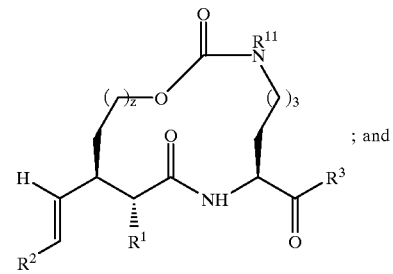

(IX-a)

; and contacting the compound of formula (IX-a) with an oxidizing agent to form a compound of formula (X-a) or a pharmaceutically acceptable salt form thereof.

7. The process of claim 6, wherein:

$R^1$ is $C_{1-5}$ alkyl;

$R^2$ is selected from the group consisting of:
$C_{1-10}$ alkyl, $C_{3-10}$ cycloalkyl, and —$(CH_2)_r$-phenyl;

$R^3$ is —$OR^4$ or —$NR^5R^6$;

$R^4$ is selected from the group consisting of:
hydrogen, $C_{1-10}$ alkyl, —$(CH_2)_r$—$C_{3-10}$ cycloalkyl, and —$(CH_2)_r$-phenyl;

$R^5$ is selected from the group consisting of:
$C_{1-5}$ alkyl, —$(CH_2)_r$—$C_{3-10}$ cycloalkyl, —$CH_2$—$CONHR^{10}$, —$CH_2$—$C(O)OC_{1-5}$ alkyl, —$CH_2$—$CONR^7R^8$, and —$(CH_2)_r$-phenyl;

$R^6$ is selected from hydrogen or $C_1$–$C_{10}$ alkyl;

$R^7$ and $R^8$ form a 6 membered saturated ring containing —O— or —$NR^6$—;

$R^{10}$ is H or $C_{1-5}$ alkyl;

$R^{11}$ is selected from the group consisting of:
hydrogen, $C_1$–$C_{10}$ alkyl, and phenyl;
r is selected from 0, 1, or 2;
z is 2;
cyclizing comprises contacting the free base of the compound of formula (VII-a) with phosgene or triphosgene in the presence of an acid scavenger; and
the oxidizing agent is $KMnO_4$ in $NaIO_4$ or ozone.

8. The process of claim 6, wherein:
$R^1$ is —$CH_2CH(CH_3)_2$;
$R^2$ is —$CH(CH_3)_2$; and,
$R^3$ is selected from the group consisting of:
—$OC_{1-5}$ alkyl, —$NHCH_2C(O)OC_{1-5}$ alkyl, —$NHCH_2C(O)NR^7R^8$ and —$NHCH_2C(O)NHCH_3$;
$R^7$ and $R^8$ are taken together to form a morpholine ring;
cyclizing comprises contacting the free base of the compound of formula (VII-a) with phosgene or triphosgene in the presence of an acid scavenger selected from the group consisting of:
triethylamine, diisopropylethylamine, and pyridine; and
the oxidizing agent is ozone.

9. The process of claim 8, wherein $R^3$ is —$OCH_3$.

10. A compound of formula (III):

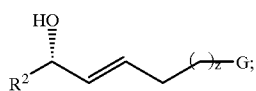
(III)

wherein:
$R^2$ is —$CH(CH_3)_2$;
G is —$OCH_2OCH_3$; and
z is 2.

11. A compound of formula (IV):

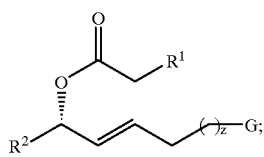
(IV)

wherein:
$R^1$ is —$CH_2CH(CH_3)_2$
$R^2$ is —$CH(CH_3)_2$;
G is —$OCH_2OCH_3$; and
z is 2.

12. A compound of formula (IV-a):

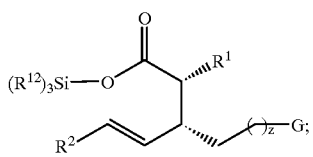
(IV-a)

wherein:
$R^1$ is —$CH_2CH(CH_3)_2$;
$R^2$ is —$CH(CH_3)_2$;
$R^{12}$ is selected independently at each occurrence from $C_{1-6}$ alkyl or phenyl;

G is —$OCH_2OCH_3$ or —O-t-butyldimethylsilyl; and
z is 2.

13. A compound of formula (V):

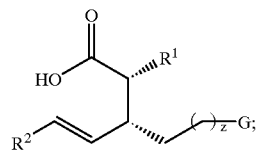
(V)

or a form thereof;
wherein:
$R^1$ is —$CH_2CH(CH_3)_2$;
$R^2$ is —$CH(CH_3)_2$;
G is —$OCH_2OCH_3$ or —O-t-butyldimethylsilyl; and
z is 2.

14. A compound of formula (VII):

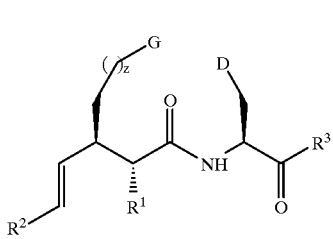
(VII)

or a salt form thereof;
wherein:
D is $P^1$—$NR^{11}$—$CH_2CH_2CH_2$—;
G is selected from the group consisting:
halogen, —OP or —OH;
P is a suitable oxygen protecting group;
$P^1$ is a suitable nitrogen protecting group;
$R^1$ is selected from the group consisting of:
$C_{1-5}$ alkyl substituted with 0–5 $R^{1a}$, —$(CH_2)_r$—$C_{3-10}$ cycloalkyl substituted with 0–5 $R^{1a}$, and —$(CH_2)_r$-aryl substituted with 0–5 $R^{1a}$;
$R^{1a}$ is selected independently at each occurrence from the group consisting of: hydrogen, —$CF_3$, —$CF_2CF_3$, —$NR^{1b}R^{1c}$, —$Si(R^{1d})_3$, $C_{1-5}$ alkyl, $C_{3-10}$ cycloalkyl, and aryl substituted with 0–5 $R^{1e}$;
$R^{1b}$ and $R^{1c}$ are selected independently at each occurrence from the group consisting of:
$C_{1-5}$ alkyl, $C_{3-5}$ cycloalkyl and phenyl;
$R^{1d}$ is selected independently at each occurrence from the group consisting of:
$C_{1-5}$ alkyl, $C_{1-5}$ haloalkyl, and aryl substituted with 0–5 $R^{1e}$;
$R^{1e}$ is selected independently at each occurrence from the group consisting of:
$C_{1-5}$ alkyl, —$(CH_2)_r$—$OR^{1f}$, —OH, halo, —$NH_2$, and —$(CF_2)_rCF_3$;
$R^{1f}$ is selected independently at each occurrence from the group consisting of:
$C_{1-5}$ alkyl, $C_{3-5}$ cycloalkyl and phenyl;
$R^2$ is selected from the group consisting of:
$C_{1-10}$ alkyl, $C_{3-10}$ cycloalkyl, and —$(CH_2)_r$-phenyl substituted with 0–3 $R^{2a}$;
$R^{2a}$ is selected independently at each occurrence from the group consisting of:

$C_{1-5}$ alkyl, —$(CH_2)_r$—$OR^{2b}$, —OH, halo, —$NH_2$, and —$(CF_2)_rCF_3$;

$R^{2b}$ is selected independently at each occurrence from the group consisting of:
  $C_{1-5}$ alkyl, $C_{3-5}$ cycloalkyl and phenyl;

$R^3$ is selected from the group consisting of:
  —$OR^4$, —$NR^5R^6$, —$NR^6(OR^5)$, $C_{1-5}$ alkyl substituted with 0–3 $R^{3a}$, —$(CH_2)_r$-aryl substituted with 0–5 $R^{3a}$, and —$(CH_2)_r$-heterocyclic substituted with 0–3 $R^{3a}$;

$R^{3a}$ is selected independently at each occurrence from the group consisting of:
  hydrogen, $C_{1-5}$ alkyl, halo, hydroxy, —O—$(CH_2)_r$—$R^{3b}$, —$(CH_2)_r$—$C(O)R^{3b}$, —$(CH_2)_r$—$SO_2NHR^{3b}$, —$(CH_2)_r$—$C(O)NHR^{3b}$, —$(CH_2)_r$—$OC(O)R^{3b}$, —$(CH_2)_r$—$NHSO_2R^{3b}$, aryl, —$(CH_2)_r$—NHC(O)$R^{3b}$, and —$(CH_2)_r$—$C(O)OR^{3b}$;

$R^{3b}$ is selected independently at each occurrence from the group consisting of:
  $C_{1-5}$ alkyl, $C_{3-5}$ cycloalkyl and phenyl;

$R^4$ is selected from the group consisting of:
  hydrogen, $C_1$–$C_{10}$ alkyl, —$(CH_2)_r$—$C_{3-10}$ cycloalkyl, —$(CH_2)_r$-heterocyclic, and —$(CH_2)_r$-aryl substituted with 0–5 $R^{4a}$;

$R^{4a}$ is selected independently at each occurrence from the group consisting of:
  $C_{1-5}$ alkyl, —$(CH_2)_r$—$OR^{4b}$, —OH, halo, —$NH_2$, and —$(CF_2)_rCF_3$;

$R^{4b}$ is selected independently at each occurrence from the group consisting of:
  $C_{1-5}$ alkyl, $C_{3-5}$ cycloalkyl and phenyl;

$R^5$ is selected from the group consisting of:
  $C_{1-5}$ alkyl, —$(CH_2)_r$—$C_{3-10}$ cycloalkyl, —$(CHR^{5a}Y)_n$—$R^9$, —$(CR^7R^8)_n$—O—$C(R^7R^8)_r$—$R^9$, —$(CR^7R^8)_r$—$R^9$, and —$(CR^7R^8)_rCONR^7R^8$;

$R^{5a}$ is selected independently at each occurrence from the group consisting of:
  hydrogen, $C_{1-10}$ alkyl substituted with 0–3 $R^{5b}$, —$(CH_2)_r$-aryl substituted with 0–3 $R^{5b}$, and —$(CH_2)_r$—O—$(CH_2)_r$-aryl substituted with 0–3 $R^{5b}$;

$R^{5b}$ is selected independently at each occurrence from the group consisting of:
  hydrogen, halo, hydroxy, —$OR^{5c}$, —$NHC(O)CH_3$, -aryl-$(CH_2)_r$—$NH_2$, -aryl-$(CH_2)_r$-aryl, $C_{1-10}$ alkyl substituted with 0–3 $R^{5d}$, and —$(CH_2)_r$-aryl substituted with 0–3 $R^{5d}$;

$R^{5c}$ is selected independently at each occurrence from the group consisting of:
  $C_{1-5}$ alkyl, $C_{3-5}$ cycloalkyl and phenyl;

$R^{5d}$ is selected independently at each occurrence from the group consisting of;
  hydrogen, $C_{1-5}$ alkyl, —O—$(CH_2)_r$—$R^{5e}$, —OH, halo, —$NHC(O)CH_3$, and —$C(O)NH_2$;

$R^{5e}$ is selected independently at each occurrence from the group consisting of:
  $C_{1-5}$ alkyl, $C_{3-5}$ cycloalkyl and phenyl;

$R^6$ is selected from the group consisting of:
  hydrogen, $C_1$–$C_{10}$ alkyl, —$(CH_2)_r$-aryl, —$(CH_2)_r$—$C(O)R^{6a}$, —$(CH_2)_r$-heterocyclic, and phenyl substituted with 0–5 $R^{6c}$;

$R^{6a}$ is selected independently at each occurrence from the group consisting of;
  hydrogen, $C_{1-5}$ alkyl, —O—$(CH_2)_r$—$R^{6b}$, —OH, halo, —$NHC(O)CH_3$, and —$C(O)NH_2$;

$R^{6b}$ is selected independently at each occurrence from the group consisting of:
  $C_{1-5}$ alkyl, $C_{3-5}$ cycloalkyl and phenyl;

$R^{6c}$ is selected independently at each occurrence from the group consisting of:
  halogen, $NO_2$, —$R^{6d}$, and —O—$(CH_2)_r$—$R^{6d}$;

$R^{6d}$ is selected independently at each occurrence from the group consisting of:
  $C_{1-5}$ alkyl, $C_{3-5}$ cycloalkyl and phenyl;

alternatively, $R^5$ and $R^6$ combine to form a 3- to 8-membered heterocyclic ring containing 1 to 3 additional heteroatoms selected from —O—, —$NR^6$—, —S(O)p-, and —C(O)—, optionally fused to a phenyl ring;

$R^7$ and $R^8$ may be H or $R^{5a}$;

alternatively, $R^7$ and $R^8$ combine to form 3 to 7 membered heterocyclic ring substituted with 1–3 $R^{7a}$, containing 1–3 additional heteroatoms selected from —O—, —S(O)p-, and —$NR^6$—, optionally fused to an aryl ring substituted with 0–3 $R^{7c}$;

$R^{7a}$ is selected independently at each occurrence from the group consisting of:
  hydrogen, $C_{1-5}$ alkyl, $C_{3-5}$ cycloalkyl, hydroxy, halo, —$OR^{7b}$, —$NHC(O)CH_3$, —$C(O)NH_2$, and aryl;

$R^{7b}$ is selected independently at each occurrence from the group consisting of:
  $C_{1-5}$ alkyl, $C_{1-5}$ cycloalkyl and phenyl;

$R^{7c}$ is selected independently at each occurrence from the group consisting of;
  hydrogen, $C_{1-5}$ alkyl, $C_{3-5}$ cycloalkyl, hydroxy, halo, —$O(CH_2)_r$—$R^{7d}$, —$NHC(O)CH_3$, —$C(O)NH_2$, and aryl;

$R^{7d}$ is selected independently at each occurrence from the group consisting of:
  $C_{1-5}$ alkyl, $C_{1-5}$ cycloalkyl and phenyl;

$R^9$ is selected from the group consisting of:
  hydrogen, $C_{1-5}$ alkyl, —$C(O)OC_{1-5}$ alkyl, —$(CH_2)_r$-aryl substituted with 0–3 $R^{9a}$, and a 5 or 6 membered heterocyclic ring containing from 0 to 2 N, O or S(O)p, and substituted with 0–3 $R^{9a}$;

$R^{9a}$ is selected from the group consisting of:
  —OH, —O—$(CH_2)_r$—$R^{9b}$, —$C(O)OR^{9b}$, —$NHR^{10}$ and aryl;

$R^{9b}$ is selected from the group consisting of:
  $C_{1-5}$ alkyl, $C_{1-5}$ cycloalkyl and phenyl;

$R^{10}$ is independently at each occurrence H or $C_{1-10}$ alkyl substituted with 0–3 $R^{1a}$;

$R^{10a}$ is selected independently at each occurrence from the group consisting of:
  hydrogen, $C_1$–$C_{10}$ alkyl substituted with 0–3 $R^{10b}$, and —$(CH_2)_r$-aryl substituted with 0–3 $R^{10b}$;

$R^{10b}$ is selected independently at each occurrence from the group consisting of:
  hydrogen, halo, hydroxy, —$OR^{10c}$, —$NHC(O)CH_3$, —$(CH_2)_r$—$C(O)NH_2$, -aryl-$NH_2$, and —$SO_2NH_2$;

$R^{10c}$ is selected independently at each occurrence from the group consisting of:
  $C_{1-5}$ alkyl, $C_{1-5}$ cycloalkyl and phenyl;

$R^{11}$ is selected independently at each occurrence from the group consisting of:
  hydrogen, $C_1$–$C_{10}$ alkyl substituted with 0–3 $R^{11a}$, and —$(CH_2)_r$-aryl substituted with 0–3 $R^{11a}$;

$R^{11a}$ is selected independently at each occurrence from the group consisting of:

hydrogen, halo, hydroxy, —OR$^{11b}$, —NHC(O)CH$_3$, —(CH$_2$)$_r$—C(O)NH$_2$, -aryl-NH$_2$, and —SO$_2$NH$_2$;

R$^{11b}$ is selected independently at each occurrence from the group consisting of:
C$_{1-5}$ alkyl, C$_{1-5}$ cycloalkyl and phenyl;

n is selected from 1, 2 and 3;

p is selected independently at each occurrence from 0, 1 and 2;

r is selected independently at each occurrence from 0, 1, 2, and 3;

Y is selected from the group consisting of:
—CONR$^{10}$—, —NR$^{10}$CO—, —SO$_2$NR$^{10}$—, —NR$^{10}$SO$_2$—, and a 5 membered heterocyclic ring; and z is selected from 1, 2, 3, 4 and 5.

15. A compound of formula (IX-a):

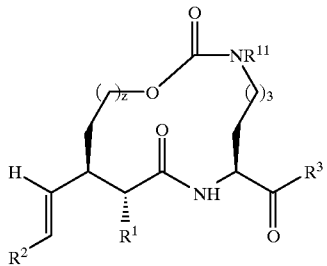

(IX-a)

or a salt form thereof;
wherein:
R$^1$ is selected from the group consisting of:
C$_{1-5}$ alkyl substituted with 0–5 R$^{1a}$, —(CH$_2$)$_r$—C$_{3-10}$ cycloalkyl substituted with 0–5 R$^{1a}$, and —(CH$_2$)$_r$-aryl substituted with 0–5 R$^{1a}$;

R$^{1a}$ is selected independently at each occurrence from the group consisting of:
hydrogen, —CF$_3$, —CF$_2$CF$_3$, —NR$^{1b}$R$^{1c}$, —Si(R$^{1d}$)$_3$, C$_{1-5}$ alkyl, C$_{3-10}$ cycloalkyl, and aryl substituted with 0–5 R$^{1e}$;

R$^{1b}$ and R$^{1c}$ are selected independently at each occurrence from the group consisting of:
C$_{1-5}$ alkyl, C$_{3-5}$ cycloalkyl and phenyl;

R$^{1d}$ is selected independently at each occurrence from the group consisting of:
C$_{1-5}$ alkyl, C$_{1-5}$ haloalkyl, and aryl substituted with 0–5 R$^{1e}$;

R$^{1e}$ is selected independently at each occurrence from the group consisting of:
C$_{1-5}$ alkyl, —(CH$_2$)$_r$—OR$^{1f}$, —OH, halo, —NH$_2$, and —(CF$_2$)$_r$CF$_3$;

R$^{1f}$ is selected independently at each occurrence from the group consisting of:
C$_{1-5}$ alkyl, C$_{3-5}$ cycloalkyl and phenyl;

R$^2$ is selected from the group consisting of:
C$_{1-10}$ alkyl, C$_{3-10}$ cycloalkyl, and —(CH$_2$)$_r$-phenyl substituted with 0–3 R$^{2a}$;

R$^{2a}$ is selected independently at each occurrence from the group consisting of:
C$_{1-5}$ alkyl, —(CH$_2$)$_r$—OR$^{2b}$, —OH, halo, —NH$_2$, and —(CF$_2$)$_r$CF$_3$;

R$^{2b}$ is selected independently at each occurrence from the group consisting of:

C$_{1-5}$ alkyl, C$_{3-5}$ cycloalkyl and phenyl;

R$^3$ is selected from the group consisting of:
—OR$^4$, —NR$^5$R$^6$, —NR$^6$(OR$^5$), C$_{1-5}$ alkyl substituted with 0–3 R$^{3a}$, —(CH$_2$)$_r$-aryl substituted with 0–5 R$^{3a}$, and —(CH$_2$)$_r$-heterocyclic substituted with 0–3 R$^{3a}$;

R$^{3a}$ is selected independently at each occurrence from the group consisting of:
hydrogen, C$_{1-5}$ alkyl, halo, hydroxy, —O—(CH$_2$)$_r$—R$^{3b}$, —(CH$_2$)$_r$—C(O)R$^{3b}$, —(CH$_2$)$_r$—SO$_2$NHR$^{3b}$, —(CH$_2$)$_r$—C(O)NHR$^{3b}$, —(CH$_2$)$_r$—OC(O)R$^{3b}$, —(CH$_2$)$_r$—NHSO$_2$R$^{3b}$, aryl, —(CH$_2$)$_r$—NHC(O)R$^{3b}$, and —(CH$_2$)$_r$—C(O)OR$^{3b}$;

R$^{3b}$ is selected independently at each occurrence from the group consisting of:
C$_{1-5}$ alkyl, C$_{3-5}$ cycloalkyl and phenyl;

R$^4$ is selected from the group consisting of:
hydrogen, C$_1$–C$_{10}$ alkyl, —(CH$_2$)$_r$—C$_{3-10}$ cycloalkyl, —(CH$_2$)$_r$-heterocyclic, and —(CH$_2$)$_r$-aryl substituted with 0–5 R$^{4a}$;

R$^{4a}$ is selected independently at each occurrence from the group consisting of:
C$_{1-5}$ alkyl, —(CH$_2$)$_r$—OR$^{4b}$, —OH, halo, —NH$_2$, and —(CF$_2$)$_r$CF$_3$;

R$^{4b}$ is selected independently at each occurrence from the group consisting of:
C$_{1-5}$ alkyl, C$_{3-5}$ cycloalkyl and phenyl;

R$^5$ is selected from the group consisting of:
C$_{1-5}$ alkyl, —(CH$_2$)$_r$—C$_3$–C$_{10}$ cycloalkyl, —(CHR$^{5a}$Y)$_n$—R$^9$, —(CR$^7$R$^8$)$_n$—O—C(R$^7$R$^8$)$_r$—R$^9$, —(CR$^7$R$^8$)$_r$—R$^9$, and —(CR$^7$R$^8$)$_r$CONR$^7$R$^8$;

R$^{5a}$ is selected independently at each occurrence from the group consisting of:
hydrogen, C$_{1-10}$ alkyl substituted with 0–3 R$^{5b}$, —(CH$_2$)$_r$-aryl substituted with 0–3 R$^{5b}$, and —(CH$_2$)$_r$—O—(CH$_2$)$_r$-aryl substituted with 0–3 R$^{5b}$;

R$^{5b}$ is selected independently at each occurrence from the group consisting of:
hydrogen, halo, hydroxy, —OR$^{5c}$, —NHC(O)CH$_3$, -aryl-(CH$_2$)$_r$—NH$_2$, -aryl-(CH$_2$)$_r$-aryl, C$_{1-10}$ alkyl substituted with 0–3 R$^{5d}$, and —(CH$_2$)$_r$-aryl substituted with 0–3 R$^{5d}$;

R$^{5c}$ is selected independently at each occurrence from the group consisting of:
C$_{1-5}$ alkyl, C$_{3-5}$ cycloalkyl and phenyl;

R$^{5d}$ is selected independently at each occurrence from the group consisting of;
hydrogen, C$_{1-5}$ alkyl, —O—(CH$_2$)$_r$—R$^{5e}$, —OH, halo, —NHC(O)CH$_3$, and —C(O)NH$_2$;

R$^{5e}$ is selected independently at each occurrence from the group consisting of:
C$_{1-5}$ alkyl, C$_{3-5}$ cycloalkyl and phenyl;

R$^6$ is selected from the group consisting of:
hydrogen, C$_1$–C$_{10}$ alkyl, —(CH$_2$)$_r$-aryl, —(CH$_2$)$_r$—C(O)R$^{6a}$, —(CH$_2$)$_r$-heterocyclic, and phenyl substituted with 0–5 R$^{6c}$;

R$^{6a}$ is selected independently at each occurrence from the group consisting of;
hydrogen, C$_{1-5}$ alkyl, —O—(CH$_2$)$_r$—R$^{6b}$, —OH, halo, —NHC(O)CH$_3$, and —C(O)NH$_2$;

$R^{6b}$ is selected independently at each occurrence from the group consisting of:
$C_{1-5}$ alkyl, $C_{3-5}$ cycloalkyl and phenyl;

$R^{6c}$ is selected independently at each occurrence from the group consisting of:
halogen, $NO_2$, $-R^{6d}$, and $-O-(CH_2)_r-R^{6d}$;

$R^{6d}$ is selected independently at each occurrence from the group consisting of:
$C_{1-5}$ alkyl, $C_{3-5}$ cycloalkyl and phenyl;

alternatively, $R^5$ and $R^6$ combine to form a 3 to 8 membered heterocyclic ring containing 1 to 3 additional heteroatoms selected from $-O-$, $-NR^6-$, $-S(O)p-$, and $-C(O)-$, optionally fused to a phenyl ring;

$R^7$ and $R^8$ may be H or $R^{5a}$;

alternatively, $R^7$ and $R^8$ combine to form 3 to 7 membered heterocyclic ring substituted with 1–3 $R^{7a}$, containing 1–3 additional heteroatoms selected from $-O-$, $-S(O)p-$, and $-NR^6-$, optionally fused to an aryl ring substituted with 0–3 $R^{7c}$;

$R^{7a}$ is selected independently at each occurrence from the group consisting of:
hydrogen, $C_{1-5}$ alkyl, $C_{3-5}$ cycloalkyl, hydroxy, halo, $-OR^{7b}$, $-NHC(O)CH_3$, $-C(O)NH_2$, and aryl;

$R^{7b}$ is selected independently at each occurrence from the group consisting of:
$C_{1-5}$ alkyl, $C_{1-5}$ cycloalkyl and phenyl;

$R^{7c}$ is selected independently at each occurrence from the group consisting of;
hydrogen, $C_{1-5}$ alkyl, $C_{3-5}$ cycloalkyl, hydroxy, halo, $-O(CH_2)_r-R^{7d}$, $-NHC(O)CH_3$, $-C(O)NH_2$, and aryl;

$R^{7d}$ is selected independently at each occurrence from the group consisting of:
$C_{1-5}$ alkyl, $C_{1-5}$ cycloalkyl and phenyl;

$R^9$ is selected from the group consisting of:
hydrogen, $C_{1-5}$ alkyl, $-C(O)OC_{1-5}$ alkyl, $-(CH_2)_r$-aryl substituted with 0–3 $R^{9a}$, and a 5 or 6 membered heterocyclic ring containing from 0 to 2 N, O or $S(O)p$, and substituted with 0–3 $R^{9a}$;

$R^{9a}$ is selected from the group consisting of:
$-OH$, $-O-(CH_2)_r-R^{9b}$, $-C(O)OR^{9b}$, $-NHR^{10}$ and aryl;

$R^{9b}$ is selected from the group consisting of:
$C_{1-5}$ alkyl, $C_{1-5}$ cycloalkyl and phenyl;

$R^{10}$ is independently at each occurrence H or $C_{1-10}$ alkyl substituted with 0–3 $R^{10a}$;

$R^{10a}$ is selected independently at each occurrence from the group consisting of:
hydrogen, $C_1$–$C_{10}$ alkyl substituted with 0–3 $R^{10b}$, and $-(CH_2)_r$-aryl substituted with 0–3 $R^{10b}$;

$R^{10b}$ is selected independently at each occurrence from the group consisting of:
hydrogen, halo, hydroxy, $-OR^{10c}$, $-NHC(O)CH_3$, $-(CH_2)_r-C(O)NH_2$, -aryl-$NH_2$, and $-SO_2NH_2$;

$R^{10c}$ is selected independently at each occurrence from the group consisting of:
$C_{1-5}$ alkyl, $C_{1-5}$ cycloalkyl and phenyl;

$R^{11}$ is selected independently at each occurrence from the group consisting of:

hydrogen, $C_1$–$C_{10}$ alkyl substituted with 0–3 $R^{11a}$, and $-(CH_2)_r$-aryl substituted with 0–3 $R^{11a}$;

$R^{11a}$ is selected independently at each occurrence from the group consisting of:
hydrogen, halo, hydroxy, $-OR^{11b}$, $-NHC(O)CH_3$, $-(CH_2)_r-C(O)NH_2$, -aryl-$NH_2$, and $-SO_2NH_2$;

$R^{11b}$ is selected independently at each occurrence from the group consisting of:
$C_{1-5}$ alkyl, $C_{1-5}$ cycloalkyl and phenyl;

n is selected from 1, 2 and 3;

p is selected independently at each occurrence from 0, 1 and 2;

r is selected independently at each occurrence from 0, 1, 2, and 3;

Y is selected from the group consisting of:
$-CONR^{10}-$, $-NR^{10}CO-$, $-SO_2NR^{10}-$, $-NR^{10}SO_2-$, and a 5- membered heterocyclic ring; and z is selected from 1, 2, 3, 4 and 5.

16. The compound of claim 12, wherein the compound of formula (V) is:

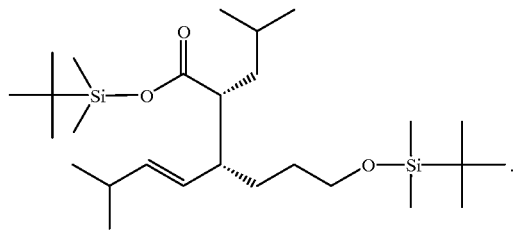

17. The compound of claim 12, wherein the compound of formula (IV-a) is:

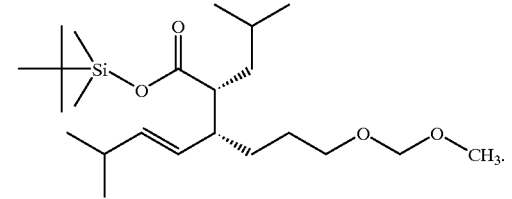

18. The compound of claim 13, wherein the compound of formula (V) is:

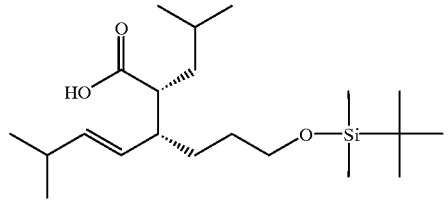

or a salt form thereof.

19. The compound of claim 13, wherein the compound of formula (IV-a) is:
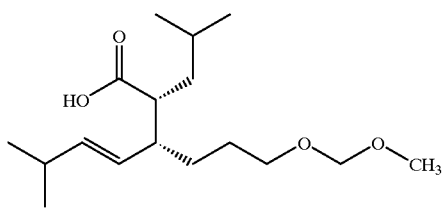
or a salt form thereof.
20. The compound of claim 15, wherein the compound of formula (IX-a) is:
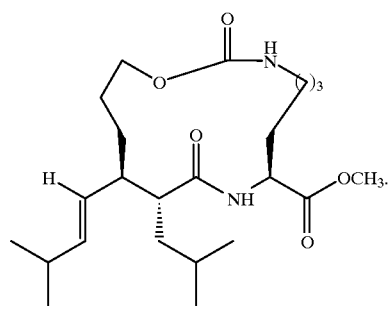
21. the compound of claim 15, wherein the compound of formula (IX-a) is:
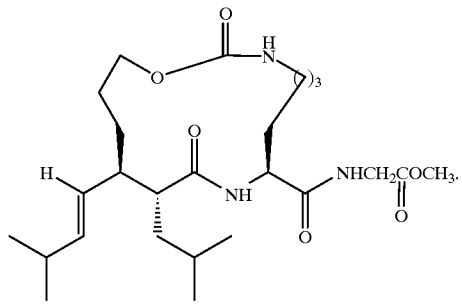
22. The compound of claim 15, wherein the compound of formula (IX-a) is:
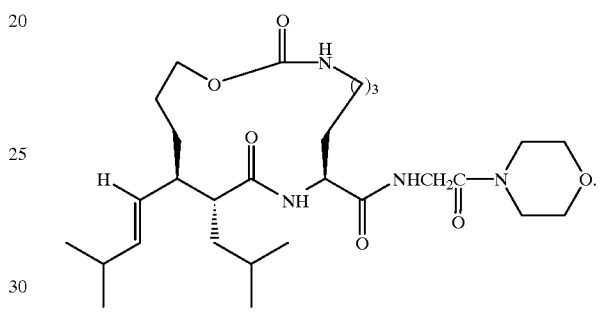
* * * * *